(12) United States Patent
Zoller et al.

(10) Patent No.: US 8,470,841 B2
(45) Date of Patent: Jun. 25, 2013

(54) HETEROCYCLIC COMPOUNDS, PROCESSES FOR THEIR PREPARATION, MEDICAMENTS COMPRISING THESE COMPOUNDS, AND THE USE THEREOF

(75) Inventors: Gerhard Zoller, Frankfurt am Main (DE); Dieter Schmoll, Frankfurt am Main (DE); Marco Mueller, Frankfurt am Main (DE); Guido Haschke, Frankfurt am Main (DE); Ingo Focken, Frankfurt am Main (DE)

(73) Assignee: Sanofi, Paris (FR)

( * ) Notice: Subject to any disclaimer, the term of this patent is extended or adjusted under 35 U.S.C. 154(b) by 1 day.

(21) Appl. No.: 13/002,933

(22) PCT Filed: Jul. 7, 2009

(86) PCT No.: PCT/EP2009/004886
§ 371 (c)(1),
(2), (4) Date: Apr. 14, 2011

(87) PCT Pub. No.: WO2010/003624
PCT Pub. Date: Jan. 14, 2010

(65) Prior Publication Data
US 2011/0183998 A1    Jul. 28, 2011

Related U.S. Application Data

(60) Provisional application No. 61/143,888, filed on Jan. 12, 2009.

(30) Foreign Application Priority Data

Jul. 9, 2008   (EP) .................................. 082906793

(51) Int. Cl.
*A01N 43/40*   (2006.01)
*A61K 31/435*  (2006.01)

(52) U.S. Cl.
USPC ............... 514/277; 514/449; 546/1; 546/184; 549/200

(58) Field of Classification Search
USPC ............... 546/1, 184; 549/200; 514/277, 449, 514/277.449
See application file for complete search history.

(56) References Cited

U.S. PATENT DOCUMENTS 7,928,243 B2   4/2011 Gu et al.

FOREIGN PATENT DOCUMENTS

| EP | 0461958 | 12/1991 |
|---|---|---|
| WO | WO2004020415 | 3/2004 |
| WO | WO2005092836 | 10/2005 |
| WO | WO2008079610 | 7/2008 |

OTHER PUBLICATIONS

Handlon, Anthony L., "Sodium glucose co-transporter 2 (SGLT2) inhibitors as potential antidiabetic agents," Expert Opinion on Therapeutic Patents (2005), vol. 15, pp. 1531-1540.
Asakawa, A. et al., "Cocaine-Amphetamine-Regulated Transcript Influences Energy Metabolism, Anxiety and Gastric Emptying in Mice," Hormone and Metabolic Research (2001), vol. 33, pp. 554-558.
Beckers, Annelies et al., "Chemical Inhibition of Acetyl-CoA Carboxylase Induces Growth Arrest and Cytotoxicity Selectively in Cancer Cells," Cancer Research (2007), vol. 67, pp. 8180-8187.
Berger, Joel P. et al., "PPARs: therapeutic targets for metabolic disease," Trends in Pharmacological Sciences (2005), vol. 26, pp. 244-251.
Carr, Richard D. et al., "NN414, a SUR1/Kir6.2-Selective Potassium Channel Opener, Reduces Blood Glucose and Improves Glucose Tolerance in the VDF Zucker Rat," Diabetes (2003), vol. 52, pp. 2513-2518.
Choi, Cheol Soo et al., "Continuous fat oxidation in acetyl-CoA carboxylase 2 knockout mice increases total energy expenditure, reduces fat mass, and improves insulin sensitivity," Proceedings of the National Academy of Sciences (2007), vol. 104, pp. 16480-16485.
Chen, Desu et al., "A nonpeptidic agonist of glucagon-like peptide 1 receptors with efficacy in diabetic db/db mice," Proceedings of the National Academy of Sciences (2007), vol. 104, pp. 943-948.
Lee, Daniel W. et al., "Leptin agonists as a potential approach to the treatment of obesity," Drugs of the Future (2001), vol. 26, pp. 873-881.
Hansen, J. Bondo et al., "Inhibition of Insulin Secretion as a New Drug Target in the Treatment of Metabolic Disorders," Current Medicinal Chemistry (2004), vol. 11, pp. 1595-1615.
Lee, Dong-Ook et al., "Effects of KST48 [(2R, 5SR)3-(2-Chlorobenzoyl)-5-(4-chlorophenoxymethyl)-2-(3,4-dichlorophenyl)oxazolidine] on Glucose Transport in L6 Myocytes," Arzneimittel Forschung—Drug Research (2004), vol. 54, pp. 835-841.
Coghlan, Michael J. et al., "Recent Developments in the Biology and Medicinal Chemistry of Potassium Channel Modulators: Update from a Decade of Progress," Journal of Medicinal Chemistry (2001), vol. 44, pp. 1627-1653.
Magnard, Clemence et al., "BRCA1 interacts with acetyl-CoA carboxylase through its tandem of BRCT domains," Oncogene (2002), vol. 21, pp. 6729-6739.

(Continued)

Primary Examiner — Paul V. Ward
(74) Attorney, Agent, or Firm — Scully, Scott, Murphy & Presser, P.C.

(57) ABSTRACT

Heterocyclic derivatives, processes for their preparation, medicaments comprising these compounds, and the use thereof. The invention relates to compounds of the formula I in which the radicals R1, R2, R3, R4, W, A, B, D, E, G, L, M, R, T and Y have the stated meanings, and to the physiologically tolerated salts thereof. The compounds are suitable for example for the treatment of the metabolic syndrome, insulin resistance, obesity and diabetes.

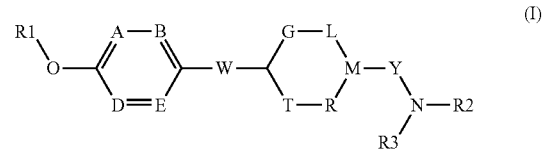

(I)

19 Claims, No Drawings

OTHER PUBLICATIONS

Milgraum, Lea Z. et al., "Enzymes of the Fatty Acid Synthesis Pathway Are Highly Expressed in in Situ Breast Carcinoma," Clinical Cancer Research (1997), vol. 3, pp. 2115-2120.

Munday, M.R., "Regulaion of mammalian acetyl-CoA carboxylase," Biochemical Society Transactions (2002), vol. 30, pp. 1059-1064.

Rote Liste 2007, Kapitel 12, 1, 58.

Ruderman, Neil et al., "AMP Kinase and Malonyl-CoA: Targets for Therapy of the Metabolic Syndrome," Nature Reviews Drug Discovery (2004), vol. 3, pp. 340-351.

Salvador, Javier et al., "Perspectives in the therapeutic use of leptin," Expert Opinion on Pharmacotherapy (2001), vol. 2, pp. 1615-1622.

Savage, David B. et al., "Reversal of diet-induced hepatic steatosis and hepatic insulin resistance by antisense oligonucleotide inhibitors of acetyl-CoA carboxylases 1 and 2," The Journal of Clinical Investigation (2006), vol. 116, pp. 817-824.

Swinnen, Johannes V. et al., "Selective Activation of the Fatty Acid Synthesis Pathway in Human Prostate Cancer," International Journal of Cancer (2000), vol. 88, pp. 176-179.

Tagmose, Tina M. et al., "Arylcyanoguanidines as Activators of Kir6.2/SUR1KATP Channels and Inhibitors of Insulin Release," Journal of Medicinal Chemistry (2004), vol. 47, pp. 3202-3211.

Zunft, H.J.F. et al., "Carob Pulp Preparation for Treatment of Hypercholesterolemia," Advances in Natural Therapy (2001), vol. 18, pp. 230-236.

International Preliminary Report on Patentability dated Jan. 11, 2011.

International Search Report dated Mar. 5, 2010.

HETEROCYCLIC COMPOUNDS, PROCESSES FOR THEIR PREPARATION, MEDICAMENTS COMPRISING THESE COMPOUNDS, AND THE USE THEREOF

CROSS-REFERENCE TO RELATED APPLICATIONS

This application claims the benefit of U.S. Provisional Application No. 61/143,888 filed on Jan. 12, 2009.

The invention relates to heterocyclic compounds and the physiologically tolerated salts thereof.

The invention was based on the object of providing novel compounds which display a therapeutically useful effect. The object was in particular to find novel compounds suitable for treating elevated lipid concentrations in the blood and in tissues, dysregulation of LDL, HDL and VLDL, the metabolic syndrome, obesity, especially visceral (abdominal) obesity, including prevention of the sequelae associated therewith, diabetes, insulin resistance or cardiovascular disorders.

Influencing fatty acid metabolism is considered in the literature to be one therapeutic option for treating excessive deposition of fatty acids in organs and the disorders associated therewith, such as obesity, diabetes, atherosclerosis, impaired lipid profiles and cardiovascular disorders. One interesting mechanism for reducing the pathological deposition of lipids is represented by reducing fatty acid synthesis and increasing fatty acid oxidation by inhibiting acetyl CoA carboxylase. Inhibition of acetyl-CoA carboxylase of isoform 2 is considered in particular to be an interesting therapeutic approach.

Numerous publications and patent applications on the inhibition of acetyl-CoA carboxylase and the therapeutic use have appeared in the literature. The current state of the art is summarized in "Recent Patents on Cardiovascular Drug Discovery (2007), 2: 162-180".

Similar compounds with a pharmacological effect have been described in the prior art, in EP461958. WO2007000246 describes compounds for stimulating the expression of endothelial NO synthase.

The invention therefore relates to compounds of the formula I

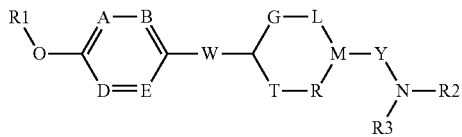

in which the meanings are

A, B, D, E independently of one another C(R5) or N,
  where not more than two of the radicals A, B, D, E may have the meaning of N;
G, L, R, T, independently of one another =C(R6)-, —C(R6)(R7)-, =N—, —N(R8)- or O, where not more than two of the radicals G, L, R, T may have the meaning of =N—, —N(R8)- or O;
  with the proviso that A, B, D, E and G, L, R, T and the C atoms to which they are bonded do not simultaneously form phenyl;
M =C—, —C(R9)- or N;
W O, S, CH(R10);
Y ($C_2$-$C_{10}$)-alkylene, where one or two $CH_2$ groups may be replaced by O, S, N(R10a), —CH=CH—, —CH(phenyl)- or CON(R10b);
R1 ($C_1$-$C_{16}$)-alkyl, ($C_1$-$C_2$)-haloalkyl, ($C_6$-$C_{10}$)-aryl, ($C_3$-$C_{12}$)-heteroaryl, ($C_3$-$C_{12}$)-heterocyclyl, ($C_3$-$C_{12}$)-cycloalkyl, ($C_1$-$C_6$)-alkylene-($C_6$-$C_{10}$)-aryl, ($C_1$-$C_6$)-alkylene-($C_3$-$C_{12}$)-heteroaryl, ($C_1$-$C_6$)-alkylene-($C_3$-$C_{12}$)-heterocyclyl or ($C_1$-$C_6$)-alkylene-($C_3$-$C_{12}$)-cycloalkyl,
  where aryl, heteroaryl, heterocyclyl or cycloalkyl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R11)(R12), $SO_2$—$CH_3$, $SO_2$—$NH_2$, $SF_5$, oxo, COOH, COO—($C_1$-$C_6$)-alkyl, CON(R13)(R14), N(R15)CO(R16), N(R17)$SO_2$(R18), CO(R19), (CR20R21)$_x$-O(R22), O—CO—N(R23)(R24), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R25)(R26);
x 0, 1, 2, 3, 4, 5, 6;
R10a, R10b, R11, R12, R13, R14, R15, R16, R17, R18, R19, R20, R21, R22, R23, R24, R25, R26
  independently of one another hydrogen, ($C_1$-$C_6$)-alkyl;
R2 hydrogen, —CO—N(R3a)-R4, —CO—R4, —CO—O—R4, ($C_3$-$C_{12}$)-heteroaryl,
  where heteroaryl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R27)(R28), $SO_2$—$CH_3$, $SO_2$—$NH_2$, $SF_5$, COOH, COO—($C_1$-$C_6$)-alkyl, CON(R29)(R30), N(R31)CO(R32), N(R33)$SO_2$(R34), CO(R35), (CR36R37)$_{x'}$-O(R38), O—CO—N(R39)(R40), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R41)(R42),
x' 0, 1, 2, 3, 4, 5, 6;
R3, R3a independently of one another hydrogen, ($C_1$-$C_6$)-alkyl, benzyl;
R4 hydrogen, ($C_1$-$C_{16}$)-alkyl, ($C_1$-$C_6$)-alkylen-OH, ($C_6$-$C_{10}$)-aryl, ($C_3$-$C_{12}$)-heteroaryl, —($C_3$-$C_{12}$)-heterocyclyl, ($C_3$-$C_{12}$)-cycloalkyl, ($C_1$-$C_6$)-alkylene-($C_6$-$C_{10}$)-aryl, ($C_1$-$C_6$)-alkylene-($C_3$-$C_{12}$)-heteroaryl, ($C_1$-$C_6$)-alkylene-($C_3$-$C_{12}$)-heterocyclyl or ($C_1$-$C_6$)-alkylene-($C_3$-$C_{12}$)-cycloalkyl,
  where aryl, heteroaryl, heterocyclyl or cycloalkyl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R43)(R44), $SO_2$—$CH_3$, $SO_2$—$NH_2$, $SF_5$, COOH, COO—($C_1$-$C_6$)-alkyl, CON(R45)(R46), N(R47)CO(R48), N(R49)$SO_2$(R50), CO(R51), (CR52R53)$_{x''}$-O(R54), O—CO—N(R55)(R56), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R57)(R58),
x" 0, 1, 2, 3, 4, 5, 6;
R27, R28, R29, R30, R31, R32, R33, R34, R35, R36, R37, R38, R39, R40, R41,
R42, R43, R44, R45, R46, R47, R48, R49, R50, R51, R52, R53, R54, R55, R56, R57, R58
  independently of one another hydrogen, ($C_1$-$C_6$)-alkyl;
R5 independently of one another hydrogen, ($C_1$-$C_6$)-alkyl, F, Cl, Br, I, OH, $CF_3$, $NO_2$, CN, ($C_2$-$C_4$)-haloalkyl, ($C_2$-$C_6$)- alkenyl, $(C_2-C_6)$-alkynyl, N(R59)(R60), $SO_2$—$CH_3$, $SO_2$—$NH_2$, $SF_5$, COOH, COO—$(C_1-C_6)$-alkyl, CON(R61)(R62), N(R63)CO(R64), N(R65)$SO_2$(R66), CO(R67), $(CR68R69)_{x'''}$-O(R70), O—CO—N(R71)(R72), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R73)(R74);

x''' 0, 1, 2, 3, 4, 5, 6;

R6, R7 independently of one another hydrogen, $(C_1-C_6)$-alkyl, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R75)(R76), $SO_2$—$CH_3$, $SO_2$—$NH_2$, $SF_5$, oxo COOH, COO—$(C_1-C_6)$-alkyl, CON(R77)(R78), N(R79)CO(R80), N(R81)$SO_2$(R82), CO(R83), $(CR84R85)_{x''''}$-O(R86), O—CO—N(R87)(R88), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R89)(R90);

R8 independently of one another hydrogen, $(C_1-C_6)$-alkyl, $CF_3$, CN, $(C_1-C_6)$-alkyl, $(C_2-C_4)$-haloalkyl, $(C_2-C_6)$-alkenyl, $(C_2-C_6)$-alkynyl, $SO_2$—$CH_3$, $SO_2$—$NH_2$, COO—$(C_1-C_6)$-alkyl, CON(R77)(R78), CO(R83), $(CR84R85)_{x''''}$-O(R86);

x'''' 0, 1, 2, 3, 4, 5, 6;

R9, R10 independently of one another hydrogen, $(C_1-C_6)$-alkyl, F, OH, $CF_3$, $(C_2-C_4)$-haloalkyl, $(C_2-C_6)$-alkenyl, $(C_2-C_6)$-alkynyl, $(CR91R92)_y$-O(R93);

y 0, 1, 2, 3, 4, 5, 6;

R59, R60, R61, R62, R63, R64, R65, R66, R67, R68, R69, R70, R71, R72, R73,

R74, R75, R76, R77, R78, R79, R80, R81, R82, R83, R84, R85, R86, R87, R88, R89, R90, R91, R92, R93 independently of one another hydrogen, $(C_1-C_6)$-alkyl;

and the pharmaceutically acceptable salts thereof.

Preference is given to compounds of the formula I in which the meanings are

A, B, D, E independently of one another C(R5) or N, where not more than two of the radicals A, B, D, E may have the meaning of N;

G, L, R, T independently of one another =C(R6)-, —C(R6)(R7)-, =N—, —N(R8)- or O, where not more than two of the radicals G, L, R, T may have the meaning of =N—, —N(R8)- or O;

with the proviso that A, B, D, E and G, L, R, T and the C atoms to which they are bonded do not simultaneously form phenyl.

M =C—, —C(R9)- or N;

W O, S, CH(R10);

Y $(C_2-C_6)$-alkylene, where one $CH_2$ group may be replaced by O, S, N(R10a) or CON(R10b).

R1 $(C_3-C_{12})$-alkyl, $(C_1-C_2)$-haloalkyl, $(C_6-C_{10})$-aryl, $(C_3-C_{12})$-heteroaryl, $(C_3-C_{12})$-heterocyclyl, $(C_3-C_{12})$-cycloalkyl, $(C_1-C_2)$-alkylene-$(C_6-C_{10})$-aryl, $(C_1-C_2)$-alkylene-$(C_3-C_{12})$-heteroaryl, $(C_1-C_2)$-alkylene-$(C_3-C_{12})$-heterocyclyl or $(C_1-C_2)$-alkylene-$(C_3-C_{12})$-cycloalkyl, where aryl, heteroaryl, heterocyclyl or cycloalkyl may be substituted once, twice or three times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R11)(R12), $SO_2$—$CH_3$, $SO_2$—$NH_2$, oxo, COOH, COO—$(C_1-C_6)$-alkyl, CON(R13)(R14), N(R15)CO(R16), N(R17)$SO_2$(R18), CO(R19), $(CR20R21)_x$-O(R22), O—CO—N(R23)(R24), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R25)(R26);

x 0, 1, 2, 3, 4, 5, 6;

R10a, R10b, R11, R12, R13, R14, R15, R16, R17, R18, R19, R20, R21, R22, R23, R24, R25, R26 independently of one another hydrogen, $(C_1-C_6)$-alkyl;

R2 CO—N(R3a)-R4, —CO—R4, —CO—O—R4, $(C_3-C_{12})$-heteroaryl, where heteroaryl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R27)(R28), $SO_2$—$CH_3$, $SO_2$—$NH_2$, COOH, COO—$(C_1-C_6)$-alkyl, CON(R29)(R30), N(R31)CO(R32), N(R33)$SO_2$(R34), CO(R35), $(CR36R37)_{x'}$-O(R38), O—CO—N(R39)(R40), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R41)(R42), x' 0, 1, 2, 3, 4, 5, 6;

R3, R3a independently of one another hydrogen, $(C_1-C_6)$-alkyl, benzyl;

R4 $(C_1-C_{12})$-alkyl, $(C_6-C_{10})$-aryl, $(C_3-C_{12})$-heteroaryl, $(C_3-C_{12})$-heterocyclyl, $(C_3-C_{12})$-cycloalkyl, $(C_1-C_6)$-alkylene-$(C_6-C_{10})$-aryl, $(C_1-C_6)$-alkylene-$(C_3-C_{12})$-heteroaryl, $(C_1-C_6)$-alkylene-$(C_3-C_{12})$-heterocyclyl or $(C_1-C_6)$-alkylene-$(C_3-C_{12})$-cycloalkyl, where aryl, heteroaryl, heterocyclyl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R43)(R44), $SO_2$—$CH_3$, $SO_2$—$NH_2$, COOH, COO—$(C_1-C_6)$-alkyl, CON(R45)(R46), N(R47)CO(R48), N(R49)$SO_2$(R50), CO(R51), $(CR52R53)_{x''}$-O(R54), O—CO—N(R55)(R56), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R57)(R58), x'' 0, 1, 2, 3, 4, 5, 6;

R27, R28, R29, R30, R31, R32, R33, R34, R35, R36, R37, R38, R39, R40, R41,

R42, R43, R44, R45, R46, R47, R48, R49, R50, R51, R52, R53, R54, R55, R56, R57, R58 independently of one another hydrogen, $(C_1-C_6)$-alkyl;

R5 independently of one another hydrogen, $(C_1-C_6)$-alkyl, F, Cl, Br, I, OH, $CF_3$, $NO_2$, CN, $(C_2-C_4)$-haloalkyl, $(C_2-C_6)$-alkenyl, $(C_2-C_6)$-alkynyl, N(R59)(R60), COO—$(C_1-C_6)$-alkyl, CON(R61)(R62), N(R63)CO(R64), N(R65)$SO_2$(R66), CO(R67), $(CR68R69)_{x'''}$-O(R70);

x''' 0, 1, 2, 3, 4, 5, 6;

R6, R7 independently of one another hydrogen, $(C_1-C_6)$-alkyl, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R75)(R76), oxo, COO—$(C_1-C_6)$-alkyl, CON(R77)(R78), N(R79)CO(R80), N(R81)$SO_2$(R82), CO(R83), $(CR84R85)_{x''''}$-O(R86);

R8 independently of one another hydrogen, $(C_1-C_6)$-alkyl, $CF_3$, CN, $(C_1-C_6)$-alkyl, $(C_2-C_4)$-haloalkyl, $(C_2-C_6)$-alkenyl, $(C_2-C_6)$-alkynyl, COO—$(C_1-C_6)$-alkyl, CON(R77)(R78), CO(R83), $(CR84R85)_{x''''}$-O(R86);

$x''''$ 0, 1, 2, 3, 4, 5, 6;

R9, R10 independently of one another hydrogen, $(C_1-C_6)$-alkyl, F, OH, $CF_3$, $(C_2-C_4)$-haloalkyl, $(C_2-C_6)$-alkenyl, $(C_2-C_6)$-alkynyl, $(CR91R92)_y$-O(R93);

y 0, 1, 2, 3, 4, 5, 6;

R59, R60, R61, R62, R63, R64, R65, R66, R67, R68, R69, R70, R75, R76, R77, R78, R79, R80, R81, R82, R83, R84, R85, R86, R91, R92, R93 independently of one another hydrogen, $(C_1-C_6)$-alkyl;

and the pharmaceutically acceptable salts thereof.

Particular preference is given to compounds of the formula I in which the meanings are A, B, D, E form with the atoms to which they are bonded a ring system selected from the group:

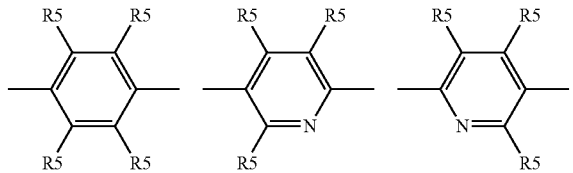

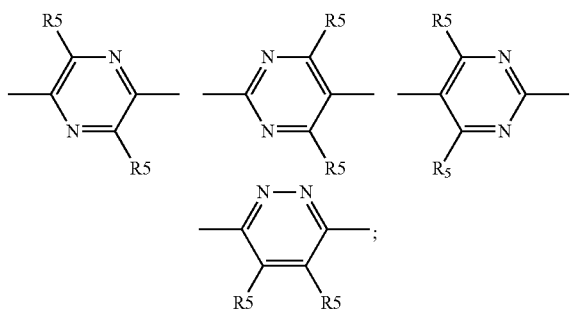

G, L, R, T and M form a ring system selected from the group:

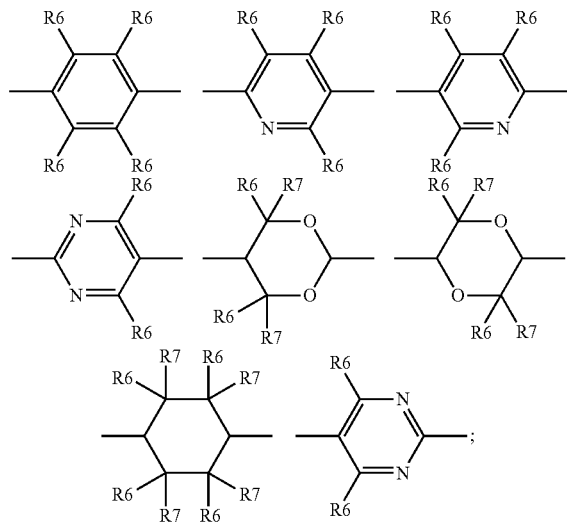

with the proviso that A, B, D, E and G, L, R, T and the C atoms to which they are bonded do not simultaneously form phenyl;

W O, S, CH(R10);

Y C(R11a)(R11b)C(R11c)(R11d)C(R11e)(R11f)-, O—C(R11a)(R11b)C(R11c)(R11d)-, —S—C(R11a)(R11b)C(R11c)(R11d), —CH═CH—C(R11a)(R11b)-;

R1 $(C_1-C_{16})$-alkyl, $(C_1-C_2)$-haloalkyl, $(C_6-C_{10})$-aryl, $(C_3-C_{12})$-heteroaryl, $(C_3-C_{12})$-heterocyclyl, $(C_3-C_{12})$-cycloalkyl, $(C_1-C_6)$-alkylene-$(C_6-C_{10})$-aryl, $(C_1-C_6)$-alkylene-$(C_3-C_{12})$-heteroaryl, $(C_1-C_6)$-alkylene-$(C_3-C_{12})$-heterocyclyl or $(C_1-C_6)$-alkylene-$(C_3-C_{12})$-cycloalkyl, where aryl, heteroaryl, heterocyclyl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_5)$-cycloalkyl, O—$(C_3-C_8)$-cycloalkyl, $(C_2-C_6)$-alkynyl, N(R11)(R12), $SO_2$—$CH_3$, $SO_2$—$NH_2$, $SF_5$, oxo, COOH, COO—$(C_1-C_6)$-alkyl, CON(R13)(R14), N(R15)CO(R16), N(R17)$SO_2$(R18), CO(R19), $(CR20R21)_x$-O(R22), O—CO—N(R23)(R24), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R25)(R26);

x 0, 1, 2, 3, 4, 5, 6;

R10a, R10b, R11, R12, R13, R14, R15, R16, R17, R18, R19, R20, R21, R22, R23, R24, R25, R26 independently of one another hydrogen, $(C_1-C_6)$-alkyl;

R11a, R11b, R11c, R11d, R11e, R11f independently of one another hydrogen, $(C_1-C_3)$-alkyl, phenyl;

R2 CO—N(R3a)-R4, —CO—R4, —CO—O—R4,

R3, R3a independently of one another hydrogen, $(C_1-C_6)$-alkyl, benzyl;

R4 hydrogen, $(C_1-C_{12})$-alkyl, $(C_1-C_6)$-alkylene-OH, phenyl $(C_3-C_{12})$-heteroaryl, $(C_3-C_{12})$-heterocyclyl, $(C_3-C_{12})$-cycloalkyl, $(C_1-C_6)$-alkylene-$(C_6-C_{10})$-aryl, $(C_1-C_6)$-alkylene-$(C_3-C_{12})$-heteroaryl, $(C_1-C_6)$-alkylene-$(C_3-C_{12})$-heterocyclyl or $(C_1-C_6)$-alkylene-$(C_3-C_{12})$-cycloalkyl, where aryl, heteroaryl, heterocyclyl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R43)(R44), $SO_2$—$CH_3$, $SO_2$—$NH_2$, COOH, COO—$(C_1-C_6)$-alkyl, CON(R45)(R46), N(R47)CO(R48), N(R49)$SO_2$(R50), CO(R51), $(CR52R53)_{x''}$-O(R54), O—CO—N(R55)(R56), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R57)(R58);

$x''$ 0, 1, 2, 3;

R43, R44, R45, R46, R47, R48, R49, R50, R51, R52, R53, R54, R55, R56, R57, R58 independently of one another, hydrogen, $(C_1-C_6)$-alkyl;

R5 independently of one another hydrogen, $(C_1-C_6)$-alkyl, F, Cl, Br, I, OH, $CF_3$, $NO_2$, CN, $(C_2-C_4)$-haloalkyl, $(C_2-C_6)$-alkenyl, $(C_2-C_6)$-alkynyl, N(R59)(R60), $SO_2$—$CH_3$, $SO_2$—$NH_2$, $SF_5$, COOH, COO—$(C_1-C_6)$-alkyl, CON(R61)(R62), N(R63)CO(R64), N(R65)$SO_2$(R66), CO(R67), $(CR68R69)_{x'''}$-(R70), O—CO—N(R71)(R72), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R73)(R74);

$x'''$ 0, 1, 2, 3, 4, 5, 6;

R6, R7 independently of one another hydrogen, (C$_1$-C$_6$)-alkyl, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_2$-C$_6$)-alkynyl, N(R75)(R76), SO$_2$—CH$_3$, SO$_2$—NH$_2$, SF$_5$, oxo, COOH, COO—(C$_1$-C$_6$)-alkyl, CON(R77)(R78), N(R79)CO(R80), N(R81)SO$_2$(R82), CO(R83), (CR84R85)$_{x''''}$-O(R86), O—CO—N(R87)(R88), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R89)(R90);

x'''' 0, 1, 2, 3, 4, 5, 6;

R10 hydrogen, (C$_1$-C$_6$)-alkyl, F, OH, CF$_3$;

R59, R60, R61, R62, R63, R64, R65, R66, R67, R68, R69, R70, R75, R76, R77, R78, R79, R80, R81, R82, R83, R84, R85, R86, R87, R88, R89, R90 independently of one another hydrogen, (C$_1$-C$_6$)-alkyl;

and the pharmaceutically acceptable salts thereof.

A further preferred embodiment is a compound of the formula I in which the meanings are A, B, D, E form with the atoms to which they are bonded a ring system selected from the group:

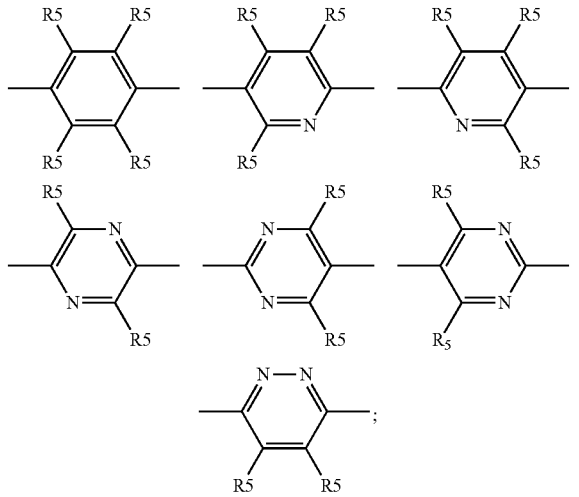

G, L, R, T and M form a ring system selected from the group:

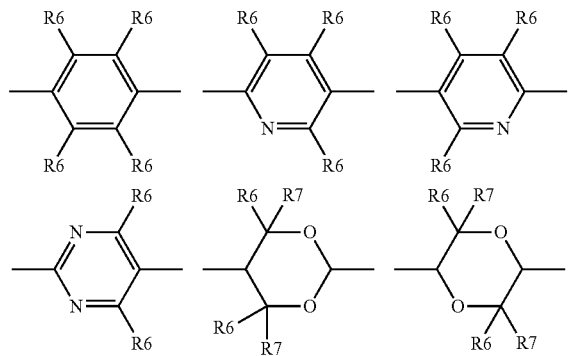

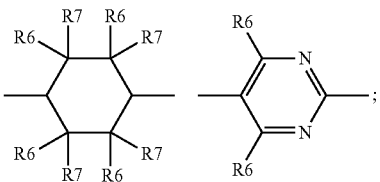

with the proviso that A, B, D, E and G, L, R, T and the C atoms to which

W O, CHOH, CH$_2$;

Y C(R11a)(R11b)C(R11c)(R11d)C(R11e)(R11f)-, O—C(R11a)(R11b)C(R11c)(R11d)-, —S—C(R11a)(R11b)C(R11c)(R11d), —CH=CH—C(R11a)(R11b)-;

R1 (C$_1$-C$_8$)-alkyl, CF$_3$, phenyl, (C$_3$-C$_8$)-heteroaryl, (C$_3$-C$_8$)-heterocyclyl, (C$_3$-C$_8$)-cycloalkyl, —CH$_2$-phenyl, —CH$_2$—(C$_3$-C$_8$)-heteroaryl, —CH$_2$—(C$_3$-C$_8$)-heterocyclyl or —CH$_2$—(C$_3$-C$_8$)-cycloalkyl, where aryl, heteroaryl, heterocyclyl or cycloalkyl may be substituted one or more times by F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_2$-C$_6$)-alkynyl, N(R11)(R12), SO$_2$—CH$_3$, SO$_2$—NH$_2$, oxo, COOH, COO—(C$_1$-C$_6$)-alkyl, CON(R13)(R14), N(R15)CO(R16), N(R17)SO$_2$(R18), CO(R19), (CR20R21)$_x$-O(R22), O—CO—N(R23)(R24), O—CO—(C$_1$-C$_6$)-alkylene-CO—O—(C$_1$-C$_6$)-alkyl;

x 0, 1, 2, 3;

R11a, R11b, R11, R11d, R11e, R11f independently of one another hydrogen, methyl, isopropyl, phenyl;

R11, R12, R13, R14, R15, R16, R17, R18, R19, R20, R21, R22, R23, R24 independently of one another hydrogen, (C$_1$-C$_6$)-alkyl;

R2 —CO—R4, —CO—O—R4;

R3 hydrogen, (C$_1$-C$_6$)-alkyl;

R4 hydrogen, methyl, benzyl, cyclopropyl, CH$_2$OH, NH$_2$;

R5 independently of one another hydrogen, (C$_1$-C$_6$)-alkyl, F, Cl, Br, I, OH, CF$_3$, N(R59)(R60), COO—(C$_1$-C$_6$)-alkyl, CON(R61)(R62), N(R63)CO(R64), CO(R67), (CR68R69)$_{x'''}$-O(R70);

x''' 0, 1, 2, 3, 4, 5, 6;

R6, R7 independently of one another hydrogen, (C$_1$-C$_6$)-alkyl, F, Cl, Br, I, OH, CF$_3$, O—(C$_1$-C$_6$)-alkyl, O—(C$_1$-C$_4$)-alkoxy-(C$_1$-C$_4$)-alkyl, N(R75)(R76), COO—(C$_1$-C$_6$)-alkyl, CON(R77)(R78), CO(R83), (CR84R85)$_{x''''}$-O(R86);

x'''' 0, 1, 2, 3, 4, 5, 6;

R59, R60, R61, R62, R63, R64, R67, R68, R69, R70, R75, R76, R77, R78, R83, R84, R85, R86 independently of one another hydrogen, (C$_1$-C$_6$)-alkyl;

and the pharmaceutically acceptable salts thereof.

Particular preference is likewise given to compounds of the formula I in which the meanings are A, B, D, E independently of one another C(R5) or N, where not more than two of the radicals A, B, D, E may have the meaning of N;

G, L, R, T and M form a ring system selected from the group:

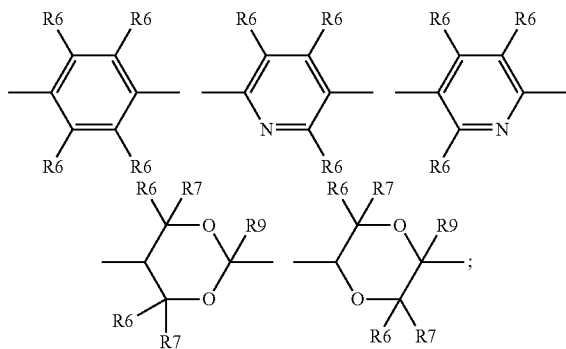

with the proviso that A, B, D, E and G, L, R, T and the C atoms to which they are bonded do not simultaneously form phenyl;

W O, S, CH(R10);

Y C(R11a)(R11b)C(R11c)(R11d)C(R11e)(R11f)-, O—C(R11a)(R11b)C(R11c)(R11d)-, —S—C(R11a)(R11b)C(R11c)(R11d)-;

R1 $(C_3-C_8)$-alkyl, $CF_3$, phenyl, $(C_3-C_8)$-heteroaryl, $(C_3-C_8)$-heterocyclyl, $(C_3-C_8)$-cycloalkyl, —$CH_2$-phenyl, —$CH_2$—$(C_3-C_8)$-heteroaryl, —$CH_2$—$(C_3-C_8)$-heterocyclyl or —$CH_2$—$(C_3-C_8)$-cycloalkyl, where aryl, heteroaryl, heterocyclyl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R11)(R12), $SO_2$—$CH_3$, $SO_2$—$NH_2$, oxo, COOH, COO—$(C_1-C_6)$-alkyl, CON(R13)(R14), N(R15)CO(R16), N(R17)$SO_2$(R18), CO(R19), (CR20R21)$_x$-O(R22), O—CO—N(R23)(R24), O—CO—$(C_1-C_6)$-alkylene-CO—O—$(C_1-C_6)$-alkyl;

x 0, 1, 2, 3;

R11a, R11b, R11c, R11d, R11e, R11f independently of one another hydrogen, $(C_1-C_2)$-alkyl;

R11, R12, R13, R14, R15, R16, R17, R18, R19, R20, R21, R22, R23, R24 independently of one another hydrogen, $(C_1-C_6)$-alkyl;

R2 —CO—R4, —CO—O—R4, $(C_3-C_8)$-heteroaryl, where heteroaryl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R27)(R28), $SO_2$—$CH_3$, $SO_2$—$NH_2$, COO—$(C_1-C_6)$-alkyl, CON(R29)(R30), N(R31)CO(R32), N(R33)$SO_2$(R34), CO(R35), (CR36R37)$_{x'}$-O(R38), O—CO—N(R39)(R40), O—CO—$(C_1-C_6)$-alkylene-CO—O—$(C_1-C_6)$-alkyl, x' 0, 1, 2, 3;

R3, R3a independently of one-another hydrogen, $(C_1-C_6)$-alkyl;

R4 $(C_1-C_8)$-alkyl, phenyl, $(C_3-C_8)$-heteroaryl, $(C_3-C_8)$-heterocyclyl, $(C_3-C_8)$-cycloalkyl, —$CH_2$-phenyl, —$CH_2$—$(C_3-C_8)$-heteroaryl, —$CH_2$—$(C_3-C_8)$-heterocyclyl or —$CH_2$—$(C_3-C_8)$-cycloalkyl, where aryl, heteroaryl, heterocyclyl or cycloalkyl may be substituted once, twice or three times by F, Cl, Br, I, OH, $CF_3$, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R43)(R44), oxo, COO—$(C_1-C_6)$-alkyl, CON(R45)(R46), N(R47)CO(R48), N(R49)$SO_2$(R50), CO(R51), (CR52R53)$_{x''}$-O(R54), x" 0, 1, 2, 3;

R27, R28, R29, R30, R31, R32, R33, R34, R35, R36, R37, R38, R39, R40, R43, R44, R45, R46, R47, R48, R49, R50, R51, R52, R53, R54 independently of one another, hydrogen, $(C_1-C_6)$-alkyl;

R5 independently of one another hydrogen, $(C_1-C_6)$-alkyl, F, Cl, Br, I, OH, $CF_3$, N(R59)(R60), COO—$(C_1-C_6)$-alkyl, CON(R61)(R62), N(R63)CO(R64), CO(R67), (CR68R69)$_{x'''}$-O(R70);

x''' 0, 1, 2, 3, 4, 5, 6;

R6, R7 independently of one another hydrogen, $(C_1-C_6)$-alkyl, F, Cl, Br, I, OH, $CF_3$, O—$(C_1-C_6)$-alkyl, O—$(C_1-C_4)$-alkoxy-$(C_1-C_4)$-alkyl, N(R75)(R76), COO—$(C_1-C_6)$-alkyl, CON(R77)(R78), CO(R83), (CR84R85)$_{x''''}$-O(R86);

x"" 0, 1, 2, 3, 4, 5, 6;

R9, R10 hydrogen;

R59, R60, R61, R62, R63, R64, R67, R68, R69, R70, R75, R76, R77, R78, R83, R84, R85, R86 independently of one another hydrogen, $(C_1-C_6)$-alkyl;

and the pharmaceutically acceptable salts thereof.

Very particular preference is given to compounds of the formula I in which the meanings are A, B, D, E form with the atoms to which they are bonded a ring system selected from the group:

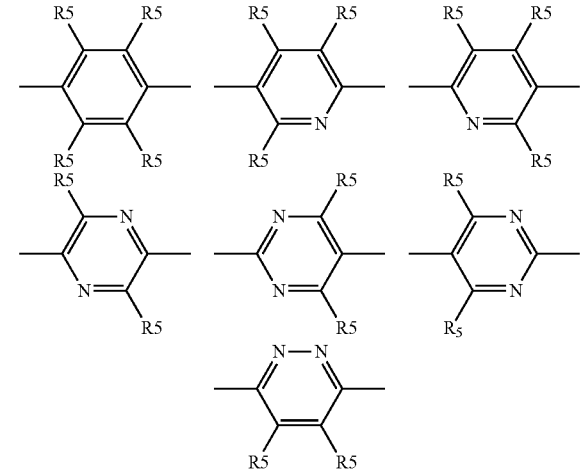

G, L, R, T and M form a ring system selected from the group:

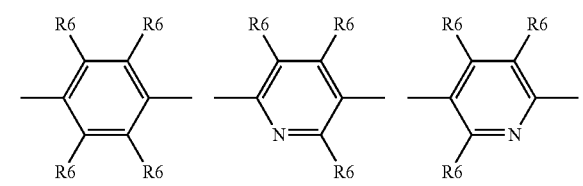

-continued

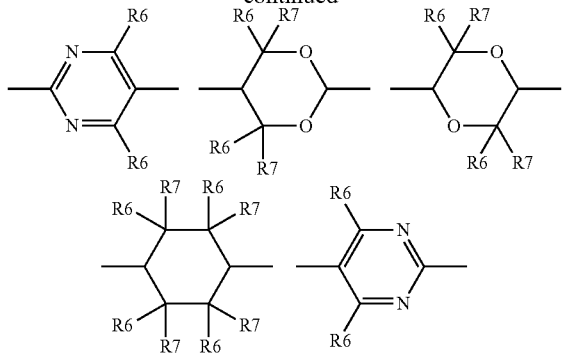

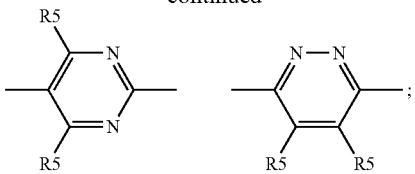

with the proviso that A, B, D, E and G, L, R, T and the C atoms to which they are bonded do not simultaneously form phenyl;

W O, CHOH, CH$_2$;

Y C(R11a)(R11b)C(R11c)(R11d)C(R11e)(R11f)-, O—C(R11a)(R11b)C(R11c)(R11d)-, —S—C(R11a)(R11b)C(R11c)(R11d)-CH=CH—C(R11a)(R11b)-;

R1 (C$_3$-C$_8$)-alkyl, CF$_3$, phenyl, pyridyl, isoxazolyl, pyrrolidinyl, cyclopentyl, tetrahydrofuranyl, —CH$_2$-phenyl, —CH$_2$-isoxazolyl, —CH$_2$-pyrrolidinyl, —CH$_2$-cyclobutyl, —CH$_2$-cyclopropyl or —CH$_2$-cyclopentyl;

where each of the rings may be substituted once or twice by F, Cl, Br, I, OH, CF$_3$, O—(C$_1$-C$_6$)-alkyl (C$_1$-C$_6$)-alkyl, (C$_2$-C$_4$)-haloalkyl, O—(C$_2$-C$_4$)-haloalkyl, N(R11)(R12), CO(R19), (CR20R21)$_x$-O(R22), O—CO—N(R23)(R24);

x 0, 1, 2, 3;

R11a, R11b, R11, R11d, R11e, R11f
independently of one another hydrogen, methyl, isopropyl, phenyl;

R11, R12, R19, R20, R21, R22, R23, R24
independently of one another hydrogen, (C$_1$-C$_6$)-alkyl;

R2 —CO—R4, —CO—O—R4;

R3 hydrogen, (C$_1$-C$_6$)-alkyl;

R4 hydrogen, methyl, benzyl, cyclopropyl, CH$_2$OH, NH$_2$;

R5 independently of one another hydrogen, (C$_1$-C$_6$)-alkyl, F, Cl, Br, I, OH, CF$_3$, O—(C$_1$-C$_6$)-alkyl, N(R59)(R60), COO—(C$_1$-C$_6$)-alkyl, CO(R67);

R6, R7 independently of one another hydrogen, (C$_1$-C$_6$)-alkyl, F, Cl, Br, I, OH, CF$_3$, O—(C$_1$-C$_6$)-alkyl, N(R75)(R76), COO—(C$_1$-C$_6$)-alkyl, CO(R83);

R59, R60, R67, R75, R76, R83
independently of one another hydrogen, (C$_1$-C$_6$)-alkyl;

and the pharmaceutically acceptable salts thereof.

Very particular preference is likewise given to compounds of the formula I in which the meanings are A, B, D, E form with the atoms to which they are bonded a ring system selected from the group:

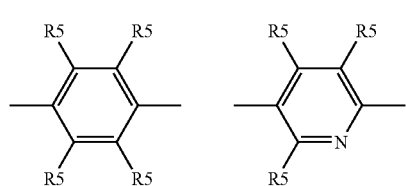

-continued

G, L, R, T and M form a ring system selected from the group:

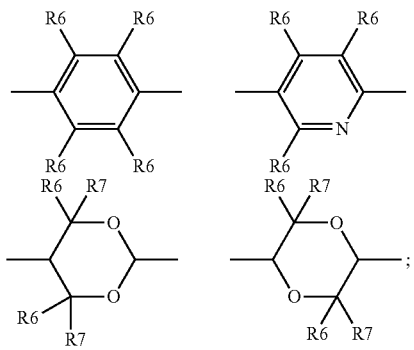

with the proviso that A, B, D, E and G, L, R, T and the C atoms to which they are bonded do not simultaneously form phenyl;

W O, CH$_2$;

Y C(R11a)(R11b)C(R11c)(R11d)C(R11e)(R11f)-, O—C(R11a)(R11b)C(R11c)(R11d)-, —S—C(R11a)(R11b)C(R11c)(R11d)-;

R1 (C$_3$-C$_8$)-alkyl, CF$_3$, phenyl, pyridyl, isoxazolyl, pyrrolidinyl, cyclopentyl, tetrahydrofuranyl, —CH$_2$-phenyl, —CH$_2$-isoxazolyl, —CH$_2$-pyrrolidinyl, —CH$_2$-cyclobutyl or —CH$_2$-cyclopentyl;

where each of the rings may be substituted once or twice by F, Cl, Br, I, OH, CF$_3$, O—(C$_1$-C$_6$)-alkyl (C$_1$-C$_6$)-alkyl, (C$_2$-C$_4$)-haloalkyl, O—(C$_2$-C$_4$)-haloalkyl, N(R11)(R12), CO(R19), (CR20R21)$_x$-O(R22), O—CO—N(R23)(R24);

x 0, 1, 2, 3;

R11a, R11b, R11, R11d, R11e, R11f
independently of one another hydrogen, methyl;

R11, R12, R19, R20, R21, R22, R23, R24
independently of one another hydrogen, (C$_1$-C$_6$)-alkyl;

R2 —CO—R4, —CO—O—R4;

R3 hydrogen, (C$_1$-C$_6$)-alkyl;

R4 methyl;

R5 independently of one another hydrogen, (C$_1$-C$_6$)-alkyl, F, Cl, Br, I, OH, CF$_3$, O—(C$_1$-C$_6$)-alkyl, N(R59)(R60), COO—(C$_1$-C$_6$)-alkyl, CO(R67);

R6, R7 independently of one another hydrogen, (C$_1$-C$_6$)-alkyl, F, Cl, Br, I, OH, CF$_3$, O—(C$_1$-C$_6$)-alkyl, N(R75)(R76), COO—(C$_1$-C$_6$)-alkyl, CO(R83);

R59, R60, R67, R75, R76, R83
independently of one another hydrogen, (C$_1$-C$_6$)-alkyl;

and the pharmaceutically acceptable salts thereof.

A further preferred embodiment of the invention are compounds of the formula I in which G, L, R, T are independently of one another =C(R6)-, —C(R6)(R7)-, =N—, —N(R8)- or O, where not more than two of the radicals G, L, R, T may have the meaning of =N—, —N(R8)- or O;

with the proviso that A, B, D, E and G, L, R, T and the C atoms to which they are bonded do not simultaneously form phenyl and do not simultaneously form pyridine.

A further preferred embodiment of the invention are compounds of the formula I, in which
Y is —CH$_2$—CH$_2$—CH(CH$_3$)—, —O—CH$_2$—CH(CH$_3$)— or CH=CH—CH(CH$_3$)—.

A further preferred embodiment of the invention are compounds of the formula I, in which
W is O.

A further preferred embodiment of the invention are compounds of the formula Ia

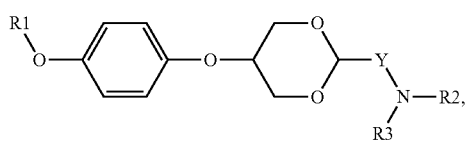

in which the symbols have the meanings mentioned above.

A further preferred embodiment of the invention are compounds of the formula Ib

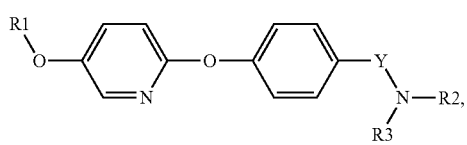

in which the other symbols have the meanings mentioned above.

A further preferred embodiment of the invention are compounds of the formula Ic

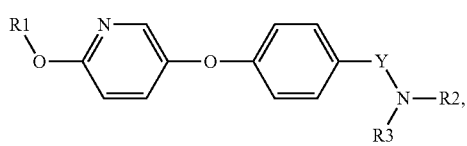

in which the other symbols have the meanings mentioned above.

A further preferred embodiment of the invention are compounds of the formula Id

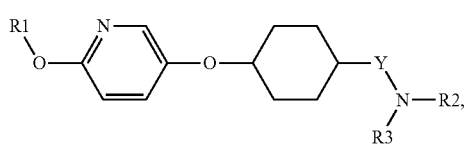

in which the other symbols have the meanings mentioned above.

A further preferred embodiment of the invention are compounds of the formula I in which
R2 is CO—CH$_3$;
R3 is hydrogen.

The alkyl, alkenyl and alkynyl radicals in the substituents R1, R2, R3, R3a, R4, R5, R6, R7, R8, R9, R10, R10a, R10b, R11, R11a, R11b, R11c, R11d, R11e, R11f, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92, R93 may be either straight-chain or branched.

This also applies if the alkyl, alkenyl and alkynyl radicals are part of another group, e.g. part of an alkoxy group (such as (C$_1$-C$_4$)-alkoxy-(C$_1$-C$_4$)-alkyl)).

Examples of alkyl groups are: methyl, ethyl, propyl, butyl, pentyl, hexyl, heptyl and octyl. Included therein are both the n isomers of these radicals and branched isomers such as isopropyl, isobutyl, isopentyl, sec-butyl, tert-butyl, neopentyl, 3,3-dimethylbutyl etc.

Haloalkyl refers to alkyls as defined above in which one, more than one or all hydrogen atoms are replaced by a halogen atom.

Suitable halogens are fluorine, chlorine, bromine and iodine, preferably fluorine, chlorine and bromine, particularly preferably fluorine.

Examples of alkyl groups substituted by halogen are fluorinated alkyl groups such as CF$_3$, CHF$_2$, CH$_2$F, 3-fluoroprop-1-yl, 2,2,1,1-tetrafluoroethyl. It is possible in this case for the additional substituents to occur in any position of the alkyl radical.

Cycloalkyl means in the context of the present application cycloalkyl and cycloalkyl-alkyl (alkyl which is in turn substituted by cycloalkyl), with cycloalkyl having at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as mentioned by way of example above for the alkyl radicals. The cycloalkyl radicals are—unless defined otherwise—preferably unsubstituted. (C$_3$-C$_8$)-Cycloalkyl is a monocyclic, (C$_3$-C$_{12}$)-cycloalkyl includes mono-, bi- and tricyclic ring systems.

Examples of alkenyl and alkynyl groups are: vinyl, 1-propenyl, 2-propenyl(allyl), 2-butenyl, 2-methyl-2-propenyl, 3-methyl-2-butenyl, ethynyl, 2-propynyl(propargyl), 2-butynyl or 3-butynyl.

Cycloalkenyl means in the context of the present application cycloalkenyl radicals and cycloalkenyl-alkyl radicals (alkyl which is substituted by cycloalkenyl), which comprise at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or unconjugated double bonds (that is also alk-dienyl and alk-trienyl radicals), preferably one double bond in a straight or branched chain. The same applies to the triple bonds for alkynyl radicals. The alkenyl and alkynyl radicals may be unsubstituted or optionally substituted by one or more further radicals as mentioned by way of example above for the alkyl radicals. The alkenyl and alkynyl radicals are—unless defined otherwise—preferably unsubstituted.

Aryl refers in the present invention to radicals derived from monocyclic or bicyclic aromatic compounds comprising no ring heteroatoms. Where aryl refers to systems which are not monocyclic, the saturated form (perhydroform) or the partly unsaturated form (for example the dihydro form or tetrahydro form) is also possible for the second ring when their respective forms are known and stable. The term aryl also includes in the present invention for example bicyclic radicals in which both rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl. The aryl radicals are—unless defined otherwise—preferably unsubstituted. Aryl is particularly preferably phenyl or naphthyl. Phenyl is very particularly preferred.

Heterocycle is a mono- or bicyclic ring system having 5 to 12 ring members, in which at least one atom in the ring system is a heteroatom from the series N, O and S. Also included in this definition are ring systems in which the heterocycle is fused to a benzene nucleus. $(C_3-C_8)$-Heterocycle is a monocyclic, $(C_3-C_{12})$-heterocycle includes mono- and bicyclic ring systems.

Heteroaryl is a subgroup of heterocycle and is a mono- or bicyclic aromatic ring system having 5 to 12 ring members, in which at least one atom in the ring system is a heteroatom from the series N, O and S.

Suitable "heterocyclic rings" or "heterocyclic radicals" are azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, meaning for example 1-oxy-2-, 3- or 4-pyridyl.

Heteroaryl radicals mean radicals derived from monocyclic or bicyclic aromatic compounds which comprise ring heteroatoms, preferably N, O or S. $(C_3-C_8)$-Heteroaryl is a monocyclic, $(C_3-C_{12})$-heteroaryl includes mono- and bicyclic ring systems. Otherwise, the statements made about aryl radicals apply to heteroaryl radicals.

A "tricycle" means structures having 3 rings which are linked together by more than one bond. Examples of such systems are fused systems having 3 rings and spirocycles with fused-on ring system.

A polycyclic group (bi-, tri- or spirocyclic ring structure) means in the context of the present application a group derived from spiranes, fused ring systems or bridged ring systems. The spiranes are notable for two rings having only one carbon atom in common and the ring planes of the two rings being perpendicular to one another. In the fused ring systems, two rings are linked together in such a way that they have two atoms in common. This type of linkage involves an "ortho fusion". Bridged ring systems are ring systems having a bridge of carbon atoms and/or heteroatoms between two nonadjacent atoms of a ring.

A "chemically reasonable radical" means in the context of the present invention a radical which is stable at room temperature and atmospheric pressure. In the context of the present invention, a "chemically reasonable radical" in the definition of group A in the compounds of the formula I means groups which have no heteroatom-heteroatom bonds between the individual members of the groups.

A "nonaromatic" ring means in the context of the present application preferably a ring which is saturated or partly unsaturated. In this connection, a partly unsaturated ring according to the present application has one or, where appropriate, a plurality of double bonds, but the partly unsaturated ring is nonaromatic. The term "nonaromatic" in the context of the present application also includes "nonheteroaromatic" rings.

The compounds of the formula I may comprise one or more centers of assymetry. The compounds of the formula I may therefore be in the form of their racemates, enantiomer-enriched mixtures, pure enantiomers, diastereomers and diastereomer mixtures. The present invention encompasses all these isomeric forms of the compounds of the formula I. These isomeric forms may be obtained by known methods, even if not expressly described in some cases, such as, for example, separation of the mixtures by chromatographic means.

The present invention encompasses all possible tautomeric forms of the compounds of the formula I.

The present invention further encompasses derivatives of the compounds of the formula I, for example solvates, such as hydrates and alcohol adducts, esters, prodrugs and other physiologically acceptable derivatives of the compounds of the formula I, and active metabolites of the compounds of the formula I. The invention likewise encompasses all crystal modifications of the compounds of the formula I.

If radicals or substituents can occur more than once in the compounds of the formula I (such as, for example, "R5"), they may all have the expected meanings independently of one another and be identical or different.

Physiologically tolerated salts are, because their solubility in water is greater than that of the initial or basic compounds, particularly suitable for medical applications. These salts must have a physiologically tolerated anion or cation. Suitable physiologically tolerated acid addition salts of the compounds of the invention are salts of inorganic acids such as hydrochloric acid, hydrobromic, phosphoric, metaphosphoric, nitric, sulfonic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids. The chlorine salt is particularly preferably used for medical purposes. Suitable physiologically tolerated basic salts are ammonium salts, alkali metal salts (such as sodium and potassium salts), alkaline earth metal salts (such as magnesium and calcium salts), zinc salts, and salts of trometamol(2-amino-2-hydroxymethyl-1,3-propanediol), diethanolamine, lysine, arginine, choline, meglumine or ethylenediamine.

Salts with a physiologically nontolerated anion or cation likewise belong within the framework of the invention as useful intermediates for the preparation or purification of physiologically tolerated salts and/or for use in nontherapeutic, for example in vitro, applications.

A further aspect of this invention are prodrugs of the compounds of the invention. Such prodrugs can be metabolized in vivo to a compound of the invention. These prodrugs may themselves be active or not.

The compounds of the invention may also exist in various polymorphous forms, e.g. as amorphous and crystalline polymorphous forms. All polymorphous forms of the compounds of the invention belong within the framework of the invention and they are a further aspect of the invention.

All references hereinafter to "compound(s) of formula (I)" refer to compound(s) of the formula (I) as described above, and the salts thereof and as described herein.

The compounds of the formula I and the physiologically tolerated salts and physiologically functional derivatives thereof represent ideal medicaments for the treatment of elevated lipid concentrations in the blood and in tissues, the metabolic syndrome, obesity, diabetes, insulin resistance, dysregulation of LDL, HLD and VLDL or cardiovascular disorders, lipid metabolism impairments, in particular hyperlipidemia.

The compound(s) of the formula (I) can also be administered in combination with further active ingredients.

The amount of a compound of formula (I) necessary to achieve the desired biological effect depends on a number of factors, for example the specific compound chosen, the intended use, the mode of administration and the clinical condition of the patient. The daily dose is generally in the range from 0.1 mg to 100 mg (typically from 0.1 mg to 50 mg) per day and per kilogram of body weight, for example 0.1-10 mg/kg/day. Tablets or capsules may contain, for example, from 0.01 to 100 mg, typically from 0.02 to 50 mg. For the prophylaxis or therapy of the abovementioned conditions, the compounds of formula (I) may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral and peroral (for example sublingual) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinal acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contains a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine.

Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Combinations with Other Medicaments

The compounds of the invention can be administered alone or in combination with one or more further pharmacologically active substances which have for example beneficial effects on metabolic disturbances or disorders frequently associated therewith.

Examples of such medicaments are
1. medicaments which lower blood glucose, antidiabetics,
2. active ingredients for the treatment of dyslipidemias,
3. antiatherosclerotic medicaments,
4. antiobesity agents,
5. anti-inflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

The active ingredients mentioned below may be mentioned by way of example as suitable for combination products:

All antidiabetics which are mentioned in the Rote Liste 2005, chapter 12; all weight-reducing agents/appetite suppressants which are mentioned in the Rote Liste 2005, chapter 1; all lipid-lowering agents which are mentioned in the Rote Liste 2005, chapter 58. They can be combined with the compound of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or Levemir® (insulin detemir) or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1-derivatives and GLP-1 agonists such as, for example, exenatide, liraglutide or those which have been disclosed in WO98/08871, WO2005027978, WO2006037811, WO2006037810 of Novo Nordisk A/S, in WO01/04156 of Zealand or in WO00/34331 of Beaufour-Ipsen, pramlintide acetate (Symlin; Amylin Pharmaceuticals), BIM-51077, PC-DAC:exendin-4 (an exendin-4 analog covalently bonded to recombinant human albumin), agonists like those described for example in D. Chen et al., Proc. Natl. Acad. Sci. USA 104 (2007) 943, those described in WO2006124529 and orally effective hypoglycemic active ingredients.

Antidiabetics also include agonists of the glucose-dependent insulinotropic polypeptide (GIP) receptor as described for example in WO2006121860.

The orally effective hypoglycemic active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose 1,6-bisphosphatase
modulators of glucose transporter 4 (GLUT4),
inhibitors of glutamine-fructose-6-phosphate amidotransferase (GFAT),
GLP-1 agonists,
potassium channel openers such as, for example, pinacidil, cromakalim, diazoxide or those as described in R. D. Carr et al., Diabetes 52, 2003, 2513.2518, in J. B. Hansen et al, Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 of Novo Nordisk NS,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption, inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG) or as described in WO2004097655, WO2004000805, WO2004000804, WO2004000803, WO2002050068, WO2002050060, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163.

In one embodiment of the invention, the compound of the formula I is administered in combination with Vytorin™, a fixed combination of ezetimibe with simvastatin.

In one embodiment of the invention, the compound of the formula I is administered in combination with a fixed combination of ezetimibe with atorvastatin.

In one embodiment of the invention, the compound of the formula I is administered in combination with a fixed combination of ezetimibe with fenofibrate.

In one embodiment of the invention, the compound of the formula I is administered in combination with a fixed combination of fenofibrate with rosuvastatin.

In a further embodiment of the invention, the compound of the formula I is administered in combination with a fixed combination of fenofibrate with metformin.

In one embodiment of the invention, the compound of the formula I is administered in combination with ISIS-301012, an antisense oligonucleotide able to regulate the apolipoprotein B gene.

In one embodiment of the invention, the compound of the formula I is administered in combination with a PPAR gamma agonist such as, for example, rosiglitazone, pioglitazone, JTT-501, GI 262570, R-483, CS-011 (rivoglitazone).

In one embodiment of the invention, the compound of the formula I is administered in combination with Competact™, a fixed combination of pioglitazone hydrochloride with metformin hydrochloride.

In one embodiment of the invention, the compound of the formula I is administered in combination with Tandemact™, a fixed combination of pioglitazone with glimepride.

In a further embodiment of the invention, the compound of the formula I is administered in combination with a fixed combination of pioglitazone hydrochloride with an angiotensin II antagonist such as, for example, TAK-536.

In one embodiment of the invention, the compound of the formula I is administered in combination with a PPAR alpha agonist such as, for example, GW9578, GW-590735, K-111, LY-674, KRP-101, DRF-10945, LY-518674 or those described in WO2001040207, WO2002096894, WO2005097076.

In one embodiment of the invention, the compound of the formula I is administered in combination with a mixed PPAR alpha/gamma agonist such as, for example, naveglitazar, LY-510929, ONO-5129, E-3030, AVE 8042, AVE 8134, AVE 0847, CKD-501 (lobeglitazone sulfate) or as described in WO 00/64888, WO 00/64876, WO03/020269 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516 or as described in WO2006059744, WO2006084176, WO2006029699, WO2007039172-WO2007039178.

In one embodiment, the compound of the formula I is administered in combination with metaglidasen or with MBX-2044 or other partial PPAR gamma agonists/antagonists. In one embodiment of the invention, the compound of the formula I is administered in combination with a fibrate such as, for example, fenofibrate, clofibrate, bezafibrate.

In one embodiment of the invention, the compound of the formula I is administered in combination with an MTP inhibitor such as, for example, implitapide, BMS-201038, R-103757, AS-1552133 or those described in WO2005085226, WO2005121091, WO2006010423.

In one embodiment of the invention, the compound of the formula I is administered in combination with a CETP inhibitor such as, for example, torcetrapib or JTT-705 or those described in WO2006002342, WO2006010422, WO2006012093, WO2006073973, WO2006072362, WO2006097169, WO2007041494.

In one embodiment of the invention, the compound of the formula I is administered in combination with a bile acid absorption inhibitor (see, for example, U.S. Pat. No. 6,245, 744, U.S. Pat. No. 6,221,897 or WO00/61568), such as, for example, HMR 1741 or those as described in DE 10 2005 033099.1 and DE 10 2005 033100.9, WO2007009655-56.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586, or those as described in WO2005097738.

In one embodiment of the invention, the compound of the formula I is administered in combination with an ABCA1 expression enhancer as described for example in WO2006072393.

In a further embodiment of the invention, the compound of the formula I is administered in combination with an RNAi therapeutic directed against PCSK9 (proprotein convertase subtilisin/kexin type 9).

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe or SMP-797.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494, TAK-475 or as described in WO2005077907, JP2007022943.

In one embodiment of the invention, the compound of the formula I is administered in combination with a lipoprotein (a) antagonist such as, for example, gemcabene (CI-1027).

In one embodiment of the invention, the compound of the formula I is administered in combination with an agonist of GPR109A (HM74A receptor agonist; NAR agonist (nicotinic acid receptor agonist)) such as, for example, nicotinic acid or extended release niacin in conjunction with MK-0524A or the compounds described in WO2006045565, WO2006045564, WO2006069242, WO2006124490, WO2006113150, WO2007017261, WO2007017262, WO2007017265, WO2007015744, WO2007027532.

In another embodiment of the invention, the compound of the formula I is administered in combination with an agonist of GPR116 as described for example in WO2006067531, WO2006067532.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment, the compound of the formula I is administered in combination with a sulfonylurea such as, for example, tolbutamide, glibenclamide, glipizide, gliclazide or glimepiride.

In one embodiment, the compound of the formula I is administered in combination with a substance which enhances insulin secretion, such as, for example, KCP-265 (WO2003097064) or those described in WO2007026761.

In one embodiment, the compound of the formula I is administered in combination with agonists of the glucose-dependent insulinotropic receptor (GDIR), such as, for example, APD-668.

In one embodiment, the compound of the formula I is administered in combination with a biguanide such as, for example, metformin.

In another embodiment, the compound of the formula I is administered in combination with a meglitinide such as, for example, repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In one embodiment, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4[(3,4-dihydro-3-methyl-4-oxo-2-quinazolinyl-methoxy]phenyl]methyl]-2,4-thiazolidinedione.

In one embodiment, the compound of the formula I is administered in combination with an α-glucosidase inhibitor such as, for example, miglitol or acarbose.

In one embodiment, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, such as, for example, PSN-357 or FR-258900 or those as described in WO2003084922, WO2004007455, WO2005073229-31 or WO2005067932.

In one embodiment, the compound of the formula I is administered in combination with glucagon receptor antagonists such as, for example, A-770077 or NNC-25-2504 or as described in WO2004100875 or WO2005065680.

In one embodiment, the compound of the formula I is administered in combination with activators of glucokinase, such as, for example, LY-2121260 (WO2004063179), PSN-105, PSN-110, GKA-50 or those as are described for example in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847.

In one embodiment, the compound of the formula I is administered in combination with an inhibitor of gluconeogenesis, such as, for example, FR-225654.

In one embodiment, the compound of the formula I is administered in combination with inhibitors of fructose-1,6-bisphosphatase (FBPase), such as, for example, CS-917 (MB-06322) or MB-07803 or those described in WO2006023515, WO2006104030, WO2007014619.

In one embodiment, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, the compound of the formula I is administered in combination with inhibitors of glutamine-fructose-6-phosphate amidotransferase (GFAT), as are described for example in WO2004101528.

In one embodiment, the compound of the formula I is administered in combination with inhibitors of dipeptidylpeptidase IV (DPP-IV), such as, for example, vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200, GW-825964X, KRP-104, DP-893, ABT-341, ABT-279 or another salt thereof, or the compounds described in WO2003074500, WO2003106456, WO2004037169, WO200450658, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006090915, WO2006104356, WO2006127530, WO2006111261, WO2007015767, WO2007024993, WO2007029086.

In one embodiment, the compound of the formula I is administered in combination with Janumet™, a fixed combination of sitagliptin phosphate with metformin hydrochloride.

In one embodiment, the compound of the formula I is administered in combination with inhibitors of 11-beta-hydroxysteroid dehydrogenase 1 (11β-HSD1), such as, for example, BVT-2733, JNJ-25918646, INCB-13739 or those as are described for example in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138695, WO2006133926, WO2007003521, WO2007007688, US2007066584, WO2007047625, WO2007051811, WO2007051810.

In one embodiment, the compound of the formula I is administered in combination with inhibitors of protein tyrosine phosphatase 1B (PTP1B), as are described for example in WO200119830-31, WO200117516, WO2004506446, WO2005012295, WO2005116003, WO2005116003, WO2006007959, DE 10 2004 060542.4, WO2007009911, WO2007028145, WO2007081755.

In one embodiment, the compound of the formula I is administered in combination with modulators of the sodium-dependent glucose transporter 1 or 2 (SGLT1, SGLT2), such as, for example, KGA-2727, T-1095, SGL-0010, AVE 2268, SAR 7226 dapagliflozin and sergliflozin or as are described for example in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170 or by A. L. Handlon in Expert Opin. Ther. Patents (2005) 15(11), 1531-1540.

In one embodiment, the compound of the formula I is administered in combination with modulators of GPR40 as described for example in WO2007013689, WO2007033002.

In one embodiment, the compound of the formula I is administered in combination with modulators of GPR119b as described for example in WO2004041274.

In one embodiment, the compound of the formula I is administered in combination with modulators of GPR119 as described for example in WO2005061489 (PSN-632408), WO2004065380, WO2007003960-62 and WO2007003964.

In a further embodiment, the compound of the formula I is administered in combination with modulators of GPR120.

In one embodiment, the compound of the formula I is administered in combination with inhibitors of hormone-sensitive lipase (HSL) and/or phospholipases as described for example in WO2004035550, WO2005073199, WO2006074957, WO2006087309, WO2006111321, WO2006131233, WO2006131232, WO2006131231, WO2007042178, WO2007045392.

In one embodiment, the compound of the formula I is administered in combination with inhibitors of endothelial lipase (EL) and/or phospholipases as described for example in WO2006111321, WO2006131233, WO2006131232, WO2006131231, WO2007042178, WO2007045392, WO2007045393, WO2007110216, WO2007110215.

In one embodiment, the compound of the formula I is administered in combination with inhibitors of acetyl-CoA carboxylase (ACC), such as, for example, those as described in WO199946262, WO200372197, WO2003072197, WO2005044814, WO2005108370, JP2006131559, WO2007011809, WO2007011811, WO2007013691.

In a further embodiment, the compound of the formula I is administered in combination with modulators of xanthine oxidoreductase (XOR).

In one embodiment of the invention, the compound of the formula I is administered in combination with an inhibitor of phosphoenolpyruvate carboxykinase (PEPCK), such as, for example, those as described in WO2004074288.

In one embodiment of the invention, the compound of the formula I is administered in combination with an inhibitor of glycogen synthase kinase 3 beta (GSK-3 beta), as described for example in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, the compound of the formula I is administered in combination with an inhibitor of the serum/glucocorticoid-regulated kinase (SGK) as described for example in WO2006072354.

In one embodiment, the compound of the formula I is administered in combination with an agonist of the RUP3 receptor as described for example in WO2007035355.

In one embodiment, the compound of the formula I is administered in combination with an inhibitor of protein kinase C beta (PKC beta), such as, for example, ruboxistaurin. In another embodiment, the compound of the formula I is administered in combination with an activator of the gene which codes for the ataxia telangiectasia mutated (ATM) protein kinase, such as, for example, chloroquine.

In one embodiment, the compound of the formula I is administered in combination with an endothelin A receptor antagonist such as, for example, avosentan (SPP-301).

In one embodiment, the compound of the formula I is administered in combination with inhibitors of "I-kappaB kinase" (IKK inhibitors), as are described for example in WO2001000610, WO2001030774, WO2004022553 or WO2005097129.

In one embodiment, the compound of the formula I is administered in combination with modulators of the glucocorticoid receptor (GR), like those described for example in WO2005090336, WO2006071609, WO2006135826.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);
NPY antagonists such as, for example, naphthalene-1-sulfonic acid {4-[(4-aminoquinazolin-2-ylamino)methyl]cyclohexylmethyl}amide hydrochloride (CGP 71683A);
NPY-5 receptor antagonists such as L-152804 or such as, for example as in WO2006001318;
NPY-4 receptor antagonists such as, for example in WO2007038942;
NPY-2 receptor antagonists such as, for example in WO02007038943;
peptide YY 3-36 (PYY3-36) or analogous compounds, such as, for example, CJC-1682 (PYY3-36 conjugated with human serum albumin via Cys34) or CJC-1643 (derivative of PYY3-36 which conjugates in vivo to serum albumin) or those as are described in WO2005080424, WO2006095166; derivatives of the peptide obestatin such as those described in WO2006096847; CB1 R (cannabinoid receptor 1) antagonists (such as, for example, rimonabant, SR147778, SLV-319, AVE-1625, MK-0364 or salts thereof or compounds such as those described for example in EP 0656354, WO 00/15609, WO2001/64632-34, WO 02/076949, WO2005080345, WO2005080328, WO2005080343, WO2005075450, WO2005080357, WO200170700, WO2003026647-48, WO200302776, WO2003040107, WO2003007887, WO2003027069, U. S. Pat. No. 6,509,367, W0200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, W0200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007016460, WO2007020502, WO2007026215, WO2007028849, WO2007031720, WO2007031721, WO2007036945, WO2007038045, WO2007039740, US20070015810, WO2007046548, WO2007047737, WO2007084319, WO02007084450);
cannabinoid receptor 1/cannabinoid receptor 2 (CB1/CB2) modulating compounds as described for example in WO2007001939, WO2007044215, WO2007047737;
MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052;
orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403, WO2005075458, WO200667224);

histamine H3 receptor agonists (e.g. 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893, WO2006107661, WO2007003804, WO2007016496, WO2007020213);

histamine H1/histamine H3 modulators such as, for example, betahistine or its dihydrochloride;

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoreceptor such as, for example, 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as are described in JP2006111553, WO2002038543, WO2007048840-843;

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or those compounds such as are described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, WO2007093363, WO2007093364, WO2007093365, WO2007093366, US2007093508, US2007093509, WO2007048802, JP2007091649);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180) or those as are described in WO2005116034;

serotonin reuptake inhibitors (e.g. dexfenfluramine);

mixed serotonin/dopamine reuptake inhibitors (e.g. bupropion) or fixed combinations of bupropion with naltrexone;

mixed serotoninergic and noradrenergic compounds (e.g. WO 00/71549); 5-HT receptor agonists, e.g. 1-(3-ethylbenzofuran-7-yl)piperazine oxalic acid salt (WO 01/09111);

mixed dopamine/norepinephrine/acetylcholine reuptake inhibitors (e.g. tesofensine); 5-HT2C receptor agonists (such as, for example, lorcaserin hydrochloride (APD-356) BVT-933 or those as are described in WO200077010, WO20077001-02, WO2005019180, WO2003064423, WO200242304, WO2005035533, WO2005082859, WO2006077025, WO2006103511);

5-HT6 receptor modulators such as, for example E-6837 or BVT-74316 or those as are described in WO2005058858, WO2007054257;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);

uncoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (like those described for example in WO 00/40569); inhibitors of diacylglycerol O-acyltransferases (DGATs) such as for example BAY-74-4113 or as described for example in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538;

inhibitors of fatty acid synthase (FAS) such as, for example, C75 or those as described in WO2004005277;

inhibitors of stearoyl-CoA delta9 desaturase (SCD1) as described for example in WO2007009236, WO2007044085, WO2007046867, WO2007046868, WO20070501124;

oxyntomodulin;

oleoyl-estrone or thyroid hormone receptor agonists or partial agonists such as, for example: KB-2115 or those as described in WO20058279, WO200172692, WO200194293, WO2003084915, WO2004018421, WO2005092316, WO2007003419, WO2007009913, WO2007039125.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the SIRT1 enzyme.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

FM-VP4
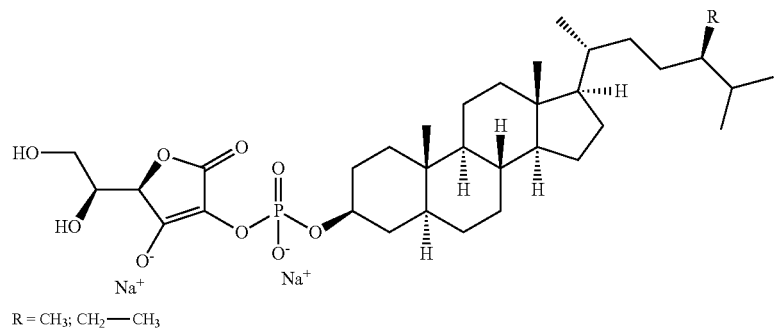
R = CH₃; CH₂—CH₃
JTT-501
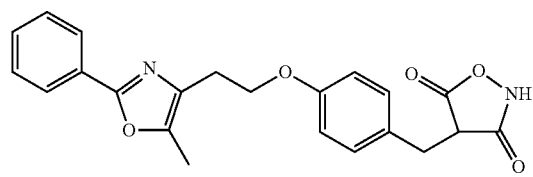
GI 262570
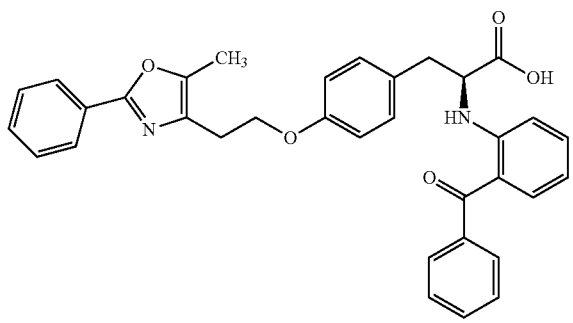
CS-011
Rivoglitazone
GW-9578
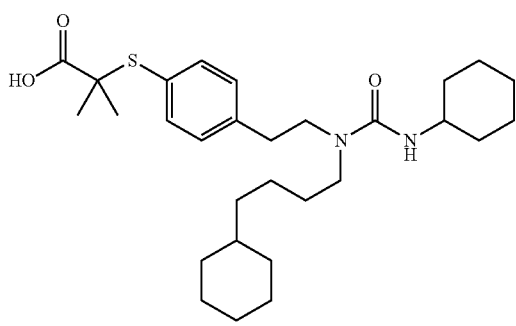
K-111
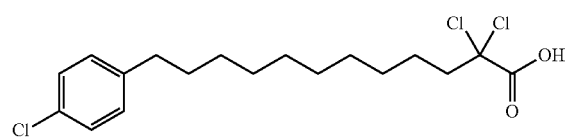
LY-674
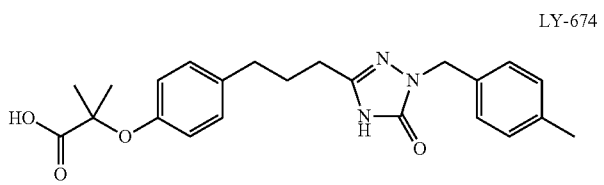
KRP-101
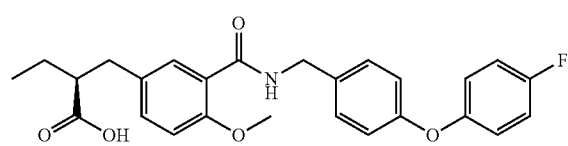
LY-510929
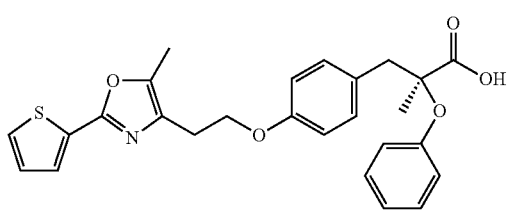

-continued
GW-501516
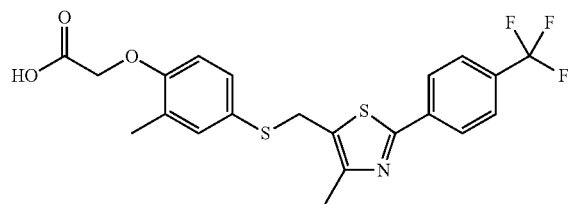
BMS-2011038
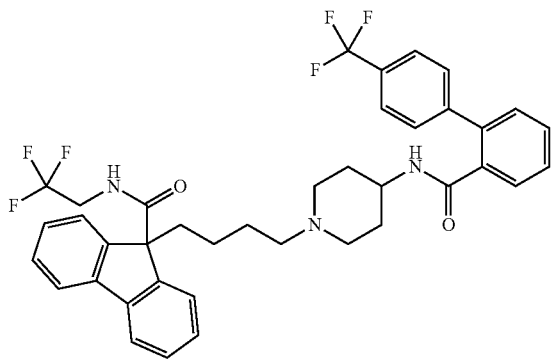
R-103757
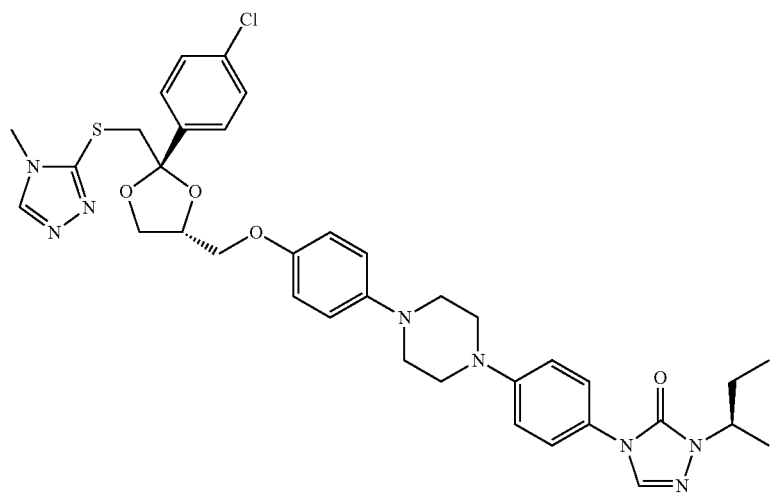
JTT-705
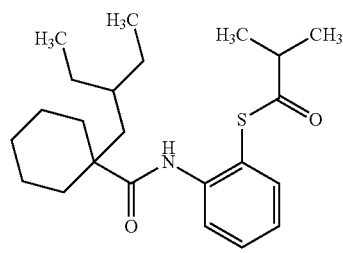
OPC-14117
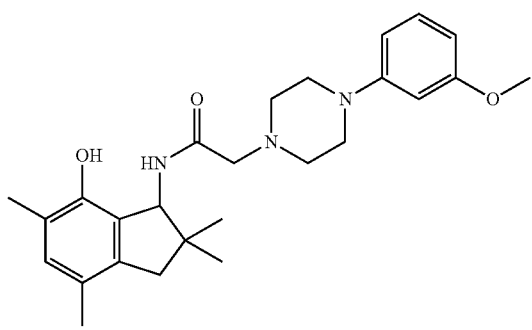
NO-1886
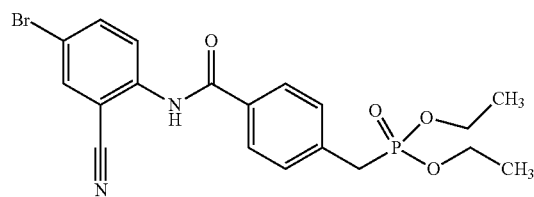
SB-204990
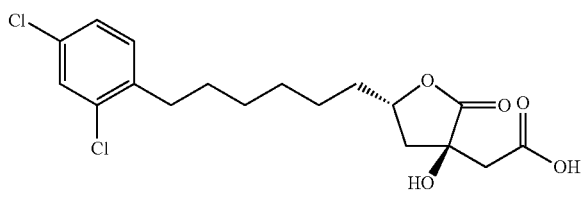

-continued
BMS-188494
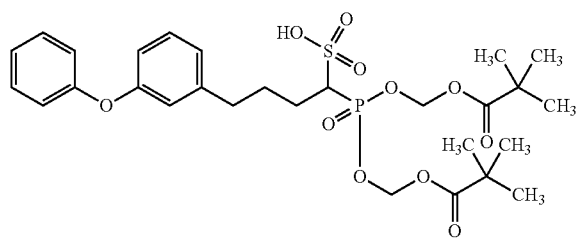
CI-1027
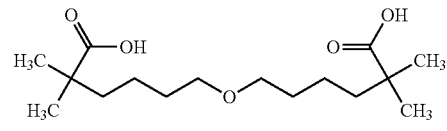
ATL-962
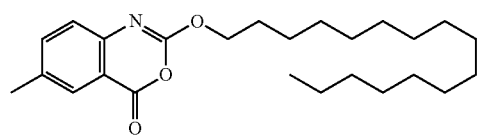
FR-258900
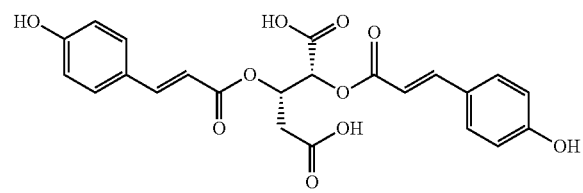
NNC-25-2504
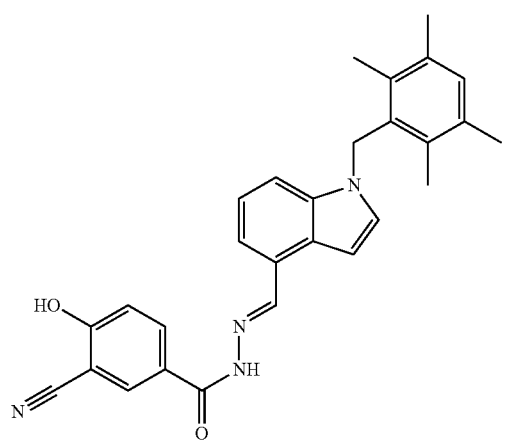
LY-2121260
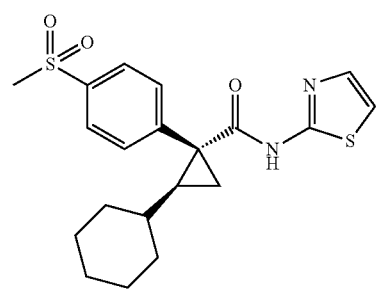
GKA-50
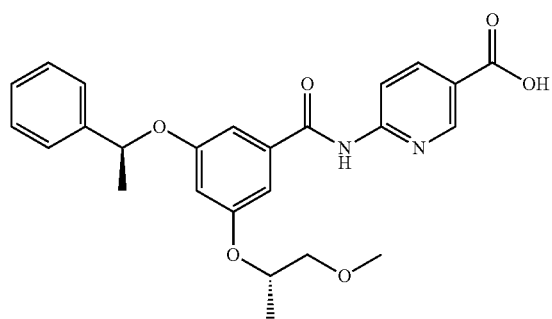
FR-225654
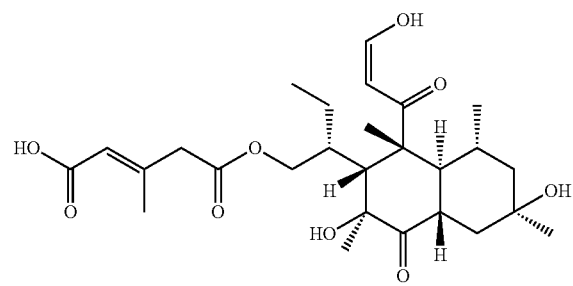
KST-48
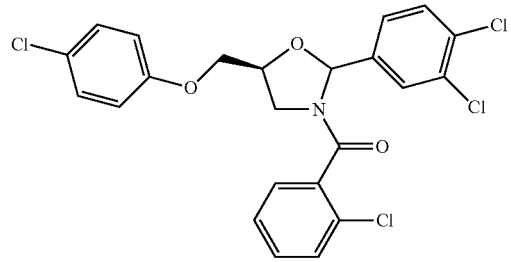
BMS-477118
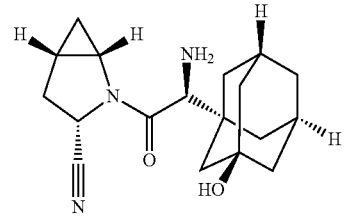

-continued
BVT-2733
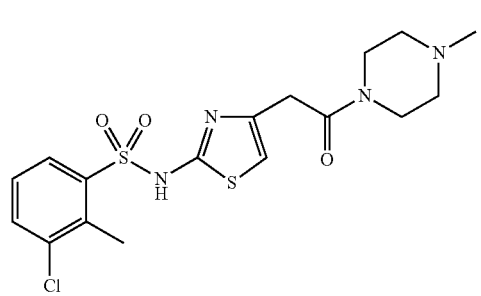
T-1095
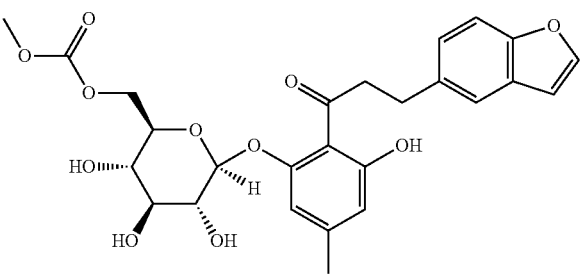
SPP-301
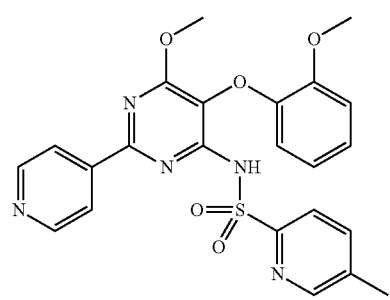
THIQ
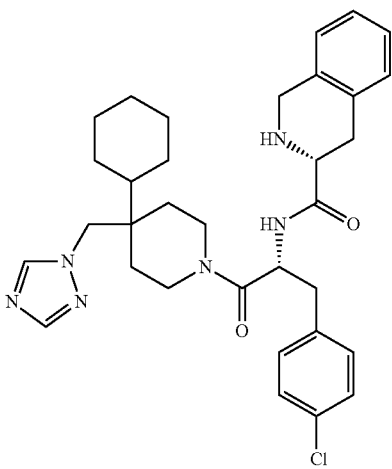
MB243
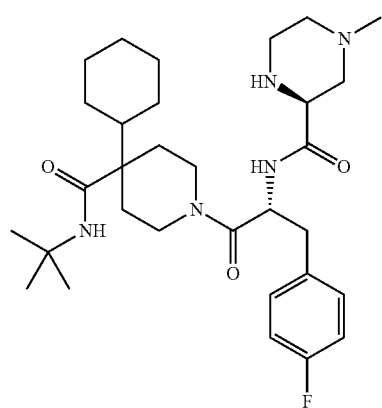
RY764
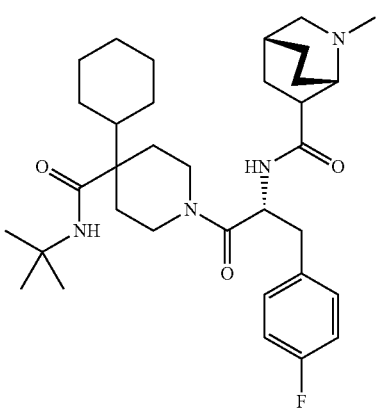
CHIR-785
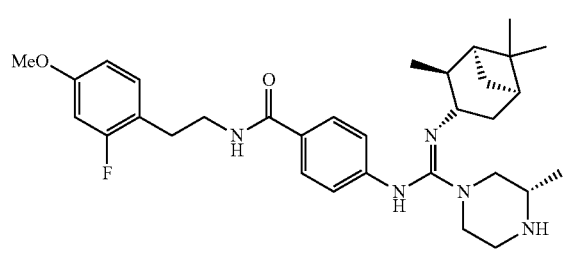
A-761
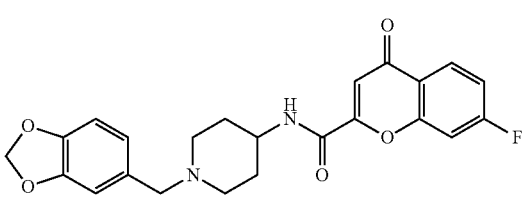

-continued
A-665798
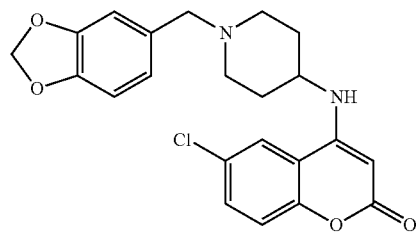
ATC-0175
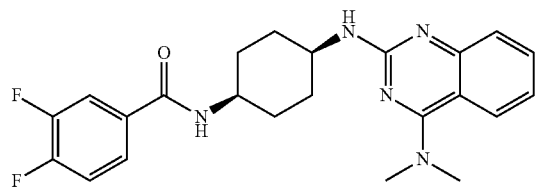
T-226296
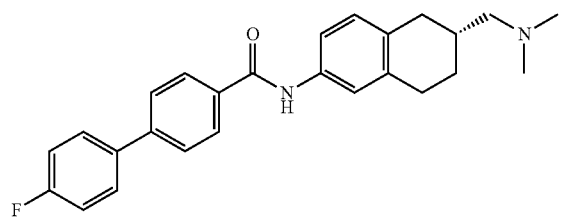
GW-803430
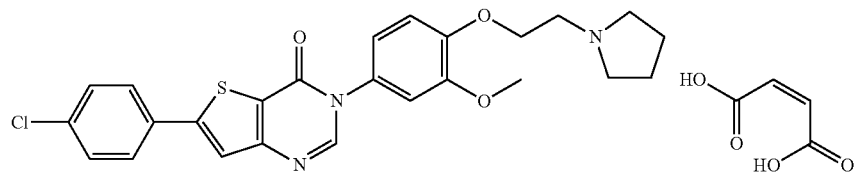
AOD-9604
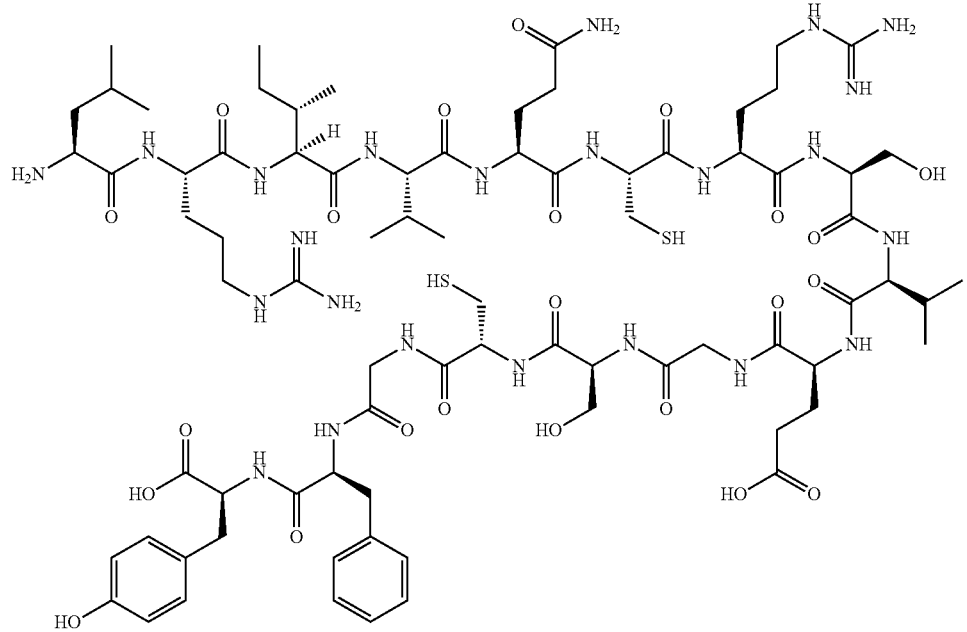
A-778193
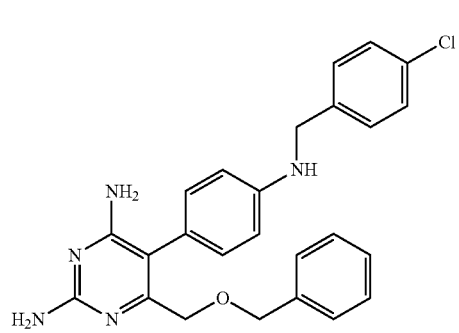
C75
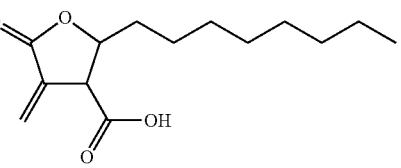

-continued
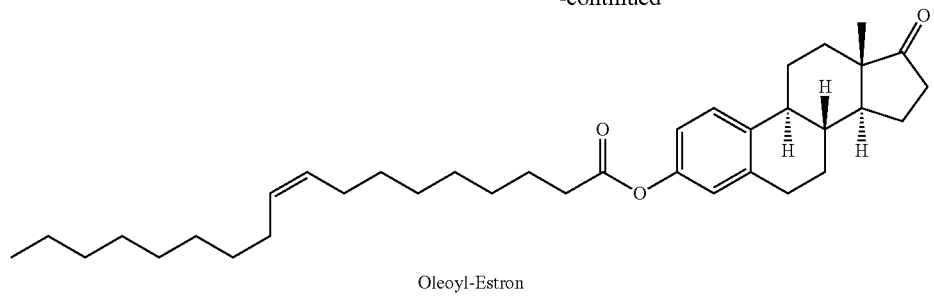
Oleoyl-Estron
KB-2115
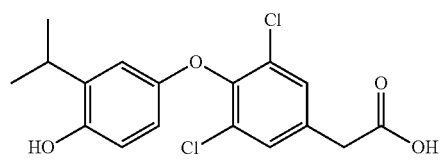
KCP-265
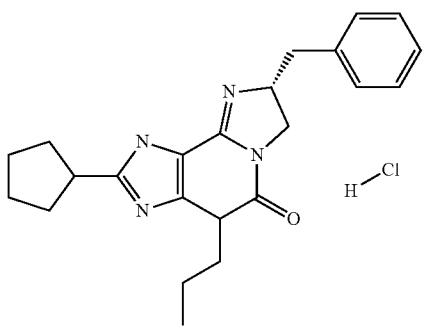
SMP-797
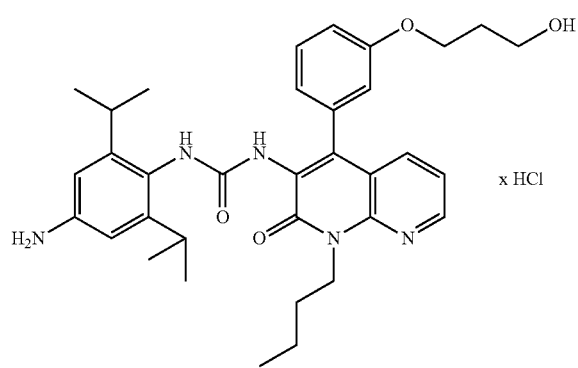
JNJ-25918646
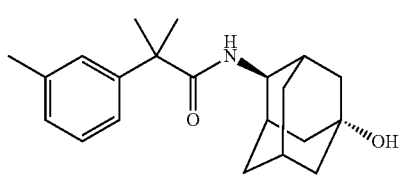
PSN-632408
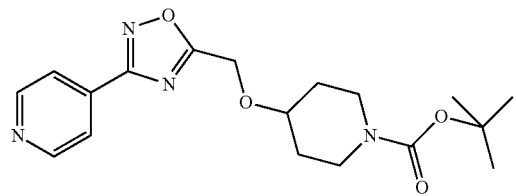
SYR-322
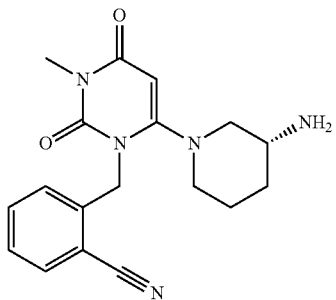
DP-893
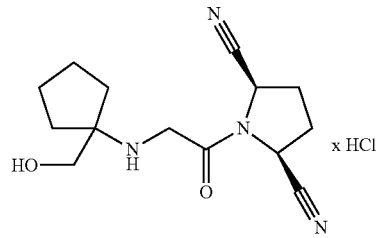
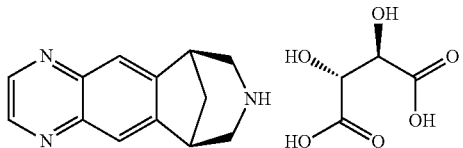
Varenicline Tartrate -continued
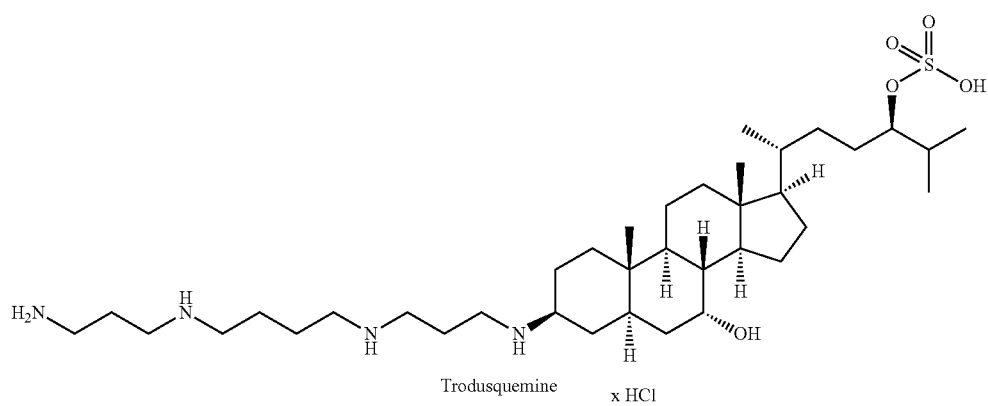
Trodusquemine x HCl
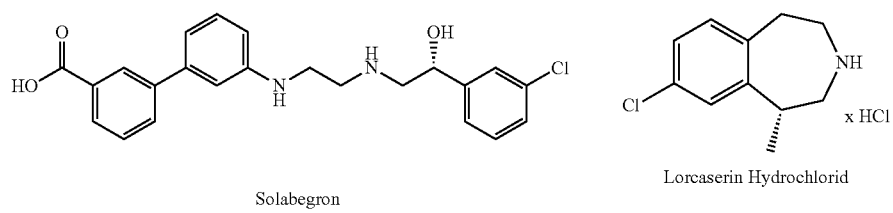
Solabegron
Lorcaserin Hydrochlorid
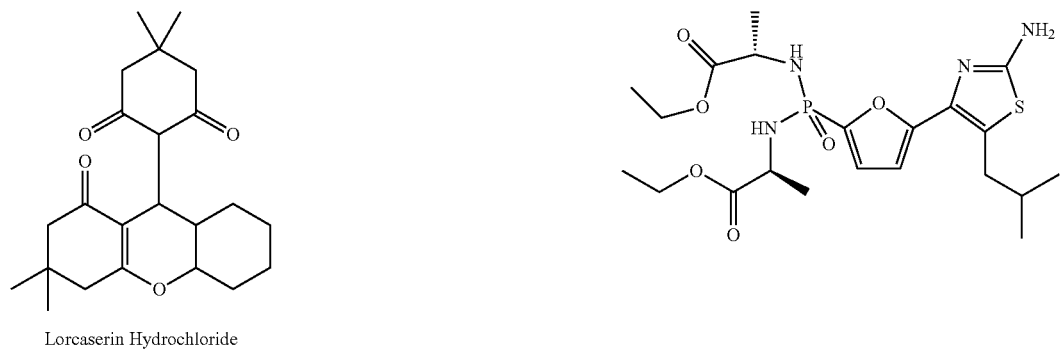
Lorcaserin Hydrochloride
L-152804
MB-06322 CS-917
N-5984
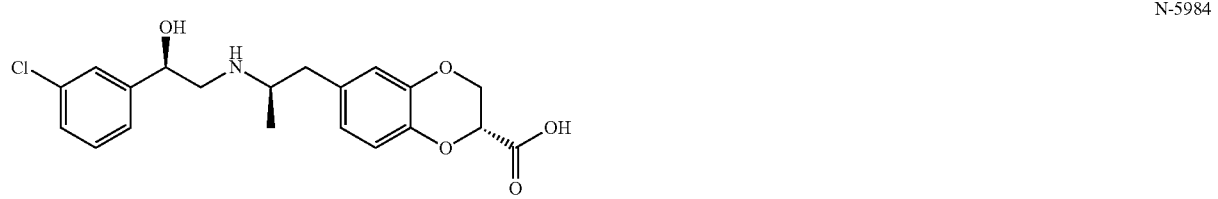
BIM-51077
TAK-536
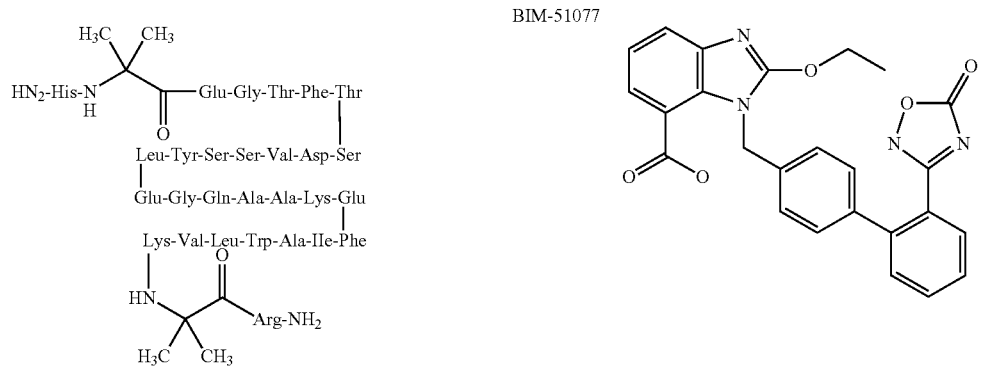

-continued
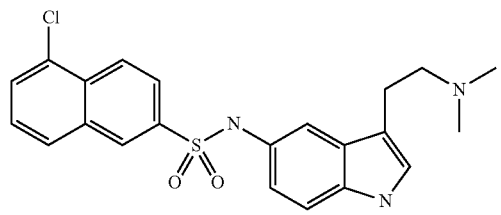
BVT-74316
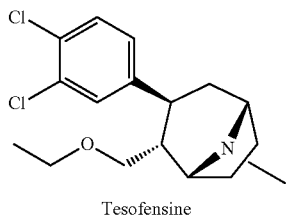
Tesofensine
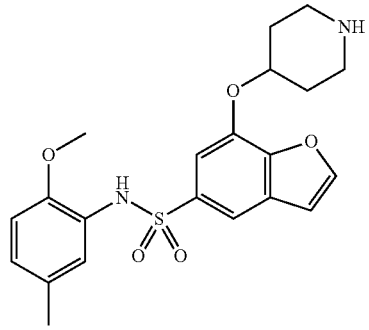
MK-0364
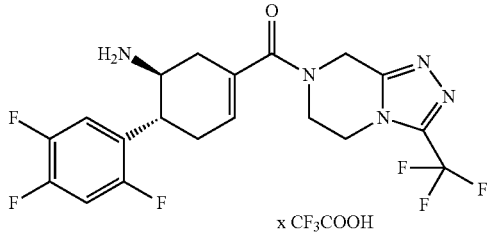
ABT-341
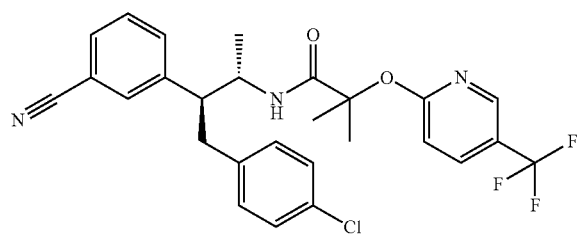
Sergliflozin
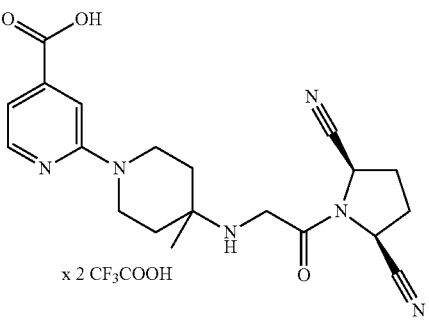
ABT-279
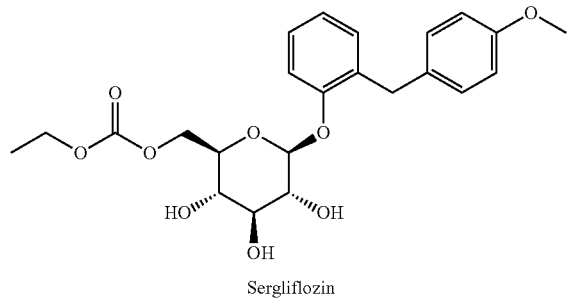
AVE 1625
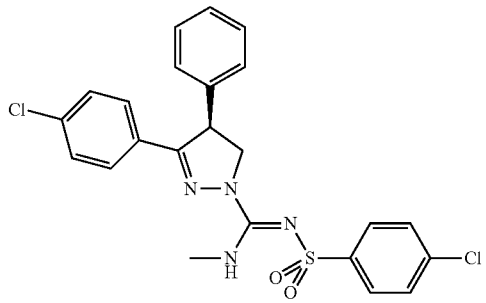
SLV-319
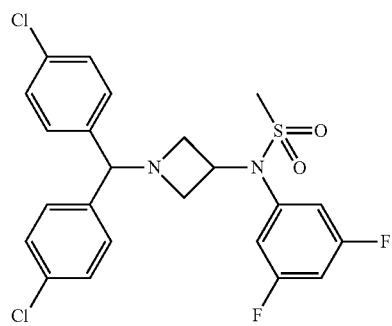
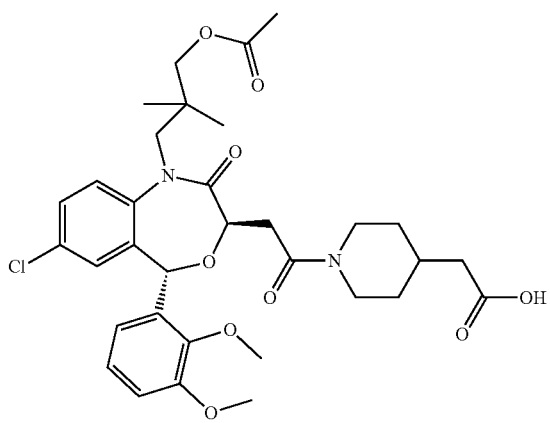
TAK-475

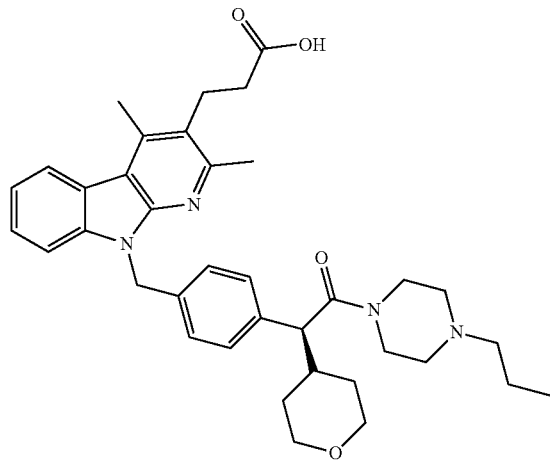

AS-1552133

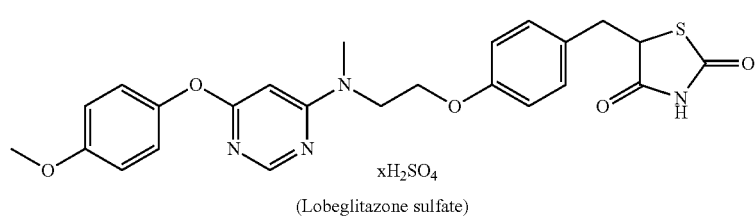

CKD-501

(Lobeglitazone sulfate)

In one embodiment, the compounds of the formula I are administered in combination with medicaments acting on the cardiovascular and circulatory system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an antiinflammatory effect.

In one embodiment, the compounds of the formula I are administered in combination with medicaments employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

Test Models

The activity of the compounds of the invention of the formula I was investigated in the following designs of experiments:

The enzyme acetyl-CoA carboxylase (ACC) catalyzes the ATP-dependent synthesis of malonyl-CoA from acetyl-CoA and $CO_2$. Malonyl-CoA is a precursor for the synthesis of lipids. At the same time, malonyl-CoA allosterically inhibits carnithine pamitoyltransferase 1 (CPT1). CPT1 is involved in the transport of activated fatty acids into the mitochondrion. This step is necessary for degradation of fatty acids in R oxidation (Munday, Biochem. Soc Trans (2002), 30: 1059-1064). Owing to these functions in metabolism, inhibition of ACC leads, through a reduction in the formation of malonyl-CoA, both to a reduction in lipid synthesis and to a degradation of lipids which have already been synthesized. Both mechanisms reduce the amount of intracellularly stored lipids. This correlates with an improvement in insulin resistance in animal models (Savage et al., J Clin Invest (2006), 116: 817-824; Choi et al., Proc Natl Acad Sci USA (2007), 104: 16480-16485). In addition, inhibition of ACC reduces the growth rate of tumor cells (Beckers et al., Cancer Res (2007), 67: 8180-8187). Two isoforms of ACC have been described, ACC1 and ACC2. They differ in their structure, in the intracellular localization and the tissue distribution (Munday, Biochem. Soc. Trans., 30, 1059-1064). Decreasing the activities of both isoforms, but also that of ACC2 alone, in animal models reduces the intracellular lipid content, thus also preventing the development of fatty degeneration of the liver and increasing insulin sensitivity (Abu-Elheiga et al., Science (2001), 291: 2613-2616, Savage et al., J Clin Invest (2006), 116: 817-824; Mo et al., Proc Natl Acad Sci USA (2006), 103: 8552-8557). The reduction in the activity of ACC2 further leads to a reduction in body weight and a modulation of food intake (Abu-Elheiga et al., Science (2001), 291: 2613-2616). ACC is overexpressed in various tumors (Swinnen et al., Int J Cancer (2000), 88: 176-179, Milgraum et al., Clin Cancer Res (1997), 3: 2115-2120). ACC1 further interacts with the breast cancer susceptibility gene 1 (BRCA1; Magnard et al., Oncogene (2002), 21: 6729-6239).

Enzymatic Assay of ACC Inhibitors

Human ACC

Human ACC1 and human ACC2 were expressed in the Bacculovirus/High five cell system as fusion protein with an N-terminal His tag and purified by a combination of affinity chromatography and gel chromatography. The solubility was increased by using an ACC2 expression construct lacking 150 amino acids at the N terminus. The preparations had a specific activity of 50-100 mU/mg of protein.

Enzymatic Assay

The enzymatic activity of ACC and its inhibition by test substances were determined by a luminometric assay. The reaction mixture contained 50 mM tris acetate (Merck, #1.08382.1000), pH 7.5, 250 μM acetyl coenzyme A (Sigma, #A2181), 16 mM $NaHCO_3$ (Merck, #1.06329.0500), 0.9 mg/ml bovine serum albumin (Sigma, #A8806), 25 μM ATP (Sigma, #A7699), 1.1 μM β-mercaptoethanol (Roth, #4227, 1), 4.3 mM magnesium acetate ((Merck, #1.05819.0250), 10 mM sodium citrate (Merck, #1.06448.0500) and 200-400 ng of the ACC preparations. The mixture also contained a test compound. The test compounds were each dissolved in 10 mM DMSO and were assayed at final concentrations of 0 µM, 0.01 µM, 0.03 µM, 0.1 µM, 0.3 µM, 1 µM, 3 µM, 10 µM, 30 µM and 100 µM. The final concentration of the DMSO in the assay was 0.1% (v/v). The reaction was started by adding ACC and was carried out at 37° C. for 90 min. The reaction was then stopped by adding 150 µl of 0.5 M tris acetate. 10 µl of the mixture were removed and mixed with 90 µl of ATP monitoring reagent (Cambrex, #LT27-002). After incubation for 10 min, the luminescence was measured in a luminometer (Tecan Genios Pro).

Evaluation

The crude luminescence data were transferred into a Microsoft Excel file. The luminescence measured in the absence of ACC in the reaction mixture was defined as 100%. The value in the presence of ACC with 0 µM test compound was set at 0%. Dose-effect plots were calculated with the XL.Fit program as specified by the producer (IDBS). The IC50 of a test substance was the concentration of the test compound at which a luminescence of 50% was measured.

TABLE 1

(hACC2)

| Example | IC50 [µM] |
|---|---|
| 2 | 0.14 |
| 4 | 0.4 |
| 6 | 0.2 |
| 7 | 1.28 |
| 9 | 0.14 |
| 10 | 0.15 |
| 11 | 0.14 |
| 12 | 0.05 |
| 17 | 0.05 |
| 19 | 0.1 |
| 20 | 3.6 |
| 23 | 2.0 |
| 25 | 0.38 |
| 27 | 1.3 |
| 29 | 1.2 |
| 31 | 0.2 |
| 32 | 1.3 |
| 33 | 0.06 |
| 35 | 0.03 |
| 36 | 0.07 |
| 37 | 5.9 |
| 39 | 2.5 |
| 40 | 0.74 |
| 44 | 0.09 |
| 45 | 0.67 |
| 46 | 0.21 |
| 47 | 0.15 |
| 48 | 0.9 |
| 49 | 1.2 |
| 50 | 0.17 |
| 51 | 0.08 |
| 52 | 0.08 |
| 59 | 0.11 |

The compounds of the formula I inhibit ACC activity and are therefore very suitable for the treatment of lipid metabolism disorders, obesity, diabetes and the metabolic syndrome (C. Soo Choi et al. PNAS (2007), 104: 16480.16485; N. Ruderman et al., Nat Rec Drug Disc. (2004), 3: 340-351; L. Abu-Elheiga et al., Science (2001), 291: 2613-2616).

The compounds of the formula I exhibit also a good correlation of ACC test results obtained with human ACC (hACC) and of ACC of rodent origin, especially of the rat (rACC). This leads to reliable test results, necessary for the preclinical development of a future drug for example in toxicologic studies in animal models. This is demonstrated by the following test results shown in table 2. Example 59 is a comparative example of compounds disclosed in WO 2008079610, example 35 the corresponding compound of the invention.

Example 35 differentiates from the comparative example 59 in the following biological in vitro characteristics: example 35 inhibits human ACC2 and human ACC1 with approx. 5 times and 40 times, respectively higher potency than example 59 and possess >3 times higher potency towards the respective rat ACC isoforms.

TABLE 2

| target | IC50 [µM] Ex. 59 | IC50 [µM] Ex. 35 |
|---|---|---|
| hACC2 | 0.12 | 0.03 |
| hACC | 7.80 | 0.19 |
| rACC2 | 1.50 | 0.4 |
| rACC1 | >10 | 0.17 |

In another pharmacological test both compounds were tested for palmitate oxidation in a mouse muscle cell line (C2C12) which is also mediated by ACC inhibition. Example 35 is able to stimulate cellular fat oxidation in a mouse muscle cell line at a concentration of 10 µM significantly (1.7 fold), whereas example 59 has no effect in this assay.

Owing to the inhibition of ACC activity, the compounds of the formula I can also be used for the treatment or prevention of further diseases mediated by ACC and of a condition mediated via ACC in a mammal, preferably a human.

The compounds of the present invention are particularly suitable for the treatment and/or prevention of:

1.—obesity, especially visceral (abdominal) obesity
2.—disorders of fatty acid metabolism and glucose utilization disorders
   disorders in which insulin resistance is involved
3. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic 1 cells
   prevention of macro- and microvascular disorders
4. Dyslipidemias and their sequelae such as, for example, atherosclerosis, coronary heart disease, cerebrovascular disorders etc., especially those (but not restricted thereto) which are characterized by one or more of the following factors:
   high plasma triglyceride concentrations, high postprandial plasma triglyceride concentrations,
   low HDL cholesterol concentration
   low apoA lipoprotein concentrations
   high LDL cholesterol concentrations
   small dense LDL cholesterol particles
   high apoB lipoprotein concentrations
   desaturation index (e.g. ratio 18:1/18:0n-9, 16:1/16:0 n-7 or 18:1n-9+16:1n-7/16:0 fatty acids)
5. Various other conditions which may be associated with the metabolic syndrome or syndrome X, such as:
   increased abdominal girth
   dyslipidemia (e.g. hypertriglyceridemia and/or low HDL)
   insulin resistance
   hypercoagulability
   hyperuricemia microalbuminemia thromboses, hypercoagulable and prothrombotic states (arterial and venous)

high blood pressure heart failure such as, for example (but not restricted thereto), following myocardial infarction, hypertensive heart disease or cardiomyopathy 6. Hepatic disorders and conditions related thereto
   fatty liver
   hepatic steatosis
   non-alcoholic hepatitis
   non-alcoholic steatohepatitis (NASH)
   alcoholic hepatitis
   acute fatty liver
   fatty liver of pregnancy
   drug-induced hepatitis
   iron storage diseases
   hepatic fibrosis
   hepatic cirrhosis
   hepatoma
   viral hepatitis 7. Skin disorders and conditions and those associated with polyunsaturated fatty acids
   eczema
   acne
   psoriasis
   keloid scar formation or prevention
   other diseases related to mucous membrane fatty acid composition 8. Primary hypertriglyceridemia or secondary hypertriglyceridemias following
   familial histiocytic reticulosis
   lipoprotein lipase deficiency
   hyperlipoproteinemias
   apolipoprotein deficiency (e.g. apoCII or apoE deficiency)

9. Diseases or conditions related to neoplastic cellular proliferation
   benign or malignant tumors
   cancer
   neoplasias
   metastases
   carcinogenesis 10. Diseases or conditions related to neurological, psychiatric or immune disorders or conditions 11. Other diseases or conditions in which inflammatory reactions, cell differentiation and/or other ACC-mediated aspects may for example be involved are:
    atherosclerosis such as, for example (but not restricted thereto), coronary sclerosis including angina pectoris or myocardial infarction, stroke, ischemic stroke and transient ischemic attack (TIA)
    peripheral occlusive disease
    vascular restenosis or reocclusion
    chronic inflammatory bowel diseases such as, for example, Crohn's disease and ulcerative colitis
    pancreatitis
    sinusitis
    other inflammatory conditions
    retinopathy, ischemic retinopathy
    adipose cell tumors
    lipomatous carcinomas such as, for example, liposarcomas
    solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc.
    acute and chronic myeloproliferative disorders and lymphomas
    angiogenesis
    neurodegenerative disorders
    Alzheimer's disease
    multiple sclerosis
    Parkinson's disease
    erythemato-squamous dermatoses such as, for example, psoriasis
    acne vulgaris
    other skin disorders and dermatological conditions which are modulated by PPAR
    eczemas and neurodermatitis
    dermatitis such as, for example, seborrheic dermatitis or photodermatitis
    keratitis and keratoses such as, for example, seborrheic keratoses, senile keratoses, actinic keratoses, photo-induced keratoses or keratosis follicularis
    keloids and keloid prophylaxis
    warts, including condylomata or condylomata acuminata
    human papilloma viral (HPV) infections such as, for example, venereal papillomata, viral warts such as, for example, molluscum contagiosum, leukoplakia
    papular dermatoses such as, for example, lichen planus
    skin cancer such as, for example, basal-cell carcinomas, melanomas or cutaneous T-cell lymphomas
    localized benign epidermal tumors such as, for example, keratoderma, epidermal naevi
    chilblains
    high blood pressure
    syndrome X
    polycystic ovary syndrome (PCOS)
    asthma
    cystic fibrosis
    osteoarthritis
    lupus erythematosus (LE) or inflammatory rheumatic disorders such as, for example, rheumatoid arthritis
    vasculitis
    wasting (cachexia)
    gout
    ischemia/reperfusion syndrome
    acute respiratory distress syndrome (ARDS)
    viral diseases and infections
    lipodystrophy and lipodystrophic conditions, also for treating adverse drug effects (e.g. after taking medicaments for treating HIV or tumors)
    myopathies and lipid myopathies (such as carnitine palmitoyltransferase I or II deficiency)

12. Formation of muscles and a lean body or muscle mass formation in animal management and in humans.

Preparation

The compounds of the invention of the general formula I are prepared by processes known per se in the literature, and can be obtained via the following reaction sequences in which the radicals have the meanings indicated above.

Compounds of the formula I with W=O or S can be prepared by reacting activated heterocycles II in which X is halogen or another leaving group (such as, for example, methanesulfonate, toluenesulfonate) with nucleophiles III such as the appropriate phenols or mercaptans under alkaline conditions. For example, a 2-chloropyridine derivative IIaa is reacted with the phenol IIIaa to give the compound Iaa. The reactions are carried out in suitable solvents, it being necessary to adapt the reaction temperature to the reactivities.

Thus, heating up to the boiling point of the appropriate solvent is possible, and reaction in a microwave reactor or addition of catalysts such as copper salts are also used where appropriate.

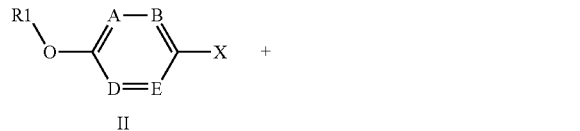

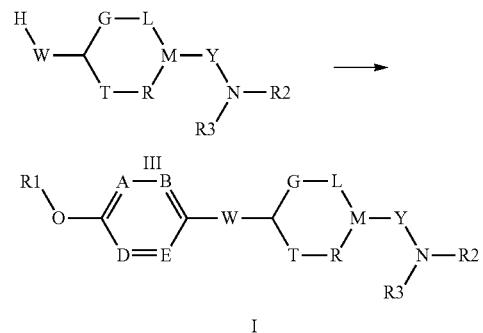

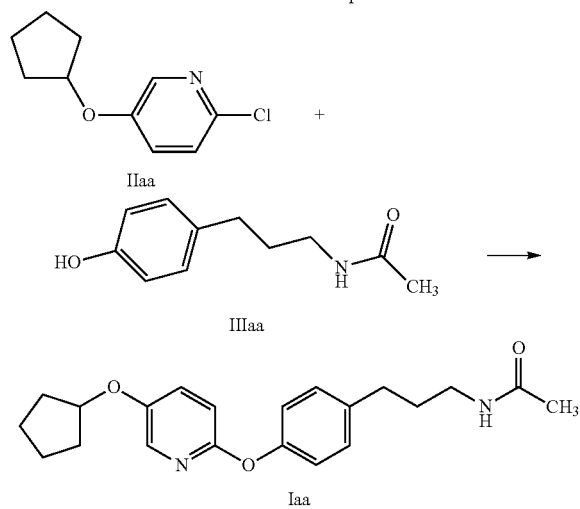

Coupling of the cyclic building blocks ABDE and GLRT can also be undertaken by reacting appropriate phenols or mercaptans IV with an activated compound V under conditions as indicated above.

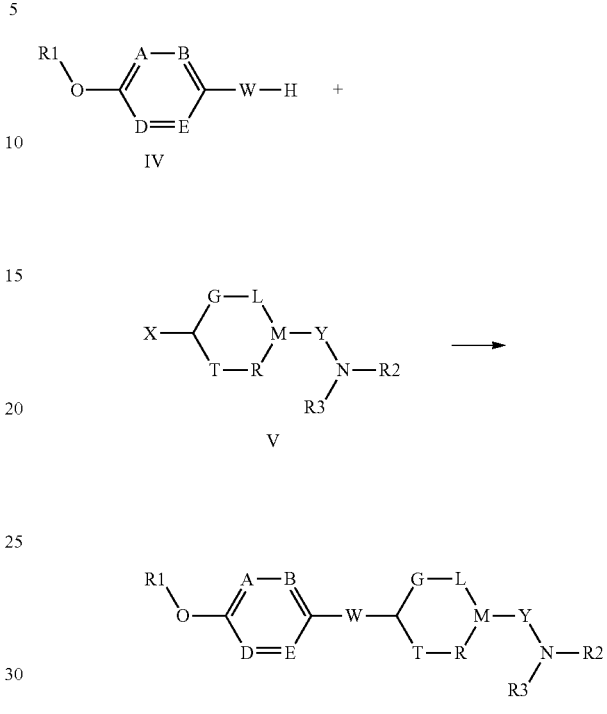

The sequence of the various reaction steps can also take place in another way. Thus, for example, to prepare a compound of the formula I with M=N it is possible to react a phenol VIa with a bromide-activated ring GLRT whose N atom is BOC protected as described above. In the next step, the protective group is eliminated, and the Y—NH$_2$ member is introduced by amidation by a BOC-protected amino group. Subsequent reduction eliminates the protective group and leads to the intermediates VIa or VIb, depending on the chosen conditions. The corresponding compounds of the formula I are then obtained by amidation.

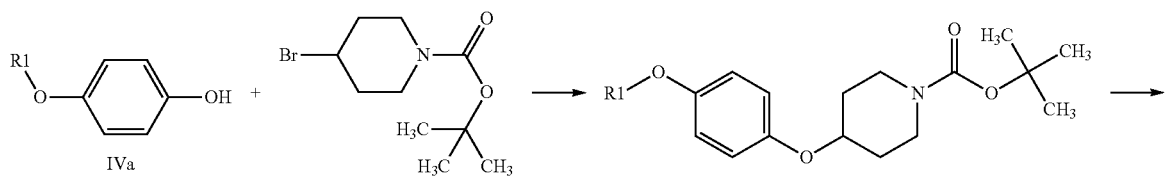

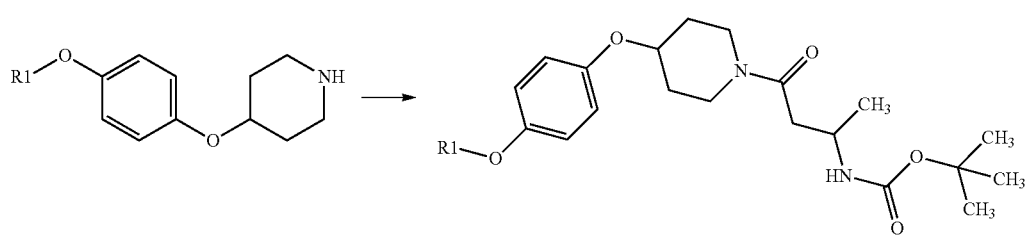

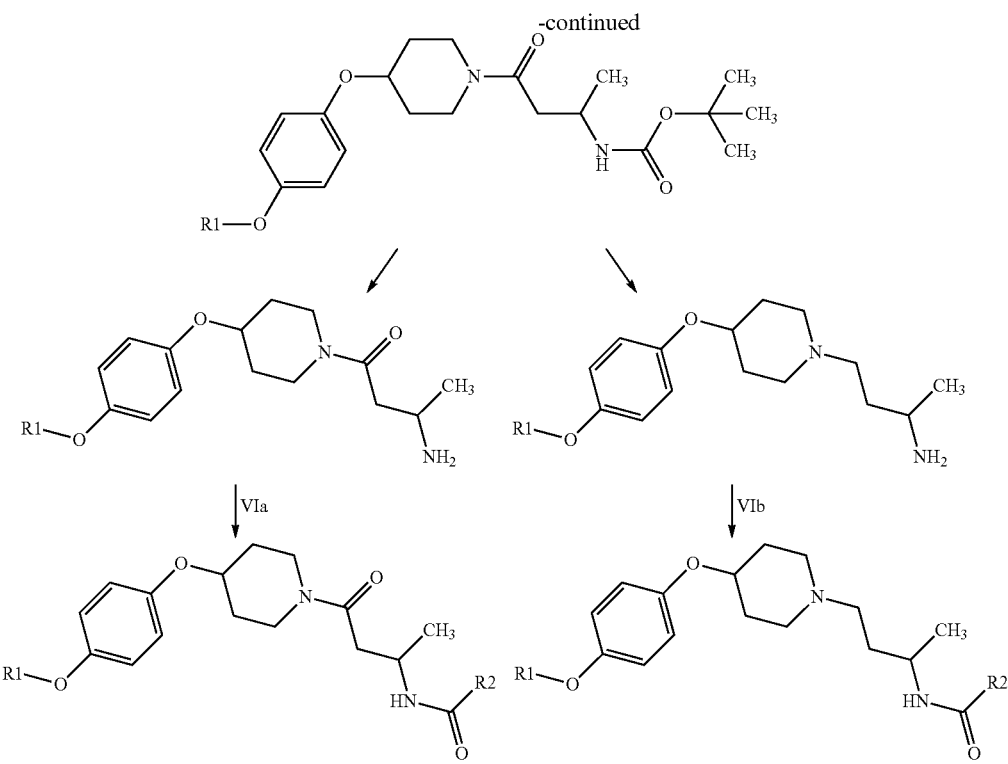

The sequence of the various reaction steps can also take place in another way. Thus, the reactivity of reactant II in the nucleophilic substitution can be increased by introducing an activating substituent such as the nitro group (IIa). The nitro group can then be converted by processes disclosed in the literature after reduction to the corresponding amine and subsequent diazotization and reaction with a nucleophile into the compounds of the invention.

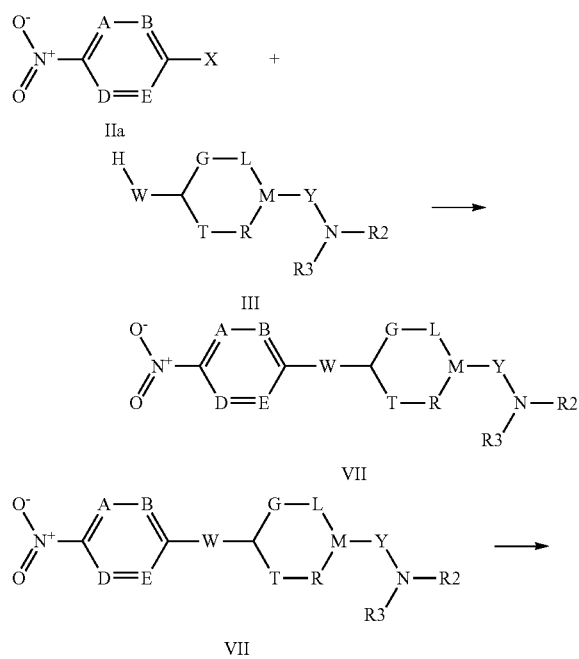

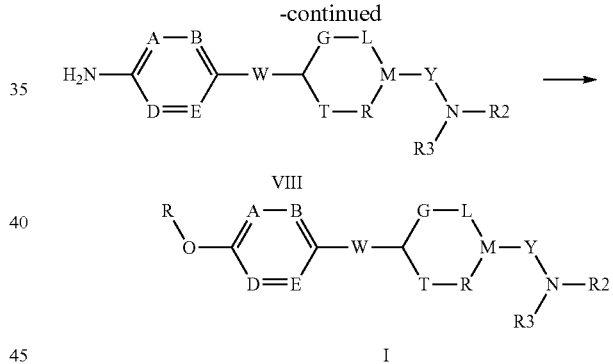

Also by reaction of halogenids under metall catalysis leads to the compounds of the invention: especially the catalysis of copper compounds (Org. Lett. 2003, 5, 3799-3802, Org. Lett. 2005, 7, 4693-4695) or palladium (J. Am. Chem. Soc. 2005, 127, 8145-8149; Angew. Chem. Int. Ed. 2006, 45, 4321-4326).

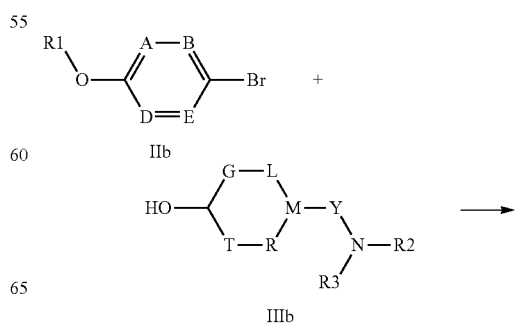

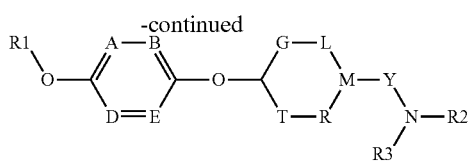

Ib

Also derivatives of boronic acid are suitable educts for the copper catalyst based preparation of the compounds of the invention (Tetrahedron Lett. 2003, 44, 3863-3865).

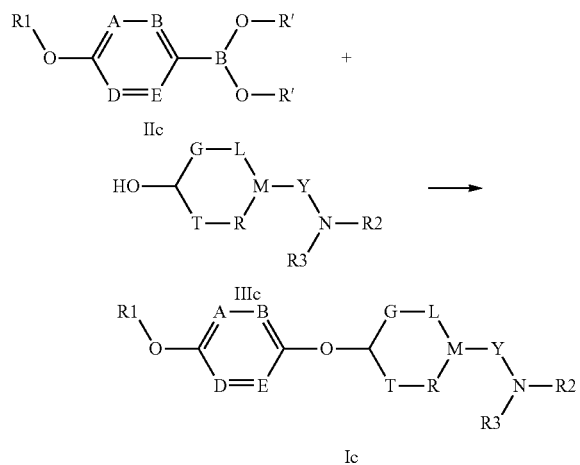

The compounds used as starting materials are commercially available or can be prepared by processes disclosed in the literature.

If acids are liberated during these reactions it is advantageous to add bases such as pyridine, triethylamine, sodium hydroxide solution or alkali metal carbonates to increase the rate. Under anhydrous conditions, strong bases such as lithium hydride, sodium hydride or potassium tert-butanolate in aprotic solvents such as THF or DMF have also proved suitable. The reactions can be carried out in wide temperature ranges. It has proved advantageous to operate at temperatures from 0° C. to the boiling point of the solvent used. Examples of solvents used are methylene chloride, THF, DMF, N-methylpyrrolidinone, toluene, ethyl acetate, n-heptane, dioxane, diethyl ether or pyridine.

The compounds of the general formula I are isolated from the reaction mixture and purified by processes known per se, such as extraction, crystallization or chromatography.

The following examples serve to explain the invention in more detail without restricting the latter to the products and embodiments described in the examples.

The identity of the compounds was examined by mass spectrometry.

EXAMPLES

Example 1

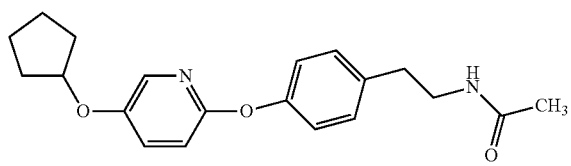 [SMILES: CC(=O)NCCc1ccc(Oc2ccc(OC3CCCC3)cn2)cc1]

N-{2-[4-(5-Cyclopentyloxypyridin-2-yloxy)phenyl]ethyl}acetamide 1a. 2-Chloro-5-cyclopentyloxypyridine Cyclopentyl bromide (690.3 mg, 4.63 mmol), 2-chloro-5-hydroxypyridine (500 mg, 3.86 mmol) and cesium carbonate (1.51 g, 4.63 mmol) were stirred in 30 ml of DMF at room temperature for 3 h. The reactants had not yet completely reacted. 50% of each of cyclopentyl bromide and cesium carbonate were added, and stirring was continued for 2 h. The reaction mixture was concentrated in vacuo, and the residue was taken up in ethyl acetate and water. The organic phase was separated off and concentrated. Yield: 737 mg (97%), M+H+: 198.08.

1b. N-{2-[4-(5-Cyclopentyloxypyridin-2-yloxy)phenyl]ethyl}acetamide

N-[2-(4-Hydroxyphenyl)ethyl]acetamide (668.3 mg, 3.73 mmol), 2-chloro-5-cyclopentyloxypyridine (737 mg, 3.73 mmol) and cesium carbonate (1.458 g, 4.475 mmol) were treated at 230° C. in 24 ml of DMF in a microwave reactor for 2 h. The reaction mixture was concentrated, and the residue was taken up in ethyl acetate and water. The organic phase was separated off, concentrated and purified by preparative HPLC (PR18, acetonitrile/water 0.1% TFA). Yield: 8 mg (1%), M+H+: 341.13.

Example 2

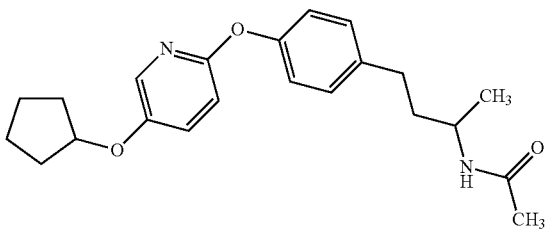 [SMILES: CC(=O)NC(C)CCc1ccc(Oc2ccc(OC3CCCC3)cn2)cc1]

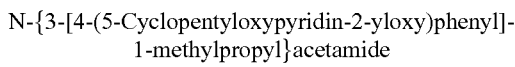

N-{3-[4-(5-Cyclopentyloxypyridin-2-yloxy)phenyl]-1-methylpropyl}acetamide

2a. N-[3-(4-Hydroxyphenyl)-1-methylpropyl]acetamide 4-(3-Aminobutyl)phenol (510 mg, 3.087 mmol) and triethylamine (1.3 ml, 9.26 mmol) were dissolved in 30 ml of ethyl acetate. At 0° C., acetic anhydride (029 ml, 3.087 mmol) was added. The cooling bath was removed after 1 h. The reaction mixture was concentrated, and the residue was purified by preparative HPLC (PR18, acetonitrile/water 0.1% TFA). Yield: 472 mg (74%) of N-[3-(4-hydroxyphenyl)-1-methylpropyl]acetamide, M+H+: 208.14 and 54 mg (7%) of 4-(3-acetylaminobutyl)phenyl acetate, M+H+: 250.13.

2b. N-[3-(4-Hydroxyphenyl)-1-methylpropyl]acetamide 4-(3-Acetylaminobutyl)phenyl acetate (1.06 g, 4.25 mmol) was dissolved in 10 ml of methanol and, after addition of sodium methoxide (689.3 mg, 12.76 mmol), the reaction mixture was stirred at RT for 2 h. The pH was adjusted to 7 by adding dilute hydrochloric acid, and the mixture was extracted with ethyl acetate. The organic phases were combined and concentrated in vacuo. Yield: 805 mg (91%), M+H+: 208.15.

2c. N-{3-[4-(5-Cyclopentyloxypyridin-2-yloxy)phenyl]-1-methylpropyl}acetamide N-[3-(4-Hydroxyphenyl)-1-methylpropyl]acetamide (104.9 mg, 0.51 mmol), 2-chloro-5-cyclopentyloxypyridine (100 mg, 0.51 mmol) and sodium hydride (50% in oil) (26 mg, 0.54 mmol) were treated at 230° C. in 5 ml of N-methylpyrrolidinone in a microwave reactor for 1 h. Addition of a further 26 mg of sodium hydride was followed by again heating at 240° C. for 1 h. The reaction mixture was concentrated, and the residue was taken up in ethyl acetate and water. The organic phase was separated off, concentrated and purified by preparative HPLC (PR18, acetonitrile/water 0.1% TFA). Yield: 16 mg (9%), M+H+: 369.17.

Example 3/4

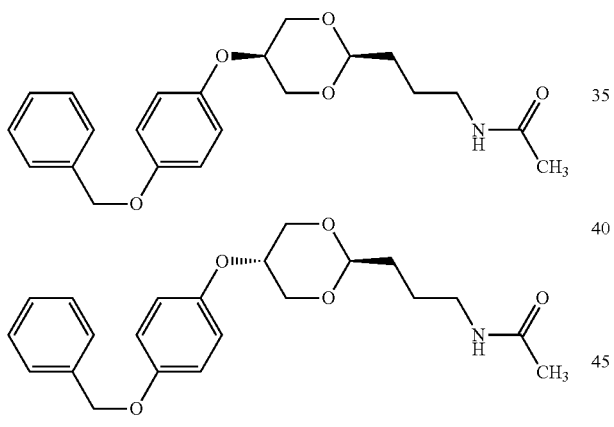

N-{3-[5-(4-Benzyloxyphenoxy)-[1,3]dioxan-2-yl]propyl}acetamide

3a. N-(4,4-Diethoxybutyl)acetamide 4,4-Diethoxybutylamine (3.0 g, 18.61 mmol) and triethylamine (7.85 ml, 55.83 mmol) were dissolved in 250 ml of ethyl acetate. At 10° C., acetic anhydride (1.75 ml, 18.61 mmol) was added, and stirring was continued for 2 h. The cooling bath was removed after 1 h. The reaction mixture was concentrated. Yield: 1.526 g. The product was directly reacted further.

3b. Dimethyl 2-(4-benzyloxyphenoxy)malonate

4-Benzyloxyphenol (1.0 g, 4.99 mmol), dimethyl 2-chloromalonate (998.2 mg, 5.99 mmol), cesium carbonate (3.25 g, 9.99 mmol) and potassium iodide (41.45 mg, 0.25 mmol) were stirred in 50 ml of DMF at 60° C. for 1.5 h. Addition of 200 μl of dimethyl 2-chloromalonate was followed by stirring at 60° C. for 1 h and at 80° C. for 1 h and concentration, and the residue was taken up in ethyl acetate and water. The organic phase was separated off, concentrated and purified by preparative HPLC (PR18, acetonitrile/water 0.1% TFA). Yield: 477 mg (29%), M+H+: 331.18.

3c. 2-(4-Benzyloxyphenoxy)propane-1,3-diol

Diisobutylaluminum hydride (7.08 ml) was slowly added dropwise to dimethyl 2-(4-benzyloxyphenoxy)malonate (477 mg, 1.44 mmol) in 16 ml of toluene under argon at 0° C. The reaction mixture was stirred at 0° C. for 2 h and, after addition of 1M hydrochloric acid solution, extracted with ethyl acetate. The organic phase was separated off, concentrated and purified by preparative HPLC (PR18, acetonitrile/water 0.1% TFA). Yield: 98.6 mg (25%), M+H+: 275.20.

3d. cis-N-{3-[5-(4-Benzyloxyphenoxy)-[1,3]dioxan-2-yl]propyl}acetamide and trans-N-{3-[5-(4-benzyloxyphenoxy)-[1,3]dioxan-2-yl]propyl}acetamide 2-(4-Benzyloxyphenoxy)propane-1,3-diol (98 mg, 0.36 mmol), N-(4,4-diethoxybutyl)acetamide (73.06 mg, 0.36 mmol) and p-toluenesulfonic acid (61.89 mg, 0.36 mmol) were stirred in 6 ml of toluene at 60° C. for 2 h and concentrated. The organic phase was separated off, concentrated and purified by preparative HPLC (PR18, acetonitrile/water 0.1% TFA). Yield: 30.8 mg (22%) of cis-N-{3-[5-(4-benzyloxyphenoxy)-[1,3]dioxan-2-yl]propyl}acetamide, M+H+: 386.15 and 29.8 mg (22%) of trans-N-{3-[5-(4-benzyloxyphenoxy)-[1,3]dioxan-2-yl]propyl}acetamide, M+H+: 386.19.

Example 5

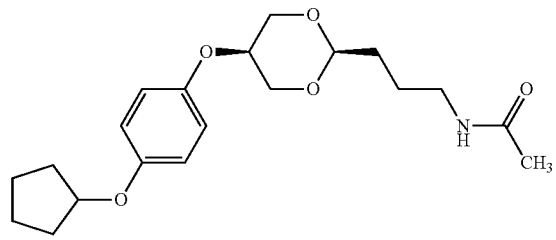 [SMILES: CC(=O)NCCC[C@H]1OC[C@@H](Oc2ccc(OC3CCCC3)cc2)CO1]

cis-N-{3-[5-(4-Cyclopentyloxyphenoxy)-[1,3]dioxan-2-yl]propyl}acetamide

5a. cis-N-{3-[5-(4-Hydroxyphenoxy)-[1,3]dioxan-2-yl]propyl}acetamide cis-N-{3-[5-(4-Benzyloxyphenoxy)-[1,3]dioxan-2-yl]propyl}acetamide (25 mg, 0.065 mmol) was dissolved in 5 ml of ethanol and hydrogenated in the presence of 0.69 mg of palladium/carbon under 3 bar for 1 h. The reaction mixture was concentrated and directly reacted further. Yield 18 mg.

5b. cis-N-{3-[5-(4-Cyclopentyloxyphenoxy)-[1,3]dioxan-2-yl]propyl}acetamide cis-N-{3-[5-(4-Hydroxyphenoxy)-[1,3]dioxan-2-yl]propyl}acetamide (18.6 mg, 0.063 mmol), cyclopentyl bromide (11.3 mg, 0.076 mmol) and cesium carbonate (24.6 mg, 0.076 mmol) were stirred in 3 ml of DMF at room temperature for 3 h. Addition of 11 mg of cyclopentyl bromide and 20 mg of cesium carbonate on each of two occasions was followed by stirring for a total of 8 h and concentrating, and the residue was taken up in ethyl acetate and water. The organic phase was separated off, concentrated and purified by preparative HPLC (PR18, acetonitrile/water 0.1% TFA). Yield: 8.5 mg (37%), M+H+: 364.22.

Example 6

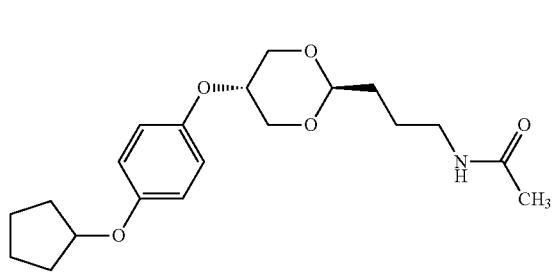 [SMILES: CC(=O)NCCC[C@H]1OC[C@H](Oc2ccc(OC3CCCC3)cc2)CO1]

trans-N-{3-[5-(4-Cyclopentyloxyphenoxy)-[1,3]dioxan-2-yl]propyl}acetamide trans-N-{3-[5-(4-Benzyloxyphenoxy)-[1,3]dioxan-2-yl]propyl}acetamide (24 mg, 0.062 mmol) was hydrogenated and reacted with cyclopentyl bromide in analogy to example 5. Yield: 6 mg (34%) M+H+: 364.21.

Example 7

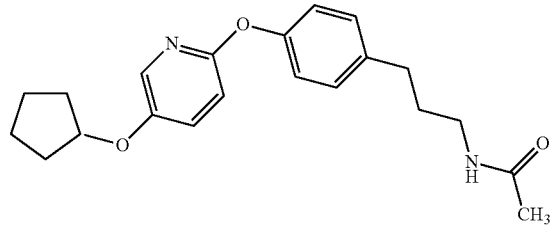

N-{3-[4-(5-Cyclopentyloxypyridin-2-yloxy)phenyl]propyl}acetamide

N-[3-(4-Hydroxyphenyl)propyl]acetamide was reacted with 2-chloro-5-cyclopentyloxypyridine in analogy to example 2c. M+H+: 355.18.

Example 8

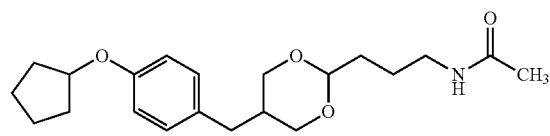 [SMILES: CC(=O)NCCCC1OCC(Cc2ccc(OC3CCCC3)cc2)CO1]

N-{3-[5-(4-Cyclopentyloxybenzyl)-[1,3]dioxan-2-yl]propyl}acetamide 2-(4-Cyclopentyloxybenzyl)propane-1,3-diol (92 mg, 337 μmol) was reacted with N-(4,4-diethoxybutyl)acetamide in analogy to example 3d. Yield: 81 mg (60%), M+H+: 362.27.

Example 9

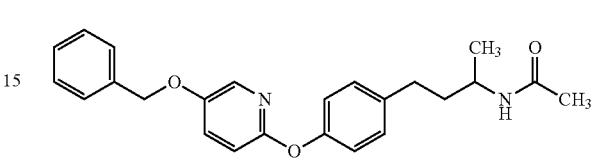

N-{3-[4-(5-Benzyloxypyridin-2-yloxy)phenyl]-1-methylpropyl}acetamide

5-Benzyloxy-2-fluoropyridine (980 mg, 4.82 mmol) was reacted with N-[3-(4-hydroxy-phenyl)-1-methylpropyl]acetamide in analogy to example 1b.

Yield: 394 mg (21%), M+H+: 391.19.

Example 10

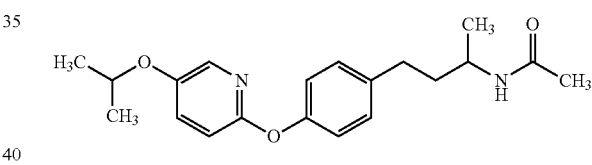

N-{3-[4-(5-Isopropoxypyridin-2-yloxy)phenyl]-1-methylpropyl}acetamide

10a: N-{3-[4-(5-Hydroxypyridin-2-yloxy)phenyl]-1-methylpropyl}acetamide

N-{3-[4-(5-Benzyloxypyridin-2-yloxy)phenyl]-1-methylpropyl}acetamide (344 mg, 881 μmol) were dissolved in 20 ml of ethanol. Addition of 93 mg of palladium/carbon was followed by hydrogenation under a pressure of 5 bar of hydrogen at room temperature for 16 h. The catalyst was filtered off and the filtrate was concentrated. Yield: 220 mg (83%), M+H+: 301.13.

10b: N-{3-[4-(5-Isopropoxypyridin-2-yloxy)phenyl]-1-methylpropyl}acetamide

N-{3-[4-(5-Hydroxypyridin-2-yloxy)phenyl]-1-methylpropyl}acetamide (50 mg, 166 μmol), 2-iodopropane (28 mg, 166 μmol) and cesium carbonate (135 mg, 416 μmol) were stirred in 3 ml of DMF at 50° C. for 3 h. The reaction mixture was concentrated in vacuo, and the residue was purified by preparative HPLC (PR18, acetonitrile/water 0.1% TFA). Yield: 35 mg (61%), M+H+: 343.16.

Example 11

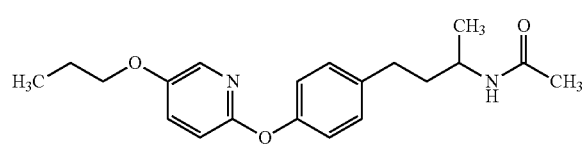 [SMILES: CCCOc1ccc(Oc2ccc(CCC(C)NC(C)=O)cc2)nc1]

N-{1-Methyl-3-[4-(5-propoxypyridin-2-yloxy)phenyl]propyl}acetamide

N-{3-[4-(5-Hydroxypyridin-2-yloxy)phenyl]-1-methylpropyl}acetamide was reacted with 1-bromopropane in analogy to example 10b. Yield: 38 mg (66%), M+H+: 343.13.

Example 12

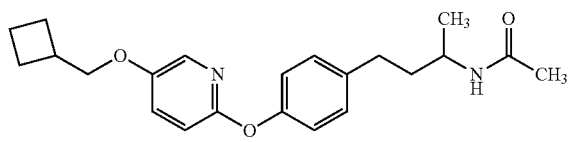 [SMILES: CC(=O)NC(C)CCc1ccc(Oc2ccc(OCC3CCC3)cn2)cc1]

N-{3-[4-(5-Cyclobutylmethoxypyridin-2-yloxy)phenyl]-1-methylpropyl}acetamide

N-{3-[4-(5-Hydroxypyridin-2-yloxy)phenyl]-1-methylpropyl}acetamide was reacted with bromomethylcyclobutane in analogy to example 10b.

Yield: 45 mg (73%), M+H+: 369.25.

Example 13

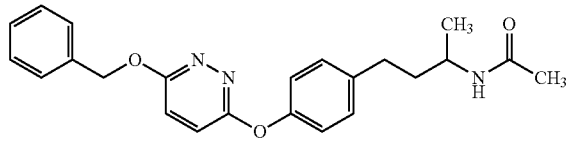 [SMILES: CC(=O)NC(C)CCc1ccc(Oc2ccc(OCc3ccccc3)nn2)cc1]

N-{3-[4-(6-Benzyloxypyridazin-3-yloxy)phenyl]-1-methylpropyl}acetamide

3-Benzyloxy-6-chloropyridazine (411 mg, 1.86 mmol) was reacted with N-[3-(4-hydroxyphenyl)-1-methylpropyl] acetamide in analogy to example 1b.

Yield: 102 mg (14%), M+H+: 392.30.

Example 14/15

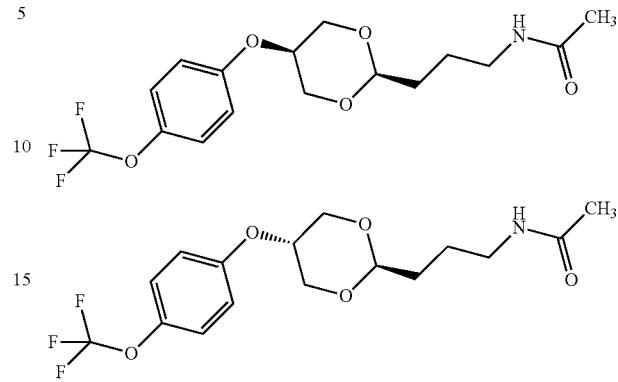

2-(4-Trifluoromethoxyphenoxy)propane-1,3-diol (37 mg, 146 µmol) was reacted with N-(4,4-diethoxybutyl)acetamide (30 mg, 147 µmol) in analogy to example 3d. Yield: cis-N{3-[5-(4-trifluoromethoxyphenoxy)-[1,3]dioxan-2-yl] propyl}acetamide (example 14), 7 mg (13%), M+H+: 364.13 and trans-N{3-[5-(4-trifluoromethoxyphenoxy)-[1,3]dioxan-2-yl]propyl}acetamide (example 15), 6 mg (11%), M+H+: 364.14.

Example 16/17

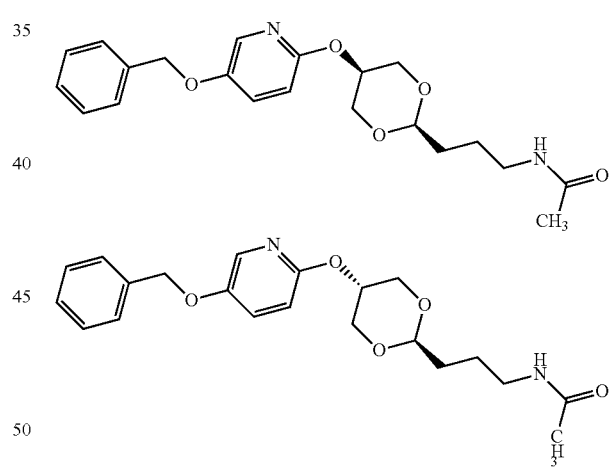

16a: 5-Benzyloxy-2-(2-phenyl-[1,3]dioxan-5-yloxy) pyridine

2-Phenyl-[1,3]dioxan-5-ol (164 mg. 910 µmol) was dissolved in 5 ml of NMP. Addition of sodium hydride (60% in oil, 72.8 mg, 1.8 mmol) was followed by stirring at RT for 30 min and, after addition of 5-benzyloxy-2-chloropyridine (200 mg, 910 µmol), stirring in a microwave reactor at 200° C. for 1 h. The reaction mixture was concentrated in vacuo, the residue was taken up in ethyl acetate and water, and the organic phase was concentrated. The resulting crude product (386 mg) was directly reacted further.

16b: 2-(5-Benzyloxypyridin-2-yloxy)propane-1,3-diol

5-Benzyloxy-2-(2-phenyl-[1,3]dioxan-5-yloxy)pyridine was mixed with 20 ml of 4N hydrochloric acid and 20 ml of methanol and stirred at RT for 2 h. The methanol was concentrated in vacuo and the resulting acidic solution was made alkaline with saturated sodium carbonate solution. The alkaline solution was extracted with ethyl acetate, and the organic phase was concentrated.
Yield: 216 mg (86%), M+H+: 276.16.

16c: N-{3-[5-(5-Benzyloxypyridin-2-yloxy)-[1,3]dioxan-2-yl]propyl}acetamide, cis and trans isomers 2-(5-Benzyloxypyridin-2-yloxy)propane-1,3-diol (216 mg, 784 μmol) was reacted with N-(4,4-diethoxybutyl)acetamide in analogy to example 3d. Yield: cis-N-{3-[5-(5-benzyloxypyridin-2-yloxy)-[1,3]dioxan-2-yl]propyl}acetamide (example 16), 21 mg (7%), M+H+: 387.22 and trans-N-{3-[5-(5-benzyloxypyridin-2-yloxy)-[1,3]dioxan-2-yl]propyl}acetamide (example 17), 6 mg (2%), M+H+: 387.23.

Example 18/19

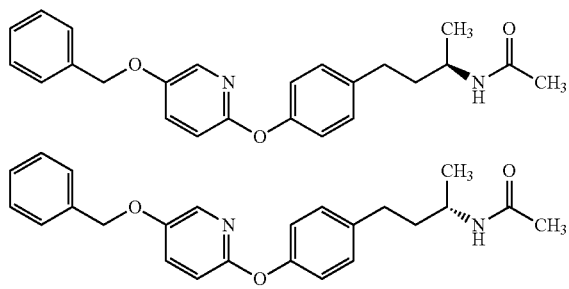

N-{3-[4-(5-Benzyloxypyridin-2-yloxy)phenyl]-1-methylpropyl}acetamide (example 9, 115 mg) was chromatographed on a chiral column (Chiralpak AD-H/55, 250×4.6 mm, eluent: heptane-ethanol/methanol=5:1:1) to separate the enantiomers
N—{(R)-3-[4-(5-Benzyloxypyridin-2-yloxy)phenyl]-1-methylpropyl}acetamide (example 18), 50 mg, M+H+: 391.12, RF: 6.41 min.
N—{(S)-3-[4-(5-Benzyloxypyridin-2-yloxy)phenyl]-1-methylpropyl}acetamide (example 19), 50 mg, M+H+: 391.11, RF: 8.56 min.

Example 20

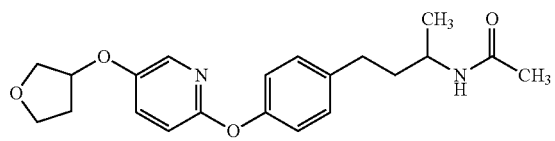 [SMILES: CC(=O)NC(C)CCc1ccc(Oc2ccc(OC3CCOC3)cn2)cc1]

N-(1-Methyl-3-{4-[5-(tetrahydrofuran-3-yloxy)pyridin-2-yloxy]phenyl}propyl)acetamide N-[3-(4-Hydroxyphenyl)-1-methylpropyl]acetamide was reacted with 2-chloro-5-(tetrahydrofuran-3-yloxy)pyridine in analogy to example 2c.
Yield: 15 mg (4%), M+H+: 371.14.

Example 21

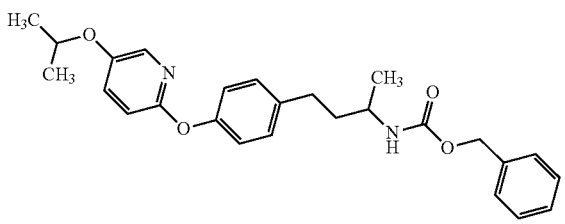 [SMILES: CC(CCc1ccc(Oc2ccc(OC(C)C)cn2)cc1)NC(=O)OCc1ccccc1]

Benzyl {3-[4-(5-isopropoxypyridin-2-yloxy)phenyl]-1-methylpropyl}carbamate

Benzyl 3-(4-hydroxyphenyl)-1-methylpropyl]carbamate was reacted with 2-chloro-5-isopropoxypyridine in analogy to example 2c.
Yield: 12 mg (1%), M+H+: 435.11.

Example 22/23

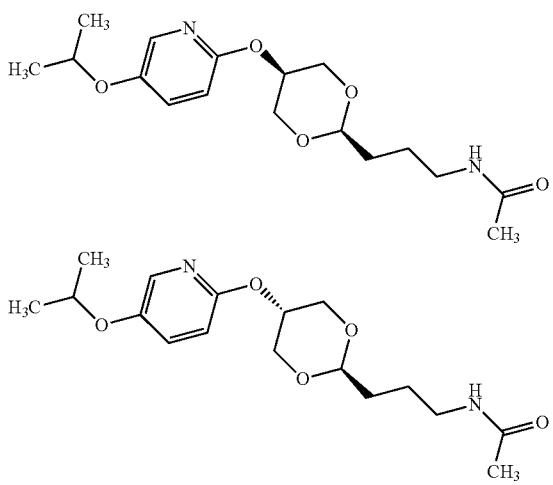

2-(5-Isopropoxypyridin-2-yloxy)propane-1,3-diol (300 mg, 1.32 mmol) was reacted with N-(4,4-diethoxybutyl)acetamide in analogy to example 3d. Yield: cis-N-{3-[5-(5-isopropoxypyridin-2-yloxy)-[1,3]dioxan-2-yl]propyl}acetamide (example 22), 11 mg (2%), M+H+: 339.16 and trans-N-{3-[5-(5-isopropoxypyridin-2-yloxy)-[1,3]dioxan-2-yl]-propyl}acetamide (example 23), 10 mg (2%), M+H+: 339.19.

Example 24/25

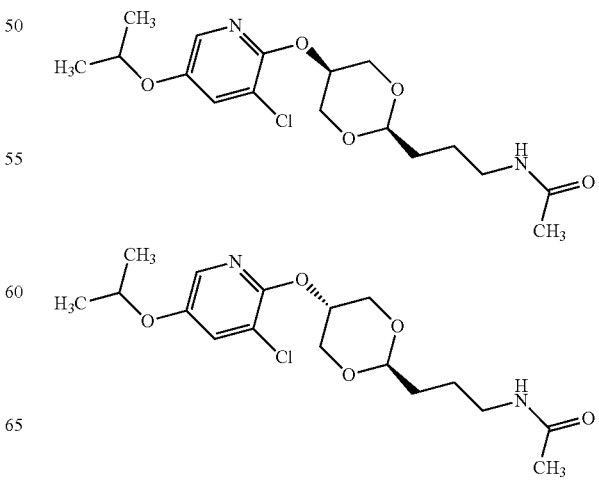

2-(3-Chloro-5-isopropoxypyridin-2-yloxy)propane-1,3-diol (414 mg, 1.58 mmol) was reacted with N-(4,4-diethoxybutyl)acetamide in analogy to example 3d. Yield: cis-N-{3-[5-(3-chloro-5-isopropoxypyridin-2-yloxy)-[1,3]dioxan-2-yl]propyl}acetamide (example 24), 46 mg (8%), M+H+: 373.17 and trans-N-{3-[5-(3-chloro-5-isopropoxypyridin-2-yloxy)-[1,3]dioxan-2-yl]propyl}acetamide (example 25), 43 mg (7%), M+H+: 373.18.

Example 26

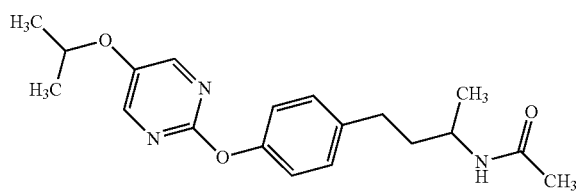 [SMILES: CC(=O)NC(C)CCc1ccc(Oc2ncc(OC(C)C)cn2)cc1]

N-{3-[4-(5-Isopropoxypyrimidin-2-yloxy)phenyl]-1-methylpropyl}acetamide 26a 5-Bromo-2-(6-chloropyridin-3-yloxy)pyrimidine 6-Chloropyridin-3-ol (670 mg, 5.17 mmol) and 5-bromo-2-chloropyrimidine (1.0 g, 5.17 mmol) were reacted in analogy to example 2c. Yield: 1.02 g (69%), M+H+: 285.95.

26b N-{3-[4-(5-Bromopyrimidin-2-yloxy)phenyl]-1-methylpropyl}acetamide

5-Bromo-2-(6-chloropyridin-3-yloxy)pyrimidine (500 mg, 1.745 mmol) and N-[3-(4-hydroxyphenyl)-1-methylpropyl]acetamide (362 mg, 1.745 mmol) were reacted in analogy to example 2c. Yield: 509 mg (80%), M+H+: 364.03.

26c N-{3-[4-(5-Hydroxypyrimidin-2-yloxy)phenyl]-1-methylpropyl}acetamide

N-{3-[4-(5-Bromopyrimidin-2-yloxy)phenyl]-1-methylpropyl}acetamide (509 mg, 1.397 mmol) were dissolved in 5 ml of THF and, at −78° C., n-butyllithium (1.6 M in hexane, 2.18 ml, 3.49 mmol) was added dropwise. This was followed after 20 min by addition of trimethyl borate (0.25 ml, 2.26 mmol), stirring at −78° C. for 2 h and then addition of peracetic acid (35 percent strength, 0.475 ml, 2.26 mmol) and stirring for 10 min. The reaction mixture was warmed to 0° C., stirred for 1 h and hydrolyzed at −10° C. with 5 ml of 10 percent strength sodium hydrogen sulfite solution. The solvent was removed in a rotary evaporator, the aqueous phase was extracted with ethyl acetate, the organic phase was washed with sodium chloride solution, and dried with magnesium sulfate and concentrated. The crude product was purified by preparative HPLC (PR18, acetonitrile/water 0.1% TFA). Yield: 129 mg, M+H+: 302.15. Fraction contains the desired substance only partially.

26d N-{3-[4-(5-Isopropoxypyrimidin-2-yloxy)phenyl]-1-methylpropyl}acetamide

N-{3-[4-(5-Hydroxypyrimidin-2-yloxy)phenyl]-1-methylpropyl}acetamide (125 mg, 0.41 mg) was reacted with 2-iodopropane in analogy to example 36f. Yield: 9 mg (6%), M+H+: 344.14.

Example 27

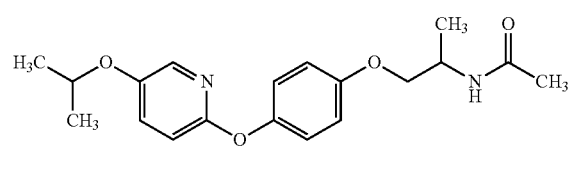 [SMILES: CC(=O)NC(C)COc1ccc(Oc2ccc(OC(C)C)cn2)cc1]

27b 4-(5-Isopropoxypyridin-2-yloxy)phenol

2-Chloro-5-isopropoxypyridine (1.0 g, 5.83 mmol) was reacted with 4-benzyloxyphenol in analogy to example. 2-(4-Benzyloxyphenoxy)-5-isopropoxypyridine: Yield: 693 mg (35%), M+H+: 336.17 and 4-(5-isopropoxypyridin-2-yloxy)phenol Yield: 539 mg (38%), M+H+: 246.13.

27c 2-tert-Butoxycarbonylaminopropyl methanesulfonate tert-Butyl (2-hydroxy-1-methylethyl)carbamate (2.8 g, 15.98 mmol), triethylamine (4.44 ml, 3.23 mmol) and 4-dimethylaminopyridine (195 mg, 1.59 mmol) were dissolved in 135 ml of THF. Methanesulfonyl chloride (1.3 ml, 16.78 mmol) was added dropwise on an ice bath, and the reaction mixture was stirred for 3 h and warmed to room temperature. Following addition of ethyl acetate and sodium bicarbonate solution, the organic phase was separated off and concentrated. Yield: 3.97 g (98%).

27d tert-Butyl {2-[4-(5-isopropoxypyridin-2-yloxy)phenoxy]-1-methylethyl}carbamate 4-(5-Isopropoxypyridin-2-yloxy)phenol (592 mg, 2.41 mmol) and 2-tert-butoxycarbonylaminopropyl methanesulfonate (734 mg, 2.89 mmol) were reacted with sodium hydride in DMF in analogy to example 2c. Yield: 414 mg (43%), M+H+: 403.19.

27e 2-[4-(5-Isopropoxypyridin-2-yloxy)phenoxy]-1-methylethylamine trifluoroacetate tert-Butyl {2-[4-(5-isopropoxypyridin-2-yloxy)phenoxy]-1-methylethyl}carbamate (414 mg, 1.03 mmol) was treated with 90% strength trifluoroacetic acid for 4 h. The trifluoroacetic acid was distilled off and the aqueous phase was freeze dried. The crude product contains excess trifluoroacetic acid and was further reacted without purification.

27f N-{2-[4-(5-Isopropoxypyridin-2-yloxy)phenoxy]-1-methylethyl}acetamide

2-[4-(5-Isopropoxypyridin-2-yloxy)phenoxy]-1-methylethylamine trifluoroacetate (624 mg, 1.5 mmol) was reacted with acetic anhydride in analogy to example 2a. Yield: 251 mg (49%), M+H+: 345.12.

Example 28/29

Chiral chromatography was performed (Chiralcel OJ-H/59, heptane:ethanol:methanol=10:1:1) to obtain the enantiomers N—{(R)-2-[4-(5-Isopropoxypyridin-2-yloxy)phenoxy]-1-methylethyl}acetamide (RF: 11.72 min), Yield: 92 mg (18%), M+H+: 345.13, N—{(S)-2-[4-(5-isopropoxypyridin-2-yloxy)phenoxy]-1-methylethyl}acetamide (RF: 18.69 min), Yield: 95 mg (18%), M+H+: 345.14.

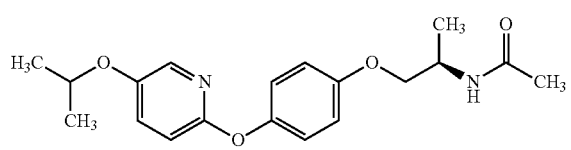 [SMILES: CC(=O)N[C@H](C)COc1ccc(Oc2ccc(OC(C)C)cn2)cc1]

N—{(R)-2-[4-(5-Isopropoxypyridin-2-yloxy)phenoxy]-1-methylethyl}acetamide

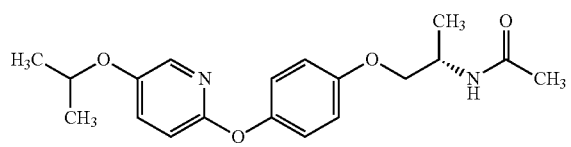 [SMILES: CC(=O)N[C@@H](C)COc1ccc(Oc2ccc(OC(C)C)cn2)cc1]

N—{(S)-2-[4-(5-Isopropoxypyridin-2-yloxy)phenoxy]-1-methylethyl}acetamide

Example 30

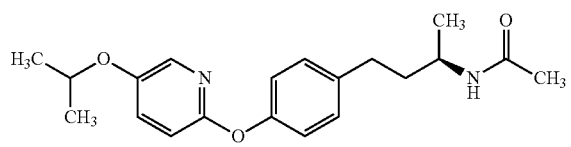 [SMILES: CC(=O)N[C@H](C)CCc1ccc(Oc2ccc(OC(C)C)cn2)cc1]

N—{(R)-3-[4-(5-Isopropoxypyridin-2-yloxy)phenyl]-1-methylpropyl}acetamide

N-{3-[4-(5-Isopropoxypyridin-2-yloxy)phenyl]-1-methylpropyl}acetamide (430 mg) was prepared from 4-(3-aminobutyl)phenol in analogy to example 31. Chiral chromatography was performed (Chiralpak AD-H/83, heptane:ethanol:methanol=15:1:1) to obtain the enantiomers N—{(R)-3-[4-(5-Isopropoxypyridin-2-yloxy)phenyl]-1-methylpropyl}acetamide (RF: 8.74 min), Yield: 130 mg (27%), M+H+: 343.15, N—{(S)-3-[4-(5-isopropoxypyridin-2-yloxy)phenyl]-1-methylpropyl}acetamide (RF: 11.02 min), Yield: 127 mg (26%), M+H+: 343.15.

Example 31

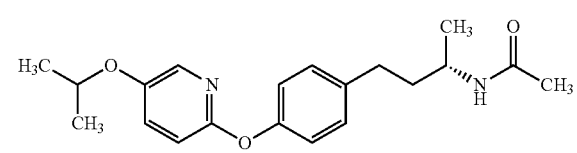 [SMILES: CC(=O)N[C@@H](C)CCc1ccc(Oc2ccc(OC(C)C)cn2)cc1]

N—{(S)-3-[4-(5-Isopropoxypyridin-2-yloxy)phenyl]-1-methylpropyl}acetamide

31a N—[(S)-3-(4-Hydroxyphenyl)-1-methylpropyl]acetamide 4-((S)-3-Aminobutyl)phenol (1.3 g, 7.87 mmol) was reacted with acetic anhydride in analogy to example 2a. Yield: 1.24 g (76%), M+H+: 208.13.

31b N—{(S)-1-Methyl-3-[4-(5-nitropyridin-2-yloxy)phenyl]propyl}acetamide

N—[(S)-3-(4-Hydroxyphenyl)-1-methylpropyl]acetamide (770 mg, 3.72 mmol) and sodium hydride (55% in oil, 243 mg, 5.57 mmol) were stirred in 30 ml of DMF under argon at room temperature for 30 min. Following addition of 2-chloro-5-nitropyridine (648 mg, 4.09 mmol) the mixture was stirred at 80° C. for 1.5 h, concentrated, and mixed with ethyl acetate and water, and the organic phase was separated off and concentrated. The crude product was further reacted without purification.

31c N—{(S)-3-[4-(5-Aminopyridin-2-yloxy)phenyl]-1-methylpropyl}acetamide trifluoroacetate N—{(S)-1-Methyl-3-[4-(5-nitropyridin-2-yloxy)phenyl]propyl}acetamide (1.22 g, 3.7 mmol) and zinc (2.3 g, 35.3 mmol) were suspended in 45 ml of methanol. Under argon, 0.8 ml of acetic acid was slowly added dropwise at room temperature. After 1 h the mixture was filtered, and the filtrate was concentrated and purified by preparative HPLC (PR18, acetonitrile/water 0.1% TFA). Yield: 835 mg (54%), M+H+: 300.15.

31d N—{(S)-3-[4-(5-Hydroxypyridin-2-yloxy)phenyl]-1-methylpropyl}acetamide

Sodium nitrite (154 mg, 2.23 mmol) was dissolved in 2.68 ml of concentrated sulfuric acid at 0° C. Then, N—{(S)-3-[4-(5-aminopyridin-2-yloxy)phenyl]-1-methylpropyl}-acetamide trifluoroacetate (832 mg, 2.01 mmol) in 5 ml of acetic acid was slowly added dropwise. After 1 h the ice bath was removed and stirring was continued for an hour. The reaction mixture was added dropwise to 100 ml of boiling water, the mixture was stirred for 1 h and, after cooling, extracted with ethyl acetate. The precipitated solid was filtered off and the filtrate was concentrated and purified by preparative HPLC (PR18, acetonitrile/water 0.1% TFA). Yield: 153 mg (37%), M+H+: 301.13.

31d N—{(S)-3-[4-(5-Isopropoxypyridin-2-yloxy) phenyl]-1-methylpropyl}acetamide N—{(S)-3-[4-(5-Hydroxypyridin-2-yloxy)phenyl]-1-methylpropyl}acetamide (153 mg, 0.51 mmol) was reacted with 2-iodopropane in analogy to example 1a. Yield: 61 mg (35%), M+H+: 343.15.

Example 32

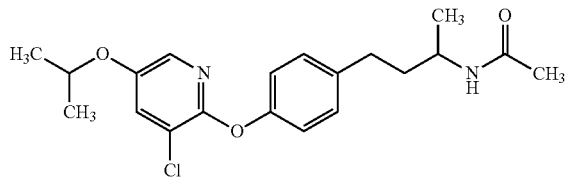 [SMILES: CC(=O)NC(C)CCc1ccc(Oc2ncc(OC(C)C)cc2Cl)cc1]

N-{3-[4-(3-Chloro-5-isopropoxypyridin-2-yloxy) phenyl]-1-methylpropyl}acetamide 2,3-Dichloro-5-isopropoxypyridine (514 mg, 2.496 mmol) and N-[3-(4-hydroxy-phenyl)-1-methylpropyl]acetamide (517 mg, 2.496 mmol) were reacted with sodium hydride in DMF in analogy to example 2c. Yield: 29 mg (3%), M+H+: 377.09. The isomer N-{3-[4-(2-chloro-5-isopropoxypyridin-3-yloxy)phenyl]-1-methylpropyl}acetamide was formed as further compound.

Example 33

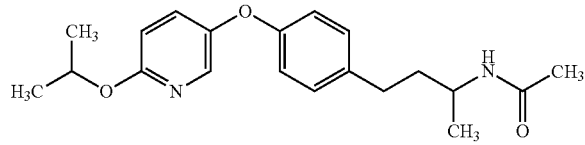 [SMILES: CC(=O)NC(C)CCc1ccc(Oc2ccc(OC(C)C)nc2)cc1]

N-{3-[4-(6-Isopropoxypyridin-3-yloxy)phenyl]-1-methylpropyl}acetamide

N-{3-[4-(6-Hydroxypyridin-3-yloxy)phenyl]-1-methylpropyl}acetamide (168 mg, 1.49 mmol) was reacted with 2-iodopropane in analogy to example 36f. Yield: 26 mg (15%), M+H+: 343.20. N-{3-[4-(1-Isopropyl-6-oxo-1,6-dihydropyridin-3-yloxy)phenyl]1-methylpropyl}acetamide was obtained as by-product.

Example 34

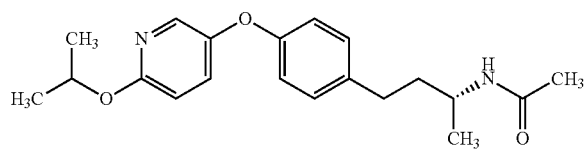 [SMILES: CC(=O)N[C@H](C)CCc1ccc(Oc2ccc(OC(C)C)nc2)cc1]

N—{(R)-3-[4-(6-Isopropoxypyridin-3-yloxy)phenyl]-1-methylpropyl}acetamide

N-{3-[4-(6-Isopropoxypyridin-3-yloxy)phenyl]-1-methylpropyl}acetamide was prepared from 5-(4-bromophenoxy)-2-isopropoxypyridine in analogy to example 36. Chiral chromatography was performed (Chiralcel OJ-H/58, heptane:ethanol:methanol=10:1:1) to obtain the enantiomers N—{(R)-3-[4-(6-isopropoxypyridin-3-yloxy)phenyl]-1-methylpropyl}acetamide (RF: 5.211 min), Yield: 43 mg, M+H+: 343.23, N—{(S)-2-[4-(5-isopropoxypyridin-2-yloxy)phenoxy]-1-methylethyl}acetamide (example 35) (RF: 6.599 min), Yield: 38 mg, M+H+: 343.24.

Example 35

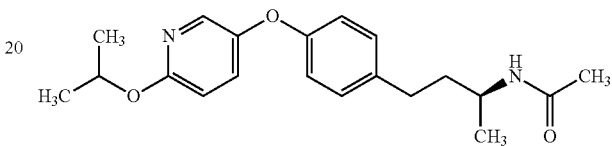

N—{(S)-3-[4-(6-Isopropoxypyridin-3-yloxy)phenyl]-1-methylpropyl}acetamide

Compound 35 was also obtained enantiomerically pure in analogy to example 36 by reaction of 5-(4-bromophenoxy)-2-isopropoxypyridine with 2-((S)-1-methylprop-2-ynyl)isoindole-1,3-dione.

Example 36

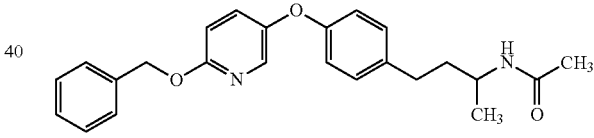

N-{3-[4-(6-Benzyloxypyridin-3-yloxy)phenyl]-1-methylpropyl}acetamide

36a 2-Benzyloxy-5-(4-bromophenoxy)pyridine

6-Benzyloxypyridin-3-ol (1 g, 4.97 mmol), 1,4-bromobenzene (3.51 g, 14.9 mmol) and potassium carbonate (1.43 g, 10.3 mmol) were heated to 80° C. in 30 ml of pyridine. Following addition of copper oxide (976 mg, 12.27 mmol) the mixture was heated to 135° C. for 5 h. Following addition of the further 450 mg of copper oxide the mixture was additionally stirred at 150° C. for 27 h. After cooling, ethyl acetate was added, the mixture was filtered, and the filtrate was concentrated and purified by preparative HPLC (PR18, acetonitrile/water 0.1% TFA). Yield: 826 mg (47%), M+H+: 356.0.

36b 2-{3-[4-(6-Benzyloxypyridin-3-yloxy)phenyl]-1-methylprop-2-ynyl}isoindole-1,3-dione 2-Benzyloxy-5-(4-bromophenoxy)pyridine (826 mg, 2.32 mmol) and 2-(1-methylprop-2-ynyl)isoindole-1,3-dione (693 mg, 3.48 mmol) were dissolved in anhydrous acetonitrile under argon and admixed with triethylamine (2.78 ml, 19.94 mmol), copper iodide (22.1 mg, 0.116 mmol) and bis(triphenylphosphine)palladium(II) chloride (81.4 mg, 0.116 mmol). The reaction mixture was stirred at 100° C. in a microwave reactor for 30 min. A further 0.75 equivalent of the reactants were added and the stirring was continued at 100° C. for a further 60 min. The batch was concentrated, admixed with ethyl acetate and water and filtered, and the organic phase was separated off and concentrated. The crude product was further reacted without purification.

36c 3-[4-(6-Benzyloxypyridin-3-yloxy)phenyl]-1-methylprop-2-ynylamine

2-{3-[4-(6-Benzyloxypyridin-3-yloxy)phenyl]-1-methylprop-2-ynyl}isoindole-1,3-dione (2.0 g, 2.32 mmol) and hydrazine hydrate (0.57 ml, 11.82 mmol) were stirred in 40 ml of ethanol at 100° C. for 2 h. The reaction mixture was concentrated, heated with ethyl acetate and filtered hot. The filtrate was concentrated. Yield: 800 mg (100%), M+H+: 345.15.

36d N-{3-[4-(6-Benzyloxypyridin-3-yloxy)phenyl]-1-methylprop-2-ynyl}acetamide 3-[4-(6-Benzyloxypyridin-3-yloxy)phenyl]-1-methylprop-2-ynylamine (705 mg, 6.97 mmol) was reacted with acetic anhydride in analogy to example 2a. Yield: 370 mg (41%), M+H+: 387.42:

36e N-{3-[4-(6-Hydroxypyridin-3-yloxy)phenyl]-1-methylpropyl}acetamide

N-{3-[4-(6-Benzyloxypyridin-3-yloxy)phenyl]-1-methylprop-2-ynyl}acetamide (370 mg, 0.96 mmol) was hydrogenated in analogy to example 39f. Yield: 313 mg of crude product, M+H+: 301.12.

36f N-{3-[4-(6-Benzyloxypyridin-3-yloxy)phenyl]-1-methylpropyl}acetamide

N-{3-[4-(6-Hydroxypyridin-3-yloxy)phenyl]-1-methylpropyl}acetamide (150 mg, 0.5 mmol) was stirred with potassium tert-butoxide (168 mg, 1.5 mmol) and benzylbromide (342 mg, 2 mmol) in 3 ml of NMP at room temperature for 10 h. The batch was admixed with ethyl acetate and water, and the organic phase was separated off, concentrated and purified by preparative HPLC (PR18, acetonitrile/water 0.1% TFA). Yield: 22 mg (11%), M+H+: 391.15. N-{3-[4-(1-Benzyl-6-oxo-1,6-dihydropyridin-3-yloxy)phenyl]-1-methylpropyl}acetamide was obtained as by-product.

Example 37

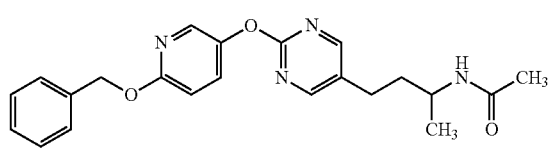 [SMILES: CC(=O)NC(C)CCc1cnc(Oc2ccc(OCc3ccccc3)nc2)nc1]

N-{3-[2-(6-Benzyloxypyridin-3-yloxy)pyrimidin-5-yl]-1-methylpropyl}acetamide was prepared from 2-(6-benzyloxypyridin-3-yloxy)-5-bromopyrimidine in analogy to example 36, M+H+: 393.21.

Example 38

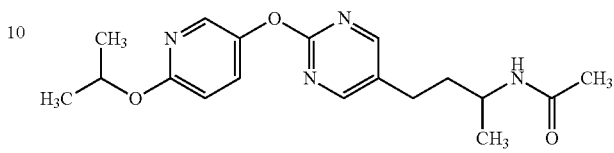

N-{3-[2-(6-Isopropoxypyridin-3-yloxy)pyrimidin-5-yl]-1-methylpropyl}acetamide was prepared from 2-(6-benzyloxypyridin-3-yloxy)-5-bromopyrimidine in analogy to example 36, M+H+: 345.20.

Example 39

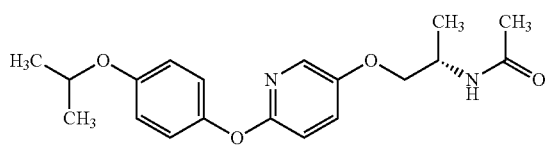 [SMILES: CC(=O)N[C@@H](C)COc1ccc(Oc2ccc(OC(C)C)cc2)nc1]

N—{(S)-2-[6-(4-Isopropoxyphenoxy)pyridin-3-yloxy]-1-methylethyl}acetamide

39a 2-(4-Benzyloxyphenoxy)-5-nitropyridine

2-Chloro-5-nitropyridine (10.0 g, 63.08 mmol) and 4-benzyloxyphenol (12.6 g, 63.08 mmol) were reacted in analogy to example 30b. Yield: 19.5 g (96%), M+H+: 323.11.

39b 6-(4-Benzyloxyphenoxy)pyridin-3-ylamine 2-(4-Benzyloxyphenoxy)-5-nitropyridine (7.84 g, 24.32 mmol) and zinc (15.16 g, 231.8 mmol) were suspended in 300 ml of methanol. Under argon 5.2 ml of acetic acid were slowly added dropwise at room temperature. After 1 h the mixture was filtered and the filtrate was concentrated. The crude product obtained was further reacted without purification.

39c 6-(4-Benzyloxyphenoxy)pyridin-3-ol

Sodium nitrite (1.84 g, 26.7 mmol) was dissolved in 32 ml of concentrated sulfuric acid at 0° C. Then, 6-(4-benzyloxyphenoxy)pyridin-3-ylamine (7.1 g, 24.29 mmol) in 75 ml of acetic acid were slowly added dropwise. After 1 h the ice bath was removed and stirring was continued for an hour. The reaction mixture was added dropwise to 250 ml of boiling water, and the mixture was stirred for 1 hour and after cooling extracted with ethyl acetate. The precipitated solid was filtered off and the filtrate was concentrated and purified by preparative HPLC (PR18, acetonitrile/water 0.1% TFA). Yield: 269 mg (4%), M+H+: 294.10.

39d Benzyl ((S)-2-bromo-1-methylethyl)carbamate

Triphenylphosphine (12.54 g, 47.8 mmol) was dissolved in 100 ml of anhydrous THF and at 0° C. tetrabromomethane (15.85 g, 47.8 mmol) in 100 mL of anhydrous THF was added dropwise. This was followed by the dropwise addition, after 15 min, of benzyl ((S)-2-hydroxy-1-methylethyl)carbamate (5.0 g, 23.9 mmol), dissolved in 150 ml of THF. After 10 min at 0° C. the cooling bath was removed and the mixture was stirred at room temperature overnight. The precipitate which had formed was separated off and washed with ethyl acetate and the combined organic phases were concentrated. The residue obtained was purified over silica gel (ethyl acetate-n-heptane=20:80). Yield: 3.41 g (52%).

39e Benzyl {(S)-2-[6-(4-benzyloxyphenoxy)pyridin-3-yloxy]-1-methylethyl}carbamate 6-(4-Benzyloxyphenoxy)pyridin-3-ol (250 mg, 0.85 mmol) and benzyl ((S)-2-bromo-1-methylethyl)carbamate (232 mg, 0.85 mmol) were reacted with sodium hydride in DMF in analogy to example 1a. Yield: 118 mg (29%), M+H+: 485.11.

39f 4-[5((S)-2-Aminopropoxy)pyridin-2-yloxy]phenol

Benzyl {(S)-2-[6-(4-benzyloxyphenoxy)pyridin-3-yloxy]-1-methylethyl}carbamate (118 mg, 0.24 mmol) were hydrogenated in ethanol over 5% of palladium on carbon at 5 bar hydrogen pressure. The catalyst was filtered off and the filtrate was concentrated: Yield: 43 mg (68%), M+H+: 261.13.

39 g N—{(S)-2-[6-(4-Hydroxyphenoxy)pyridin-3-yloxy]-1-methylethyl}acetamide

4-[5((S)-2-Aminopropoxy)pyridin-2-yloxy]phenol (42 mg, 0.16 mmol) were reacted with acetic anhydride in analogy to example 2a. Yield: 33 mg (68%), M+H+: 303.05.

39h N—{(S)-2-[6-(4-Isopropoxyphenoxy)pyridin-3-yloxy]-1-methylethyl}acetamide N—{(S)-2-[6-(4-Hydroxyphenoxy)pyridin-3-yloxy]-1-methylethyl}acetamide (33 mg, 0.1 mmol) and 2-bromopropane (16 mg, 0.13 mmol) were reacted in analogy to example 1a. Yield: 23 mg (62%), M+H+: 345.19.

Example 40

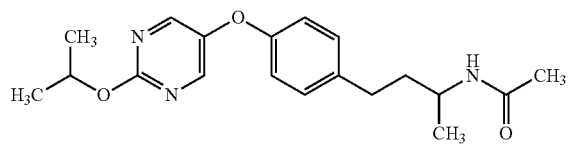

N-{3-[4-(2-Isopropoxypyrimidin-5-yloxy)phenyl]-1-methylpropyl}acetamide

5-Bromo-2-isopropoxypyrimidine (100 mg, 0.46 mmol), N-[3-(4-hydroxyphenyl)-1-methylpropyl]acetamide (95 mg, 0.46 mmol), cesium carbonate (180 mg, 0.552 mmol), copper bromide (66 mg, 0.46 mmol) were stirred in 5 ml of NMP at 160° C. under argon for 5 h. Following addition of equimolar amounts of the components stirring was continued at 160° C. for a further 3 h. The batch was filtered, the filtrate was concentrated and admixed with ethyl acetate and water, and the organic phase was separated off, concentrated and purified by preparative HPLC (PR18, acetonitrile/water 0.1% TFA). Yield: 3 mg (1%), M+H+: 344.23.

Example 41

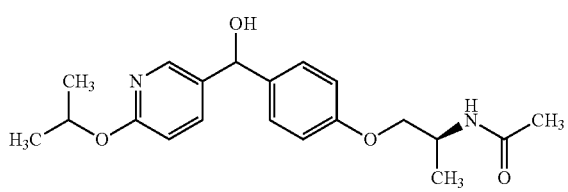 [SMILES: CC(=O)N[C@@H](C)COc1ccc(C(O)c2ccc(OC(C)C)nc2)cc1]

N—((S)-2-{4-[Hydroxy(6-isopropoxypyridin-3-yl)methyl]phenoxy}-1-methylethyl)acetamide (4-Hydroxyphenyl)-(6-isopropoxypyridin-3-yl)methanone (630 mg, 2.45 mmol) was reacted with benzyl ((S)-2-iodo-1-methylethyl)carbamate in analogy to example 39. The subsequent steps were carried out in a corresponding manner. Yield: 229 mg, M+H+: 359.13.

Example 42

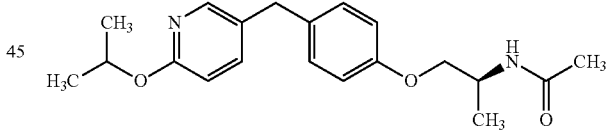

N—{(S)-2-[4-(6-Isopropoxypyridin-3-ylmethyl)phenoxy]-1-methylethyl}acetamide

42a 4-(6-Isopropoxypyridin-3-ylmethyl)phenol (4-Hydroxyphenyl)-(6-isopropoxypyridin-3-yl)methanone (300 mg, 1.17 mmol) was dissolved in 15 ml of THF. Following addition of triethylsilane (678 mg, 5.83 mmol) the mixture was stirred at room temperature for 2 days. Following addition of 116 mg of triethylsilane the mixture was stirred at 60° C. for 8 h, concentrated and admixed with ethyl acetate and water, and the organic phase was separated off, concentrated and purified by preparative HPLC (PR18, acetonitrile/water 0.1% TFA). Yield: 52 mg (18%), M+H+: 244.14.

42b N—{(S)-2-[4-(6-Isopropoxypyridin-3-ylmethyl)phenoxy]-1-methylethyl}acetamide Subsequent steps were carried out in a manner corresponding to example 39. Yield: 10 mg, M+H+: 343.24.

Example 43

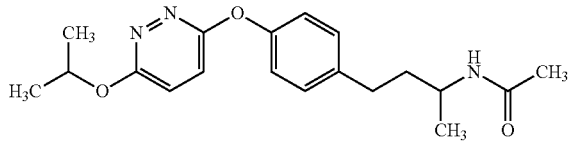 [SMILES: CC(=O)NC(C)CCc1ccc(Oc2ccc(OC(C)C)nn2)cc1]

N-{3-[4-(6-Isopropoxypyridazin-3-yloxy)phenyl]-1-methylpropyl}acetamide

N-[3-(4-Hydroxyphenyl)-1-methylpropyl]acetamide (311 mg, 1.5 mmol) was dissolved in 3 ml of NMP, admixed with sodium hydride (55% in oil) (120 mg, 3 mmol) and, after addition of 3-chloro-6-isopropoxypyridazine (259 mg, 1.5 mmol) stirred in a microwave reactor at 150° C. for 15 min. Following addition of ethyl acetate and water, the organic phase was separated off, concentrated and purified by preparative HPLC (PR18, acetonitrile/water 0.1% TFA). Yield: 40mg (8%), M+H+: 344.2.

Example 44

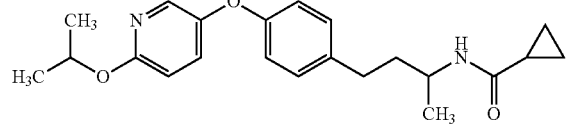

N-{3-[4-(6-Isopropoxypyridin-3-yloxy)phenyl]-1-methylpropyl}cyclopropanecarboxamide 3-[4-(6-Isopropoxypyridin-3-yloxy)phenyl]-1-methylpropylamine trifluoroacetate (115 mg, 0.28 mmol) and triethylamine (0.117 ml, 0.83 mmol) were dissolved in 5 ml of dichloromethane. Cyclopropanecarbonyl chloride (0.043 ml, 0.46 mmol) was added at 0° C. and the reaction mixture was stirred for 3 hours during which it warmed to room temperature. Following addition of water, the organic phase was separated off, concentrated and purified by preparative HPLC (PR18, acetonitrile/water 0.1% TFA). Yield: 63 mg (62%), M+H+: 369.25.

Example 45

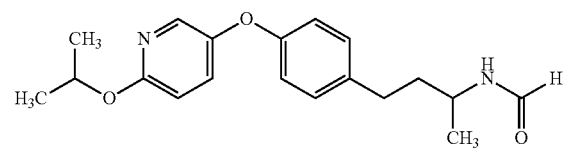 [SMILES: CC(CCc1ccc(Oc2ccc(OC(C)C)nc2)cc1)NC=O]

N-{3-[4-(6-Isopropoxypyridin-3-yloxy)phenyl]-1-methylpropyl}formamide

3-[4-(6-Isopropoxypyridin-3-yloxy)phenyl]-1-methylpropylamine trifluoroacetate (115 mg, 0.28 mmol) was reacted with formic acid and 1,1'-carbonyldiimidazole in analogy to example 44. Yield: 46 mg (51%), M+H+: 329.18.

Example 46

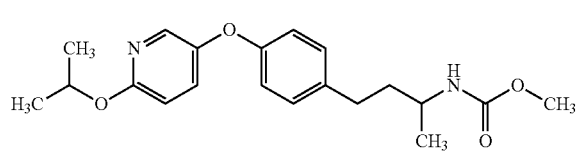 [SMILES: COC(=O)NC(C)CCc1ccc(Oc2ccc(OC(C)C)nc2)cc1]

Methyl {3-[4-(6-isopropoxypyridin-3-yloxy)phenyl]-1-methylpropyl}carbamate

3-[4-(6-Isopropoxypyridin-3-yloxy)phenyl]-1-methylpropylamine trifluoroacetate (115 mg, 0.28 mmol) was reacted with methyl chloroformate in analogy to example 44. Yield: 48 mg (48%), M+H+: 359.13.

Example 47

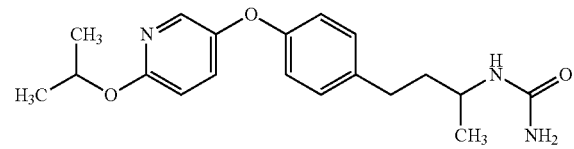 [SMILES: CC(CCc1ccc(Oc2ccc(OC(C)C)nc2)cc1)NC(N)=O]

{3-[4-(6-Isopropoxypyridin-3-yloxy)phenyl]-1-methylpropyl}urea

3-[4-(6-Isopropoxypyridin-3-yloxy)phenyl]-1-methylpropylamine (115 mg, 0.38 mmol) was reacted with formic acid and 1,1'-carbonyldiimidazole in analogy to example 44. Yield: 5 mg (4%), M+H+: 344.19.

Example 48

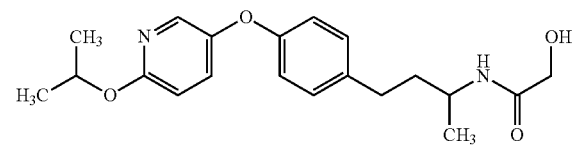

2-Hydroxy-N-{3-[4-(6-isopropoxypyridin-3-yloxy)phenyl]-1-methylpropyl}acetamide

3-[4-(6-Isopropoxypyridin-3-yloxy)phenyl]-1-methylpropylamine trifluoroacetate (89 mg, 0.23 mmol) was reacted with glycolic acid and HATU in analogy to example 44. Yield: 40 mg (52%), M+H+: 359.19.

Example 49

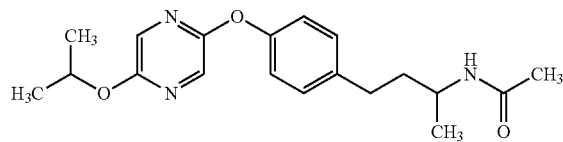 [SMILES: CC(=O)NC(C)CCc1ccc(Oc2cnc(OC(C)C)cn2)cc1]

N-{3-[4-(5-Isopropoxypyrazin-2-yloxy)phenyl]-1-methylpropyl}acetamide

2-Bromo-5-isopropoxypyrazine (100 mg, 0.46 mmol), N-[3-(4-hydroxyphenyl)-1-methylpropyl]acetamide (143 mg, 0.69 mmol), cesium carbonate (300 mg, 0.92 mmol), copper iodide (8.77 mg, 0.046 mmol) and N,N-dimethylglycine hydrochloride (19.3 mg, 0.138 mmol) were stirred in 2 ml of dioxane at 100° C. under argon for 7 h. The batch was filtered, the filtrate was concentrated and admixed with ethyl acetate and water, and the organic phase was separated off, concentrated and purified by preparative HPLC (PR18, acetonitrile/water 0.1% TFA). Yield: 88 mg (56%), M+H+: 344.16.

Example 50

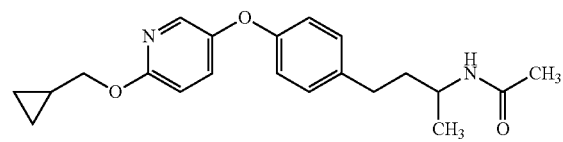 [SMILES: CC(=O)NC(C)CCc1ccc(Oc2ccc(OCC3CC3)nc2)cc1]

N-{3-[4-(6-Cyclopropylmethoxypyridin-3-yloxy)phenyl]-1-methylpropyl}acetamide

50a N-{3-[4-(6-Fluoropyridin-3-yloxy)phenyl]-1-methylpropyl}acetamide

2-Fluoro-5-(4,4,5,5-tetramethyl-[1,3,2]dioxaborolan-2-yl)-pyridine (900 mg, 4.03 mmol), anhydrous copper acetate (550 mg, 3.03 mmol), 1-butylimidazole (175 mg, 1.41 mmol), N-[3-(4-hydroxyphenyl)-1-methylpropyl]acetamide (418 mg, 2.02 mmol) and pyridine (0.326 ml, 4.03 mmol) were admixed with 25 ml of toluene, and stirred at 100° C. for 15 h, under argon. The reaction mixture was filtered and the filtrate was concentrated and purified by preparative HPLC (PR18, acetonitrile/water 0.1% TFA). Yield: 394 mg (32%), M+H+: 303.0.

50b N-{3-[4-(6-Cyclopropylmethoxypyridin-3-yloxy)phenyl]-1-methylpropyl}acetamide N-{3-[4-(6-Fluoropyridin-3-yloxy)phenyl]-1-methylpropyl}acetamide (105 mg, 0.35 mmol), sodium hydride (55% in oil) (42 mg, 1.04 mmol) and cyclopropylmethanol (62 mg, 0.86 mmol) were stirred in 3 ml of NMP at 130° C. under argon for 9 h. After cooling, ethyl acetate and water were added, and the organic phase was separated off, concentrated and purified by preparative HPLC (PR18, acetonitrile/water 0.1% TFA). Yield: 71 mg (58%), M+H+: 355.1.

Example 51

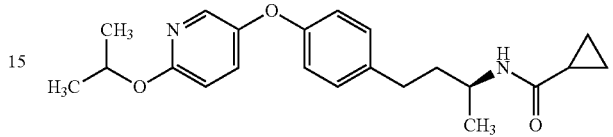

{(S)-3-[4-(6-Isopropoxypyridin-3-yloxy)phenyl]-1-methylpropyl}cyclopropane carboxamide (S)-3-[4-(6-Isopropoxypyridin-3-yloxy)phenyl]-1-methylpropylamine trifluoroacetate (200 mg, 0.48 mmol) was reacted in analogy to example 44. Yield: 138 mg (77%), M+H+: 369.28.

Example 52

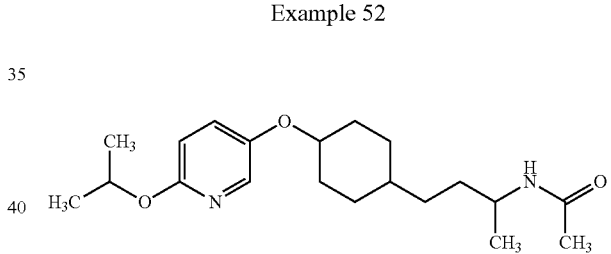

N-{3-[4-(6-Isopropoxypyridin-3-yloxy)cyclohexyl]-1-methylpropyl}acetamide

52a N-[3-(4-Hydroxycyclohexyl)-1-methylpropyl]acetamide

N-[3-(4-Hydroxyphenyl)-1-methylpropyl]acetamide (1.0 g, 4.82 mmol) were dissolved in 100 ml of ethanol and hydrogenated in the presence of 5% rhodium on carbon (695 mg) at 100° C. and 100 bar hydrogen pressure for 18 h. The catalyst was filtered off and the filtrate was concentrated. Yield: 1.06 g of crude product, M+H+: 214.2.

52b N-{3-[4-(6-Isopropoxypyridin-3-yloxy)cyclohexyl]-1-methylpropyl}acetamide 2-Isopropoxy-5-(4,4,5,5-tetramethyl-[1,3,2]dioxaborolan-2-yl)pyridine (913 mg, 3.47 mmol) and N-[3-(4-hydroxycyclohexyl)-1-methylpropyl]acetamide (740 mg, 3.47 mmol) were reacted in analogy to example 50a. Yield: 95 mg (8%), M+H+: 349.3.

Example 53

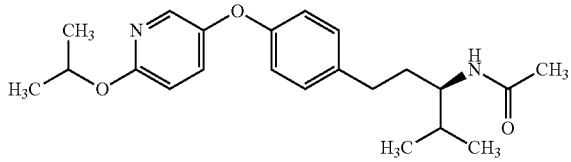 [SMILES: CC(=O)N[C@H](CCc1ccc(Oc2ccc(OC(C)C)nc2)cc1)C(C)C]

N—((R)-1-{2-[4-(6-Isopropoxypyridin-3-yloxy) phenyl]ethyl}-2-methylpropyl)acetamide 53a 1-[4-(6-Isopropoxypyridin-3-yloxy)phenyl]-4-methylpentan-3-one O-benzyloxime 1-[4-(6-Isopropoxypyridin-3-yloxy)phenyl]-4-methylpentan-3-one (310 mg, 0.947 mmol) was stirred with O-benzylhydroxylamine hydrochloride (181 mg, 1.14 mmol) and pyridine (0.92 ml, 1.14 mmol) in 5 ml of ethanol at room temperature for 18 h. The reaction mixture was concentrated and further reacted without purification. Yield: 310 mg, M+H+: 433.26.

53b (R)-1-{2-[4-(6-Isopropoxypyridin-3-yloxy)phenyl]ethyl}-2-methylpropylamine and (S)-1-{2-[4-(6-isopropoxypyridin-3-yloxy)phenyl]ethyl}-2-methylpropylamine Borane-THF (2.87 ml, 2.87 mmol) is added dropwise under argon at 0° C. to 1-[4-(6-isopropoxypyridin-3-yloxy)phenyl]-4-methylpentan-3-one O-benzyloxime (310 mg, 0.717 mmol) in 15 ml of anhydrous THF. Then, (S)-1-[([1,3,2]dioxaborolan-2-yloxy)-diphenylmethyl]-2-methylpropylamine (23.3 mg) is added and the mixture is stirred for 2 days. Following addition of twice 1.5 ml of borane-THF stirring is continued for 4 h each time. % N hydrochloric acid is carefully added for hydrolysis, the mixture is rendered alkaline with aqueous sodium hydroxide solution and extracted with ethyl acetate. The organic phase is separated off, concentrated and purified by preparative HPLC (PR18, acetonitrile/water 0.1% TFA). Yield: 160 mg (68%), M+H+: 329.3. Chiral chromatography is performed (Chiralcel OD-H, heptane:ethanol=5:1+0.1% DEA) to obtain the enantiomers (R)-1-{2-[4-(6-isopropoxypyridin-3-yloxy) phenyl]ethyl}-2-methylpropylamine (RF: 4.442 min), Yield: 49 mg (21%), M+H+: 329.3. (S)-1-{2-[4-(6-Isopropoxypyridin-3-yloxy)phenyl]ethyl}-2-methylpropylamine (RF: 5.965 min), Yield: 50 mg (21%), M+H+: 329.3.

53c N—((R)-1-{2-[4-(6-Isopropoxypyridin-3-yloxy)phenyl]ethyl}-2-methylpropyl)-acetamide (R)-1-{2-[4-(6-Isopropoxypyridin-3-yloxy)phenyl]ethyl}-2-methylpropylamine (48.7 mg, 0.148 mmol) was reacted with acetic anhydride in analogy to example 2a. Yield: 42 mg (77%), M+H+: 371.3.

Example 54

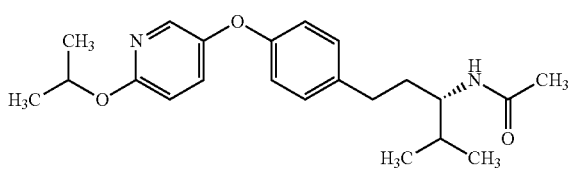 [SMILES: CC(=O)N[C@@H](CCc1ccc(Oc2ccc(OC(C)C)nc2)cc1)C(C)C]

N—((S)-1-{2-[4-(6-Isopropoxypyridin-3-yloxy)phenyl]ethyl}-2-methylpropyl)acetamide (S)-1-{2-[4-(6-Isopropoxypyridin-3-yloxy)phenyl] ethyl}-2-methylpropylamine (50 mg, 0.152 mmol) was reacted with acetic anhydride in analogy to example 2a. Yield: 49 mg (88%), M+H+: 371.3.

Example 55/56

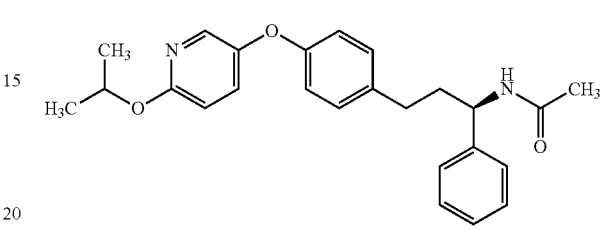

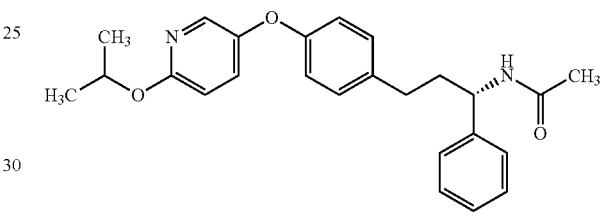

3-[4-(6-Isopropoxypyridin-3-yloxy)phenyl]-1-phenylpropan-1-one (100 mg, 0.277 mmol) was reacted in analogy to example 53. Chiral chromatography was performed (Chiralcel OD-H, heptane:ethanol=5:1+0.1% DEA) to separate N-{3-[4-(6-isopropoxypyridin-3-yloxy)phenyl]-1-phenylpropyl}acetamide into the enantiomers N—{(R)-3-[4-(6-isopropoxypyridin-3-yloxy)phenyl]-1-phenylpropyl}acetamide and N—{(S)-3-[4-(6-isopropoxypyridin-3-yloxy)phenyl]-1-phenylpropyl}acetamide.

Example 57

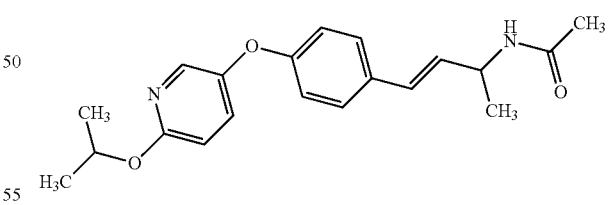

N-{(E)-3-[4-(6-Isopropoxypyridin-3-yloxy)phenyl]-1-methylallyl}acetamide 57a (E)-4-[4-(6-Isopropoxypyridin-3-yloxy)phenyl]but-3-en-2-one 2-Isopropoxy-5-(4,4,5,5-tetramethyl-[1,3,2]dioxaborolan-2-yl)pyridine (3.24 g, 12.33 mmol) and (E)-4-(4-hydroxyphenyl)but-3-en-2-one (2.0 g, 12.33 mmol) were reacted in analogy to example 50a. Yield: 304 mg (8%), M+H+: 298.2.

57b (E)-4-[4-(6-Isopropoxy-pyridin-3-yloxy)-phenyl]-but-3-en-2-one O-benzyl-oxime (E)-4-[4-(6-Isopropoxypyridin-3-yloxy)phenyl]but-3-en-2-one (304 mg, 1.02 mmol) was reacted in analogy to example 53a and further reacted without purification. Yield: 625 mg.

57c (E)-3-[4-(6-Isopropoxy-pyridin-3-yloxy)-phenyl]-1-methyl-allylamine trifluoroacetate (E)-4-[4-(6-Isopropoxy-pyridin-3-yloxy)-phenyl]-but-3-en-2-one O-benzyl-oxime (123 mg, 0.306 mmol) was dissolved in 4 ml ethanol and 4 ml acetic acid. At 0° C. zink (197 mg, 3 mmol) was added, warmed at RT and stirred for 20 h. The solid was separated by filtration and washed with ethanol. The solid was treated with sodium hydroxide solution and extracted with methyl-tert.-butyl ether and the combined organic layers were concentrated and purified by preparative HPLC (PR18, acetonitrile/water 0.1% TFA). Yield: 64 mg (50%), M+H+: 299.3.

57d N-{(E)-3-[4-(6-Isopropoxypyridin-3-yloxy)phenyl]-1-methylallyl}acetamide (E)-3-[4-(6-Isopropoxy-pyridin-3-yloxy)-phenyl]-1-methyl-allylamine trifluoroacetate (63 mg, 0.154 mmol) was reacted with acetic anhydride in analogy to example 2a. M+H+: 341.2.

Example 58

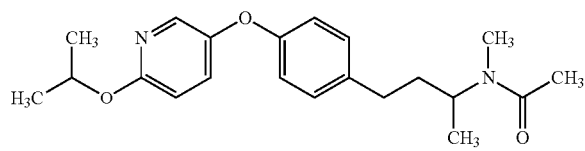

N-{3-[4-(6-Isopropoxy-pyridin-3-yloxy)-phenyl]-1-methyl-propyl}-N-methyl-acetamide

58a {3-[4-(6-Isopropoxy-pyridin-3-yloxy)-phenyl]-1-methyl-propyl}-methyl-amine trifluoroacetate 4-[4-(6-Isopropoxy-pyridin-3-yloxy)-phenyl]-butan-2-one (72 mg, 0.24 mmol) and Methylamin (2 m in THF) (0.24 ml, 0.48 mmol) were dissolved in 2 ml acetonitrile. Under argon atmosphere titanium(IV-)isopropoxide (96 mg, 0.337 mmol) was added at −20° C. and then sodium cyanoborohydride (1 N in THF) (0.24 ml, 0.24 mmol) was added dropwise and stirred for 24 hours. The mixture was warmed at RT, cooled to −20° C. and again titanium(IV-)isopropoxide (96 mg, 0.337 mmol) and sodium cyanoborohydride (1 N in THF) (0.24 ml, 0.24 mmol) were added and warmed within 2 h at room temperature and cooled again. At −20° C. 14 ml 2 N sodium hydroxide solution were added slowly. Ethyl acetate was added and the organic layer separated, concentrated and purified by preparative HPLC (PR18, acetonitrile/water 0.1% TFA). Yield: 27 mg (26%), M+H+: 315.3.

58b N-{3-[4-(6-Isopropoxy-pyridin-3-yloxy)-phenyl]-1-methyl-propyl}-N-methyl-acetamide {3-[4-(6-Isopropoxy-pyridin-3-yloxy)-phenyl]-1-methyl-propyl}-methyl-amine trifluoroacetate (27 mg, 0.086 mmol) was reacted with acetic anhydride in analogy to example 2a. M+H+: 357.2.

Comparative Example 59

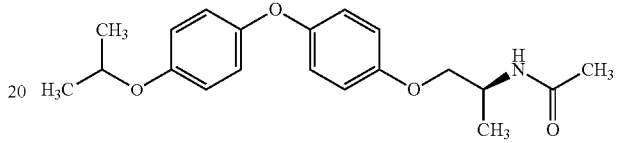

N—{(S)-2-[4-(4-Isopropoxyphenoxy)phenoxy]-1-methylethyl}acetamide

59a tert-Butyl {2-[4-(4-benzyloxyphenoxy)phenoxy]-1-methyl-ethyl}carbamate 4-(4-Benzyloxyphenoxy)phenol (1.948 g, 6.66 mmol), 2-tert-butoxycarbonylaminopropyl methanesulfonate (2.0 g, 6.66 mmol) and cesium carbonate (5.43 g, 16.66 mmol) were stirred in 75 ml of DMF at 80° C. for 3 h. Following addition of 2 g of 2-tert-butoxycarbonylaminopropyl methanesulfonate the reaction mixture was stirred at 80° C. for a further 4 h. The reaction mixture was concentrated in vacuo and the residue is taken up in ethyl acetate and water. The organic phase was separated off, concentrated and the residue was purified by preparative HPLC (PR18, acetonitrile/water 0.1% TFA). Yield: 837 mg (28%).

59b (S)-2-[4-(4-Benzyloxyphenoxy)phenoxy]-1-methylethylamine tert-Butyl {2-[4-(4-benzyloxyphenoxy)phenoxy]-1-methylethyl}carbamate (837 mg, 1.86 mmol) was treated with 90 percent strength trifluoroacetic acid. The trifluoroacetic acid was distilled off and the aqueous phase was freeze dried. Chromatography was performed on a chiral column (ChiralpakAD-H/91, 250 4.6 mm, eluent: heptane/ethanol=3:1+0.1% DEA) for enantiomer separation (S)-2-[4-(4-Benzyloxyphenoxy)phenoxy]-1-methylethylamine (RF: 11.667 min.), Yield: 230 mg (35%), M+H+: 350.19, (R)-2-[4-(4-benzyloxyphenoxy)phenoxy]-1-methylethylamine (RF: 13.122 min.), Yield: 226 mg (35%), M+H+: 350.19.

59c N—{(S)-2-[4-(4-Benzyloxyphenoxy)phenoxy]-1-methylethyl}acetamide (S)-2-[4-(4-Benzyloxyphenoxy)phenoxy]-1-methylethylamine (195 mg, 0.56 mmol) was reacted with acetic anhydride in analogy to example 2a. Yield: 218 mg (100%), M+H+: 392.18.

59d N—{(S)-2-[4-(4-Hydroxyphenoxy)phenoxy]-1-methylethyl}acetamide

N—{(S)-2-[4-(4-Benzyloxyphenoxy)phenoxy]-1-methylethyl}acetamide (218 mg, 0.56 mmol) was hydrogenated in analogy to example 5a. Yield: 139 mg (83%), M+H+: 302.15.

59e N—{(S)-2-[4-(4-Isopropoxyphenoxy)phenoxy]-1-methylethyl}acetamide

N—{(S)-2-[4-(4-Hydroxyphenoxy)phenoxy]-1-methylethyl}acetamide (139 mg, 0.46 mmol) was reacted with 2-iodopropane in analogy to example 10b. Yield: 51 mg (32%), M+H+: 344.23.

The invention claimed is:
1. A compound of the formula I

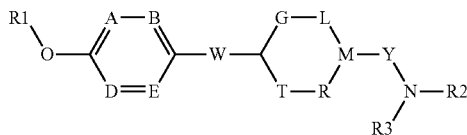

in which the meanings are
A, B, D, E independently of one another C(R5) or N, where not more than two of the radicals A, B, D, E may have the meaning of N;
G, L, R, T, independently of one another =C(R6)-, —C(R6)(R7)-, =N—, —N(R8)- or O, where not more than two of the radicals G, L, R, T may have the meaning of =N—, —N(R8)- or O;
with the proviso that A, B, D, E and G, L, R, T and the C atoms to which they are bonded do not simultaneously form phenyl;
M =C—, —C(R9)- or N;
W O, S, CH(R10);
Y ($C_2$-$C_{10}$)-alkylene, where one or two $CH_2$ groups may be replaced by O, S, N(R10a), —CH=CH—, —CH(phenyl)- or CON(R10b);
R1 ($C_1$-$C_{16}$)-alkyl, ($C_1$-$C_2$)-haloalkyl, ($C_6$-$C_{10}$)-aryl, ($C_3$-$C_{12}$)-heteroaryl, ($C_3$-$C_{12}$)-heterocyclyl, ($C_3$-$C_{12}$)-cycloalkyl, ($C_1$-$C_6$)-alkylene-($C_6$-$C_{10}$)-aryl, ($C_1$-$C_6$)-alkylene-($C_3$-$C_{12}$)-heteroaryl, ($C_1$-$C_6$)-alkylene-($C_3$-$C_{12}$)-heterocyclyl or ($C_1$-$C_6$)-alkylene-($C_3$-$C_{12}$)-cycloalkyl,
where aryl, heteroaryl, heterocyclyl or cycloalkyl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R11)(R12), $SO_2$—$CH_3$, $SO_2$—$NH_2$, $SF_5$, oxo, COOH, COO—($C_1$-$C_6$)-alkyl, CON(R13)(R14), N(R15)CO(R16), N(R17)$SO_2$(R18), CO(R19), (CR20R21)$_x$-O(R22), O—CO—N(R23)(R24), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R25)(R26);
x 0, 1, 2, 3, 4, 5, 6;
R10a, R10b, R11, R12, R13, R14, R15, R16, R17, R18, R19, R20, R21, R22, R23, R24, R25, R26 independently of one another hydrogen, ($C_1$-$C_6$)-alkyl;
R2 hydrogen, —CO—N(R3a)-R4, —CO—R4, —CO—O—R4, ($C_3$-$C_{12}$)-heteroaryl,
where heteroaryl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R27)(R28), $SO_2$—$CH_3$, $SO_2$—$NH_2$, $SF_5$, COOH, COO—($C_1$-$C_6$)-alkyl, CON(R29)(R30), N(R31)CO(R32), N(R33)$SO_2$(R34), CO(R35), (CR36R37)$_{x'}$-O(R38), O—CO—N(R39)(R40), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R41)(R42),
x' 0, 1, 2, 3, 4, 5, 6;
R3, R3a independently of one another hydrogen, ($C_1$-$C_6$)-alkyl, benzyl;
R4 hydrogen, ($C_1$-$C_{16}$)-alkyl, ($C_1$-$C_6$)-alkylen-OH, ($C_6$-$C_{10}$)-aryl, ($C_3$-$C_{12}$)-heteroaryl, —($C_3$-$C_{12}$)-heterocyclyl, ($C_3$-$C_{12}$)-cycloalkyl, ($C_1$-$C_6$)-alkylene-($C_6$-$C_{10}$)-aryl, ($C_1$-$C_6$)-alkylene-($C_3$-$C_{12}$)-heteroaryl, ($C_1$-$C_6$)-alkylene-($C_3$-$C_{12}$)-heterocyclyl or ($C_1$-$C_6$)-alkylene-($C_3$-$C_{12}$)-cycloalkyl,
where aryl, heteroaryl, heterocyclyl or cycloalkyl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R43)(R44), $SO_2$—$CH_3$, $SO_2$—$NH_2$, $SF_5$, COOH, COO—($C_1$-$C_6$)-alkyl, CON(R45)(R46), N(R47)CO(R48), N(R49)$SO_2$(R50), CO(R51), (CR52R53)$_{x''}$-O(R54), O—CO—N(R55)(R56), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R57)(R58),
x" 0, 1, 2, 3, 4, 5, 6;
R27, R28, R29, R30, R31, R32, R33, R34, R35, R36, R37, R38, R39, R40, R41,
R42, R43, R44, R45, R46, R47, R48, R49, R50, R51, R52, R53, R54, R55, R56, R57, R58
independently of one another hydrogen, ($C_1$-$C_6$)-alkyl;
R5 independently of one another hydrogen, ($C_1$-$C_6$)-alkyl, F, Cl, Br, I, OH, $CF_3$, $NO_2$, CN, ($C_2$-$C_4$)-haloalkyl, ($C_2$-$C_6$)-alkenyl, ($C_2$-$C_6$)-alkynyl, N(R59)(R60), $SO_2$—$CH_3$, $SO_2$—$NH_2$, $SF_5$, COOH, COO—($C_1$-$C_6$)-alkyl, CON(R61)(R62), N(R63)CO(R64), N(R65)$SO_2$(R66), CO(R67), (CR68R69)$_{x'''}$-O(R70), O—CO—N(R71)(R72), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R73)(R74);
x''' 0, 1, 2, 3, 4, 5, 6;
R6, R7 independently of one another hydrogen, ($C_1$-$C_6$)-alkyl, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_2$-$C_6$)-alkynyl, N(R75)(R76), $SO_2$—$CH_3$, $SO_2$—$NH_2$, $SF_5$, oxo, COOH, COO—($C_1$-$C_6$)-alkyl, CON(R77)(R78), N(R79)CO(R80), N(R81)$SO_2$(R82), CO(R83), (CR84R85)$_{x''''}$-O(R86), O—CO—N(R87)(R88), O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—N(R89)(R90);

R8 independently of one another hydrogen, $(C_1-C_6)$-alkyl, $CF_3$, CN, $(C_1-C_6)$-alkyl, $(C_2-C_4)$-haloalkyl, $(C_2-C_6)$-alkenyl, $(C_2-C_6)$-alkynyl, $SO_2$—$CH_3$, $SO_2$—$NH_2$, COO—$(C_1-C_6)$-alkyl, CON(R77)(R78), CO(R83), $(CR84R85)_{x''''}$-O(R86);

x'''' 0, 1, 2, 3, 4, 5, 6;

R9, R10 independently of one another hydrogen, $(C_1-C_6)$-alkyl, F, OH, $CF_3$, $(C_2-C_4)$-haloalkyl, $(C_2-C_6)$-alkenyl, $(C_2-C_6)$-alkynyl, $(CR91R92)_y$-O(R93);

y 0, 1, 2, 3, 4, 5, 6;

R59, R60, R61, R62, R63, R64, R65, R66, R67, R68, R69, R70, R71, R72, R73,

R74, R75, R76, R77, R78, R79, R80, R81, R82, R83, R84, R85, R86, R87, R88, R89, R90, R91, R92, R93 independently of one another hydrogen, $(C_1-C_6)$-alkyl; and the pharmaceutically acceptable salts thereof.

2. A compound of the formula I as claimed in claim 1, in which the meanings are

A, B, D, E form with the atoms to which they are bonded a ring system selected from the group:

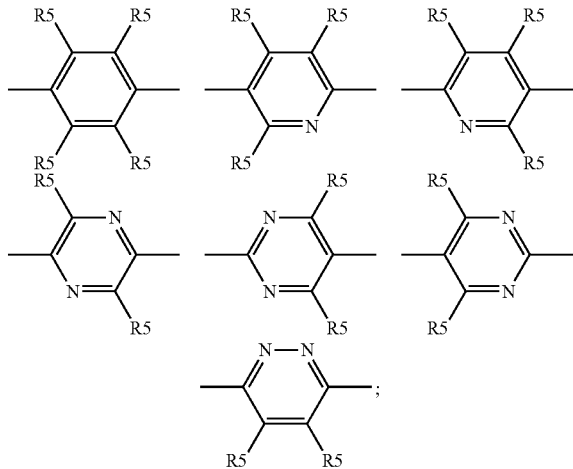

G, L, R, T and M form a ring system selected from the group:

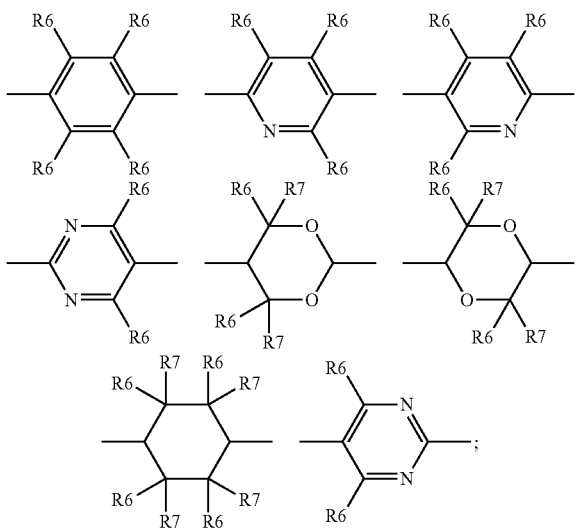

with the proviso that A, B, D, E and G, L, R, T and the C atoms to which they are bonded do not simultaneously form phenyl;

W O, S, CH(R10);

Y C(R11a)(R11b)C(R11c)(R11d)C(R11e)(R11f)-, O—C(R11a)(R11b)C(R11c)(R11d)-, —S—C(R11a)(R11b)C(R11c)(R11d)-, —CH=CH—C(R11a)(R11b)-;

R1 $(C_1-C_{16})$-alkyl, $(C_1-C_2)$-haloalkyl, $(C_6-C_{10})$-aryl, $(C_3-C_{12})$-heteroaryl, $(C_3-C_{12})$-heterocyclyl, $(C_3-C_{12})$-cycloalkyl, $(C_1-C_6)$-alkylene-$(C_6-C_{10})$-aryl, $(C_1-C_6)$-alkylene-$(C_3-C_{12})$-heteroaryl, $(C_1-C_6)$-alkylene-$(C_3-C_{12})$-heterocyclyl or $(C_1-C_6)$-alkylene-$(C_3-C_{12})$-cycloalkyl, where aryl, heteroaryl, heterocyclyl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R11)(R12), $SO_2$—$CH_3$, $SO_2$—$NH_2$, $SF_5$, oxo, COOH, COO—$(C_1-C_6)$-alkyl, CON(R13)(R14), N(R15)CO(R16), N(R17)$SO_2$(R18), CO(R19), $(CR20R21)_x$-O(R22), O—CO—N(R23)(R24), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R25)(R26);

x 0, 1, 2, 3, 4, 5, 6;

R10a, R10b, R11, R12, R13, R14, R15, R16, R17, R18, R19, R20, R21, R22, R23, R24, R25, R26 independently of one another hydrogen, $(C_1-C_6)$-alkyl;

R11a, R11b, R11c, R11d, R11e, R11f independently of one another hydrogen, $(C_1-C_3)$-alkyl, phenyl;

R2 CO—N(R3a)-R4, —CO—R4, —CO—O—R4,

R3, R3a independently of one another hydrogen, $(C_1-C_6)$-alkyl, benzyl;

R4 hydrogen, $(C_1-C_{12})$-alkyl, $(C_1-C_6)$-alkylene-OH, phenyl $(C_3-C_{12})$-heteroaryl, $(C_3-C_{12})$-heterocyclyl, $(C_3-C_{12})$-cycloalkyl, $(C_1-C_6)$-alkylene-$(C_6-C_{10})$-aryl, $(C_1-C_6)$-alkylene-$(C_3-C_{12})$-heteroaryl, $(C_1-C_6)$-alkylene-$(C_3-C_{12})$-heterocyclyl or $(C_1-C_6)$-alkylene-$(C_3-C_{12})$-cycloalkyl, where aryl, heteroaryl, heterocyclyl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R43)(R44), $SO_2$—$CH_3$, $SO_2$—$NH_2$, COOH, COO—$(C_1-C_6)$-alkyl, CON(R45)(R46), N(R47)CO(R48), N(R49)$SO_2$(R50), CO(R51), $(CR52R53)_{x''}$-O(R54), O—CO—N(R55)(R56), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R57)(R58);

x'' 0, 1, 2, 3;

R43, R44, R45, R46, R47, R48, R49, R50, R51, R52, R53, R54, R55, R56, R57, R58 independently of one another, hydrogen, $(C_1-C_6)$-alkyl;

R5 independently of one another hydrogen, $(C_1-C_6)$-alkyl, F, Cl, Br, I, OH, $CF_3$, $NO_2$, CN, $(C_2-C_4)$-haloalkyl, $(C_2-C_6)$-alkenyl, $(C_2-C_6)$-alkynyl, N(R59)(R60), $SO_2$—$CH_3$, $SO_2$—$NH_2$, $SF_5$, COOH, COO—$(C_1-C_6)$-alkyl, CON(R61)(R62), N(R63)CO(R64), N(R65)$SO_2$(R66), CO(R67), $(CR68R69)_{x'}$-O(R70), O—CO—N(R71)

(R72), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R73)(R74);

x''' 0, 1, 2, 3, 4, 5, 6;

R6, R7 independently of one another hydrogen, (C$_1$-C$_6$)-alkyl, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_2$-C$_6$)-alkynyl, N(R75)(R76), SO$_2$—CH$_3$, SO$_2$—NH$_2$, SF$_5$, oxo, COOH, COO—(C$_1$-C$_6$)-alkyl, CON(R77)(R78), N(R79)CO(R80), N(R81)SO$_2$(R82), CO(R83), (CR84R85)$_{x''''}$-O(R86), O—CO—N(R87)(R88), O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—N(R89)(R90);

x'''' 0, 1, 2, 3, 4, 5, 6;

R10 hydrogen, (C$_1$-C$_6$)-alkyl, F, OH, CF$_3$;

R59, R60, R61, R62, R63, R64, R65, R66, R67, R68, R69, R70, R75, R76, R77, R78, R79, R80, R81, R82, R83, R84, R85, R86, R87, R88, R89, R90 independently of one another hydrogen, (C$_1$-C$_6$)-alkyl;

and the pharmaceutically acceptable salts thereof.

3. A compound of the formula I as claimed in claim 1 or 2, in which the meanings are A, B, D, E form with the atoms to which they are bonded a ring system selected from the group:

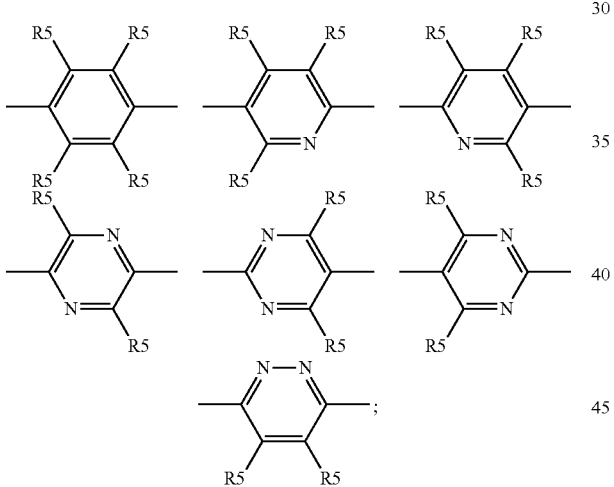

G, L, R, T and M form a ring system selected from the group:

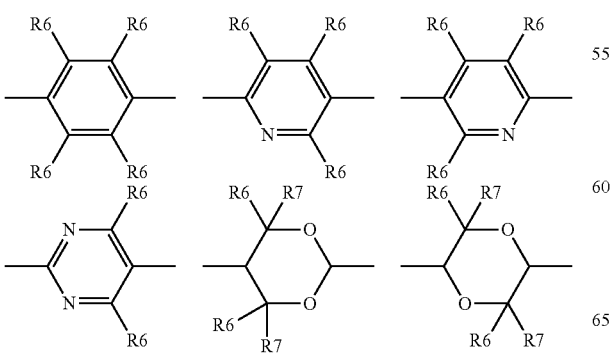

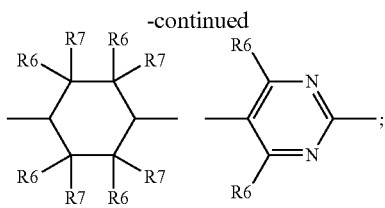

with the proviso that A, B, D, E and G, L, R, T and the C atoms to which they are bonded do not simultaneously form phenyl;

W O, CHOH, CH$_2$;

Y C(R11a)(R11b)C(R11c)(R11d)C(R11e)(R11f)-, O—C(R11a)(R11b)C(R11c)(R11d)-, —S—C(R11a)(R11b)C(R11c)(R11d)-, —CH=CH—C(R11a)(R11b)-;

R1 (C$_1$-C$_8$)-alkyl, CF$_3$, phenyl, (C$_3$-C$_8$)-heteroaryl, (C$_3$-C$_8$)-heterocyclyl, (C$_3$-C$_8$)-cycloalkyl, —CH$_2$-phenyl, —CH$_2$—(C$_3$-C$_8$)-heteroaryl, —CH$_2$—(C$_3$-C$_8$)-heterocyclyl or —CH$_2$—(C$_3$-C$_8$)-cycloalkyl, where aryl, heteroaryl, heterocyclyl or cycloalkyl may be substituted one or more times by F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_4$)-haloalkyl, O—(C$_2$-C$_4$)-haloalkyl, (C$_2$-C$_6$)-alkenyl, (C$_2$-C$_6$)-alkynyl, N(R11)(R12), SO$_2$—CH$_3$, SO$_2$—NH$_2$, oxo, COOH, COO—(C$_1$-C$_6$)-alkyl, CON(R13)(R14), N(R15)CO(R16), N(R17)SO$_2$(R18), CO(R19), (CR20R21)$_x$-O(R22), O—CO—N(R23)(R24), O—CO—(C$_1$-C$_6$)-alkylene-CO—O—(C$_1$-C$_6$)-alkyl;

x 0, 1, 2, 3;

R11a, R11b, R11, R11d, R11e, R11f independently of one another hydrogen, methyl, isopropyl, phenyl;

R11, R12, R13, R14, R15, R16, R17, R18, R19, R20, R21, R22, R23, R24 independently of one another hydrogen, (C$_1$-C$_6$)-alkyl;

R2 —CO—R4, —CO—O—R4;

R3 hydrogen, (C$_1$-C$_6$)-alkyl;

R4 hydrogen, methyl, benzyl, cyclopropyl, CH$_2$OH, NH$_2$;

R5 independently of one another hydrogen, (C$_1$-C$_6$)-alkyl, F, Cl, Br, I, OH, CF$_3$, N(R59)(R60), COO—(C$_1$-C$_6$)-alkyl, CON(R61)(R62), N(R63)CO(R64), CO(R67), (CR68R69)$_{x'''}$-O(R70);

x''' 0, 1, 2, 3, 4, 5, 6;

R6, R7 independently of one another hydrogen, (C$_1$-C$_6$)-alkyl, F, Cl, Br, I, OH, CF$_3$, O—(C$_1$-C$_6$)-alkyl, O—(C$_1$-C$_4$)-alkoxy-(C$_1$-C$_4$)-alkyl, N(R75) (R76), COO—(C$_1$-C$_6$)-alkyl, CON(R77)(R78), CO(R83), (CR84R85)$_{x''''}$-O(R86);

x'''' 0, 1, 2, 3, 4, 5, 6;

R59, R60, R61, R62, R63, R64, R67, R68, R69, R70, R75, R76, R77, R78, R83, R84, R85, R86 independently of one another hydrogen, (C$_1$-C$_6$)-alkyl;

and the pharmaceutically acceptable salts thereof.

4. A compound of the formula I as claimed in claim 1, 2 or 3, in which the meanings are A, B, D, E form with the atoms to which they are bonded a ring system selected from the group:

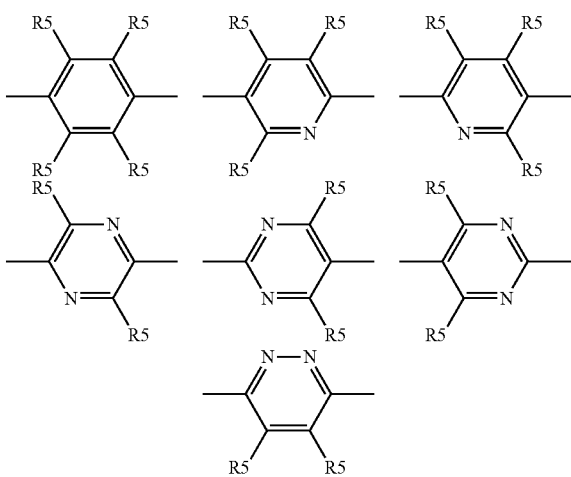

G, L, R, T and M form a ring system selected from the group:

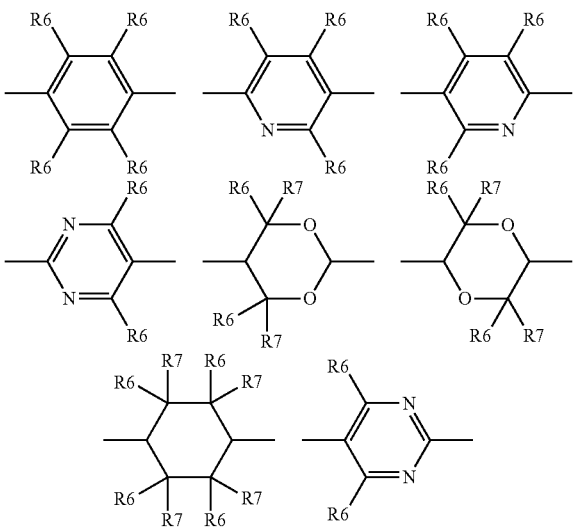

with the proviso that A, B, D, E and G, L, R, T and the C atoms to which they are bonded do not simultaneously form phenyl;

W O, CHOH, CH$_2$;

Y C(R11a)(R11b)C(R11c)(R11d)C(R11e)(R11f)-, O—C(R11a)(R11b)C(R11c)(R11d)-, —S—C(R11a)(R11b)C(R11c)(R11d)-, —CH=CH—C(R11a)(R11b)-;

R1 (C$_3$-C$_8$)-alkyl, CF$_3$, phenyl, pyridyl, isoxazolyl, pyrrolidinyl, cyclopentyl, tetrahydrofuranyl, —CH$_2$-phenyl, —CH$_2$-isoxazolyl, —CH$_2$-pyrrolidinyl, —CH$_{2\text{-}cyclobutyl}$, —$_{CH2}$-cyclopropyl or —CH$_2$-cyclopentyl;

where each of the rings may be substituted once or twice by F, Cl, Br, I, OH, CF$_3$, O—(C$_1$-C$_6$)-alkyl (C$_1$-C$_6$)-alkyl, (C$_2$-C$_4$)-haloalkyl, O—(C$_2$-C$_4$)-haloalkyl, N(R11)(R12), CO(R19), (CR20R21)$_x$-O(R22), O—CO—N(R23)(R24);

x 0, 1, 2, 3;

R11a, R11b, R11, R11d, R11e, R11f independently of one another hydrogen, methyl, isopropyl, phenyl;

R11, R12, R19, R20, R21, R22, R23, R24 independently of one another hydrogen, (C$_1$-C$_6$)-alkyl;

R2 —CO—R4, —CO—O—R4;

R3 hydrogen, (C$_1$-C$_6$)-alkyl;

R4 hydrogen, methyl, benzyl, cyclopropyl, CH$_2$OH, NH$_2$;

R5 independently of one another hydrogen, (C$_1$-C$_6$)-alkyl, F, Cl, Br, I, OH, CF$_3$, O—(C$_1$-C$_6$)-alkyl, N(R59)(R60), COO—(C$_1$-C$_6$)-alkyl, CO(R67);

R6, R7 independently of one another hydrogen, (C$_1$-C$_6$)-alkyl, F, Cl, Br, I, OH, CF$_3$, O—(C$_1$-C$_6$)-alkyl, N(R75)(R76), COO—(C$_1$-C$_6$)-alkyl, CO(R83);

R59, R60, R67, R75, R76, R83 independently of one another hydrogen, (C$_1$-C$_6$)-alkyl;

and the pharmaceutically acceptable salts thereof.

5. A compound of the formula I as claimed in claims 1 to 4, in which Y is —CH$_2$—CH$_2$—CH(CH$_3$)—, —O—CH$_2$—CH(CH$_3$)— or —CH=CH—CH(CH$_3$)—.

6. A compound of the formula I as claimed in claim 1, 2 or 3, in which W is O.

7. A compound of the formula Ic

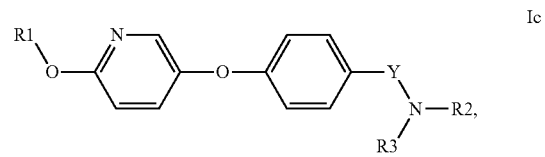

in which the symbols R1, Y, R2, R3 have the meanings mentioned in claims 1 to 4, and the pharmaceutically acceptable salts thereof.

8. A compound of the formula Id

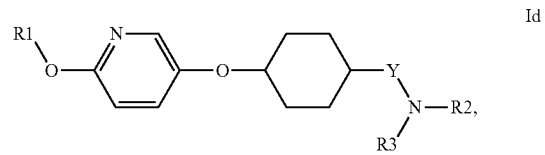

in which the symbols R1, Y, R2, R3 have the meanings mentioned in claims 1 to 4, and the pharmaceutically acceptable salts thereof.

9. A compound of the formula Ia

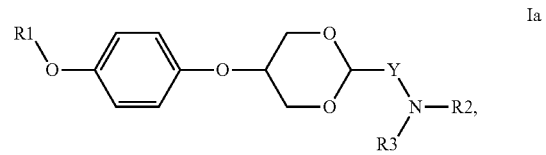

in which the symbols R1, Y, R2, R3 have the meanings mentioned in claims 1 to 4, and the pharmaceutically acceptable salts thereof.

10. A compound of the formula Ib

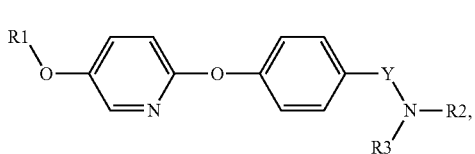

in which the symbols R1, Y, R2, R3 have the meanings mentioned in claims 1 to 4, and the pharmaceutically acceptable salts thereof.

11. A compound of the formula I as claimed in claims 1 to 10, in which

R2 is CO—CH$_3$;

R3 is hydrogen;

and the pharmaceutically acceptable salts thereof.

12. A pharmaceutical composition comprising the compound of claim 1.

13. The pharmaceutical composition according to claim 12, further comprising one or more active ingredients.

14. The pharmaceutical composition according to claim 13, wherein said one or more active ingredients comprises one or more antidiabetics.

15. The pharmaceutical composition according to claim 13, wherein said one or more active ingredients comprises one or more lipid modulators.

16. The pharmaceutical composition according to claim 13, wherein said one or more active ingredients comprises one or more antiobesity agents.

17. A method of treating diabetes mellitus in a patient in need thereof comprising administering to said patient a therapeutically effective amount of the pharmaceutical composition of claim 12.

18. A method of treating obesity in a patient in need thereof comprising administering to said patient a therapeutically effective amount of the pharmaceutical composition of claim 12.

19. A process for the manufacture of a medicament comprising one or more of the compounds as claimed in one or more of claims 1 to 11, which comprises mixing the active ingredient with a pharmaceutically suitable carrier and converting this mixture into a form suitable for administration.

* * * * *

UNITED STATES PATENT AND TRADEMARK OFFICE
CERTIFICATE OF CORRECTION

PATENT NO. : 8,470,841 B2  
APPLICATION NO. : 13/002933  
DATED : June 25, 2013  
INVENTOR(S) : Zoller et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 97 days.

Signed and Sealed this
Eighth Day of September, 2015

Michelle K. Lee
*Director of the United States Patent and Trademark Office*